United States Patent
Nascimento et al.

(10) Patent No.: US 10,206,959 B2
(45) Date of Patent: *Feb. 19, 2019

(54) PROBIOTIC ARGINOLYTIC ORAL COMPOSITIONS AND METHODS OF MAKING AND USING PROBIOTIC ARGINOLYTIC ORAL COMPOSITIONS

(71) Applicant: University of Florida Research Foundation, Inc., Gainesville, FL (US)

(72) Inventors: Marcelle Matos Nascimento, Gainesville, FL (US); Robert A. Burne, Gainesville, FL (US)

(73) Assignee: University of Florida Research Foundation, Inc., Gaines, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/417,669

(22) Filed: Jan. 27, 2017

(65) Prior Publication Data
US 2017/0136074 A1 May 18, 2017

Related U.S. Application Data

(63) Continuation-in-part of application No. 14/767,181, filed as application No. PCT/US2014/016139 on Feb. 12, 2014, now Pat. No. 9,655,839.

(60) Provisional application No. 61/764,579, filed on Feb. 14, 2013.

(51) Int. Cl.
| | |
|---|---|
| *A61K 31/198* | (2006.01) |
| *A61K 31/7004* | (2006.01) |
| *A61K 35/741* | (2015.01) |
| *A61Q 11/00* | (2006.01) |
| *C12Q 1/14* | (2006.01) |
| *A61K 35/744* | (2015.01) |
| *A61Q 17/00* | (2006.01) |
| *A61K 8/99* | (2017.01) |

(52) U.S. Cl.
CPC .............. *A61K 35/744* (2013.01); *A61K 8/99* (2013.01); *A61Q 11/00* (2013.01); *A61Q 17/005* (2013.01)

(58) Field of Classification Search
None
See application file for complete search history.

(56) References Cited

U.S. PATENT DOCUMENTS

| | | |
|---|---|---|
| 2002/0094328 A1 | 7/2002 | De Simone |
| 2007/0212311 A1 | 9/2007 | Burne et al. |
| 2011/0085990 A1 | 4/2011 | Sullivan et al. |

FOREIGN PATENT DOCUMENTS

| | | |
|---|---|---|
| WO | 2012028759 | 3/2012 |

OTHER PUBLICATIONS

Mouth Diseases https://www.ncbi.nlm.nih.gov/mesh/?term=oral+disorder Retrieved Feb. 16, 2018.*
International Search Report for PCT/US2014/016139 dated May 28, 2014.
Liu, Y. et al., 'Multiple two-component systems modulate alkali generation in *Streptococcus gordonii* in response to environmental stresses', Journal of Bacteriology, 2009, vol. 191, No. 23, pp. 7353-7362.
Clancy, K. A. et al., 'Characterization of recombinant, ureolytic *Streptococcus mutans* demonstrates an inverse relationship between dental plaque ureolytic capacity and cariogenicity', Infect ion and Immunity, 2000, vol. 68, No. 5, pp. 2621-2629.
International Search Report dated Jul. 22, 2016, Application No. EP14750993; European Patent Office, Munich, Germany; 10 pages.
Nascimento, MM, et al. "Correlations of oral bacterial arginine and urea catabolism with caries experience". Oral Microbiology and Immunology; 2009: 24: pp. 89-95; John Wiley & Sons NS.
Liu, Ya-Ling, et al; "Progress toward understanding the contribution of alkali generation in dental biofilms to inhibition of dental caries"; International Journal of Oral Science (2012) 4, pp. 135-140; www.nature.com/ijos.
Gordan, V.V. et al; "Could Alkali Production Be Considered an Approach for Caries Control?" Caries Research; 2010; 44: pp. 547-554; 8 pages.
Jalasvuori, Heli, et al.; "Probiotic Lactobacillus reuteri strains ATCC PTA 5289 and ATCC 55730 differ in their ariogenic properties in vitro"; Department of Cariology, Institute of Dentistry, University of Turku, Turku, Finland; Archives of Oral Biology 57 (2012) pp. 1633-1638.
Dong et al. Applied and Environmental Microbiology, 68:5549-553, 2002.
Dong et al. Journal of Bacteriology, Apr. 2004, p. 2511-2514, 186 (8): 2511-2514.
LiU et al. Characterization of Arginolytic Microflora of Human Oral Biofilms. AADR Annual Meeting, Poster Session Abstract, Saturday Mar. 24, 2012.
Kreth et al. Journal of Bacteriology, Jul. 2008, p. 4623-4640 vol. 190, No. 13.
Christopher et al. Microbiology (201 0), 156, 3469-3477.
Nascimento Et Ao. Oral MicrobiolImmunol. Author Manuscript, available in PMC Apr. 1, 2010 pp. 1-16.
Burne et al. FEMS Microbiology Letters 193 (2000) 1-6.
Richards VP, Palmer SR, Pavinski Bitar PD, Qin X, Weinstock GM, Highlander SK, Town CD, Burne RA, Stanhope MJ. 2014. Phylogenomics and the dynamic genome evolution of the genus *Streptococcus*. Genome Biol Evol 6:741-753.
He J., Hwang G, Liu Y, Gao L, Kilpatrick-Liverman L, Santarpia P, Zhou X, Koo H: L-arginine modifies the exopolysaccharides matrix and thwarts *Streptococcus mutans* outgrowth within mixed-species oral biofilms. Journal of Bacteriology 2016;198(19):2651-2661; American Society for Microbiology.
Huang X, Schulte RM, Burne RA, Nascimento MM. 2015. Characterization of the arginolytic microflora provides insights into pH homeostasis in human oral biofilms. Caries Research 2015; 49:165-176.

(Continued)

*Primary Examiner* — Oluwatosin A Ogunbiyi
(74) *Attorney, Agent, or Firm* — Thomas Horstemeyer, LLP

(57) ABSTRACT

The present disclosure provides methods of using probiotic arginolytic oral compositions including isolated arginolytic bacterial strains to increase arginolytic activity in the oral cavity, increase ammonia-producing bacteria in the oral cavity, and/or to treat and/or prevent oral disorders, such as caries.

15 Claims, 21 Drawing Sheets

Specification includes a Sequence Listing.

(56) References Cited

OTHER PUBLICATIONS

Huang X, Palmer SR, Ahn S-J, Richards VP, Williams ML, Nascimento MM, Burne RA: A highly arginolytic *Streptococcus* species that potently antagonizes Streptococcus mutans. Applied Environmental Microbiology 2016;82:2187-2201.

Kreth J, Merritt J, Shi W, Qi F: Competition and coexistence between *Streptococcus mutans* and *Streptococcus sanguinis* in the dental biofilm. Journal of Bacteriology, Nov. 2005;187:7193-7203.

Kreth J, Zhang Y, Herzberg MC: Streptococcal antagonism in oral biofilms: *Streptococcus sanguinis* and *Streptococcus gordonii* interference with *Streptococcus mutans*. Journal of Bacteriology, Jul. 2008;190:4632-4640.

Liu L, Tong H, Dong X: Function of the pyruvate oxidase-lactate oxidase cascade in interspecies competition between *Streptococcus oligofermentans* and *Streptococcus mutans*. Appl Environ Microbiol 2012;78:2120-2127.

Tong H, Chen W, Merritt J, Qi F, Shi W, Dong X: *Streptococcus oligofermentans* inhibits *Streptococcus mutans* through conversion of lactic acid into inhibitory H2O2: a possible counteroffensive strategy for interspecies competition. Molecular Microbiology 2007;63:872-880.

Wang B-Y, Kuramitsu Hk. 2005. Interactions between oral bacteria: inhibition of *Streptococcus mutans* bacteriocin production by *Streptococcus gordonii*. Appl Environ Microbiology 71:354-362.

Zeng L, Dong Y, Burne RA. 2006. Characterization of cis-acting sites controlling arginine deiminase gene expression in *Streptococcus gordonii*. Journal of Bacteriology 188:941-949.

Zheng L, Chen Z, Itzek A, Ashby M, Kreth J: Catabolite control protein A controls hydrogen peroxide production and cell death in *Streptococcus sanguinis*. Journal of Bacteriology 2011;193:516-526.

Zhu L, Kreth J: The role of hydrogen peroxide in environmental adaptation of oral microbial communities. Oxidative Medicine and Cellular Longevity 2012;2012:717843.

\* cited by examiner

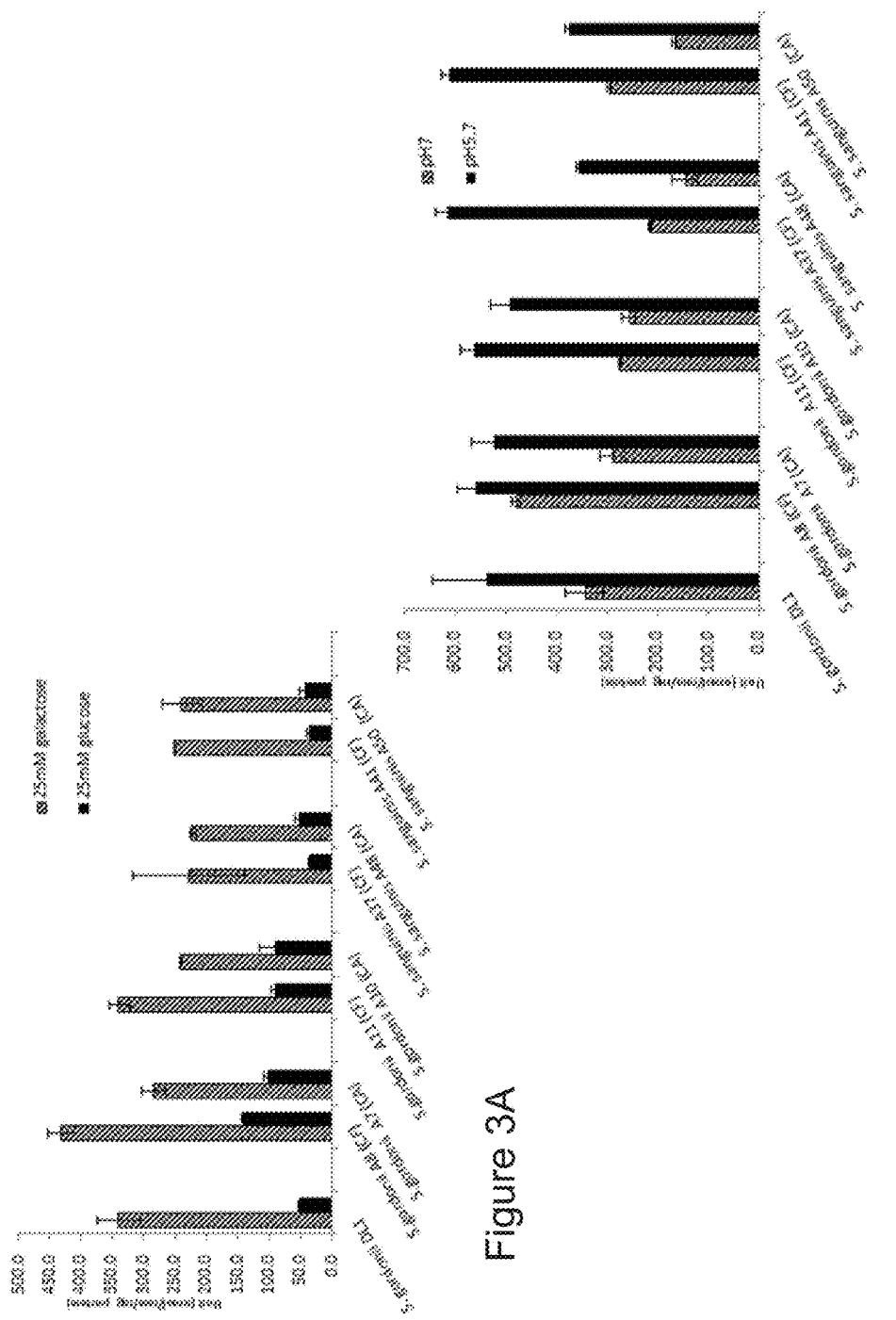

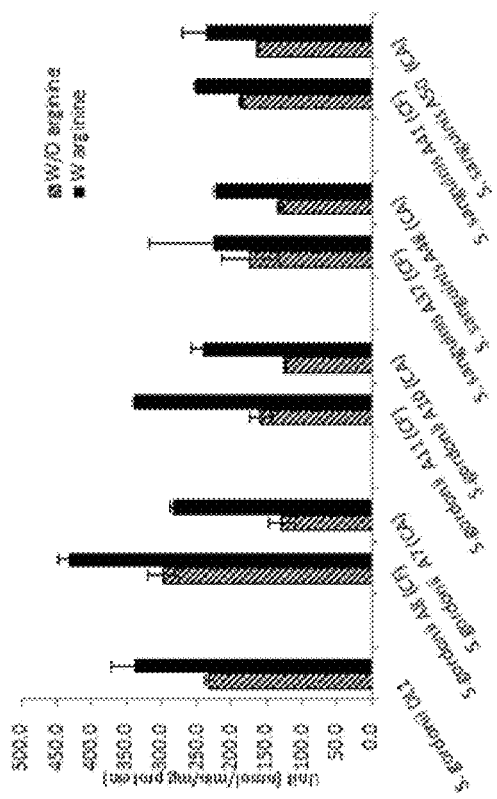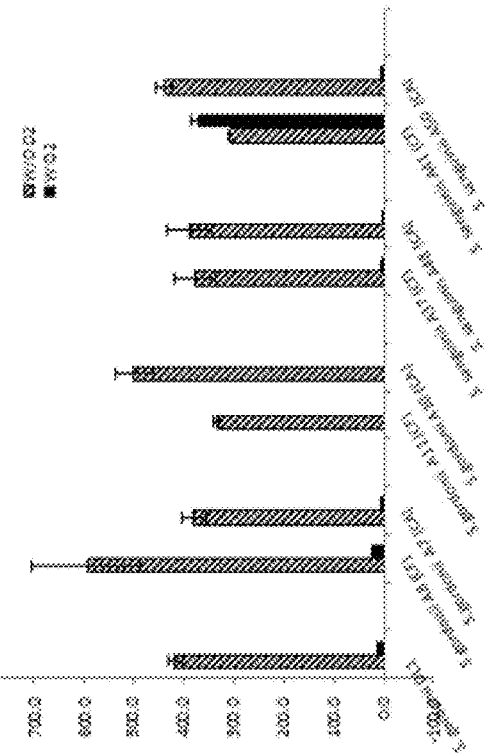

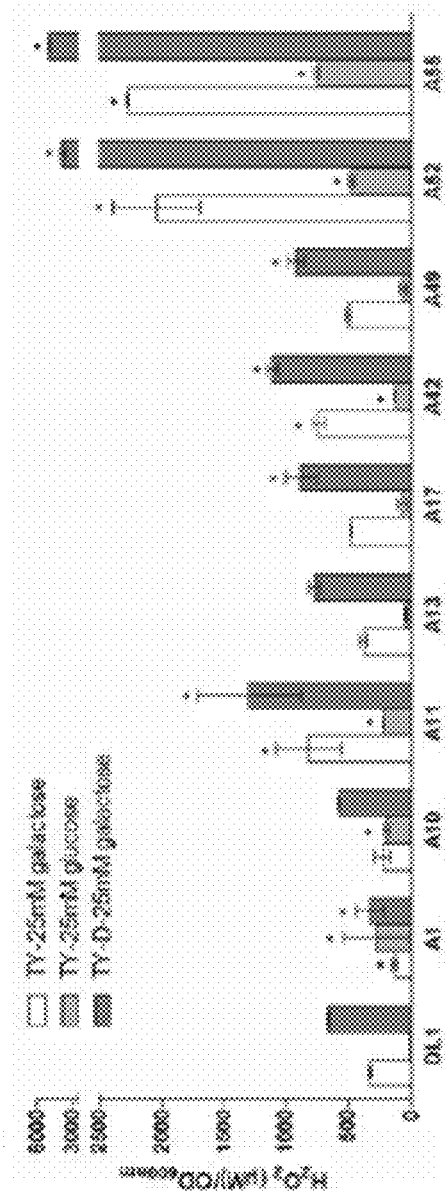
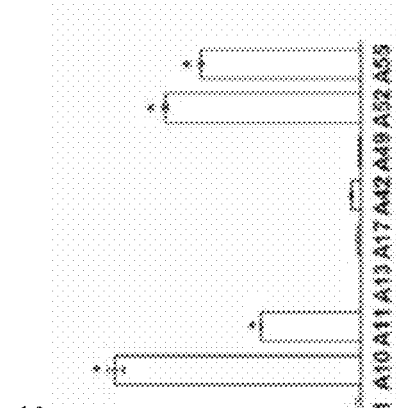
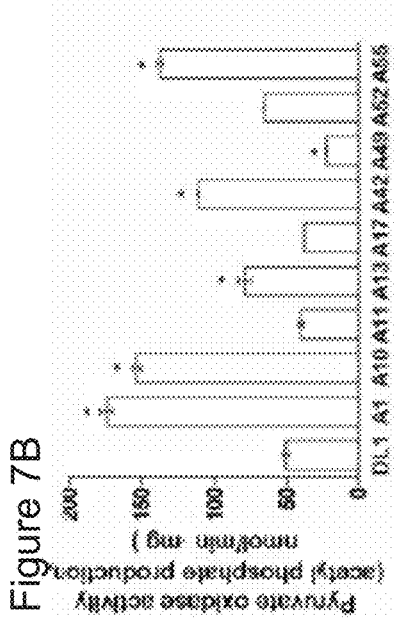
Figure 7A
Figure 7B
Figure 7C

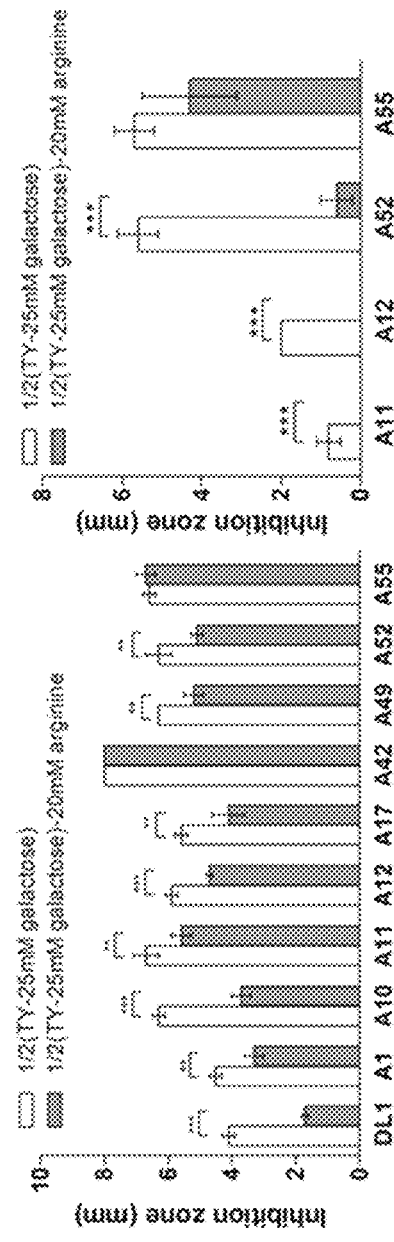
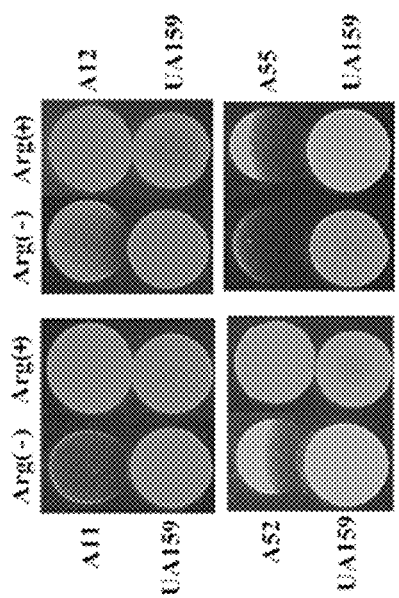
Figure 8A
Figure 8B
Figure 8C

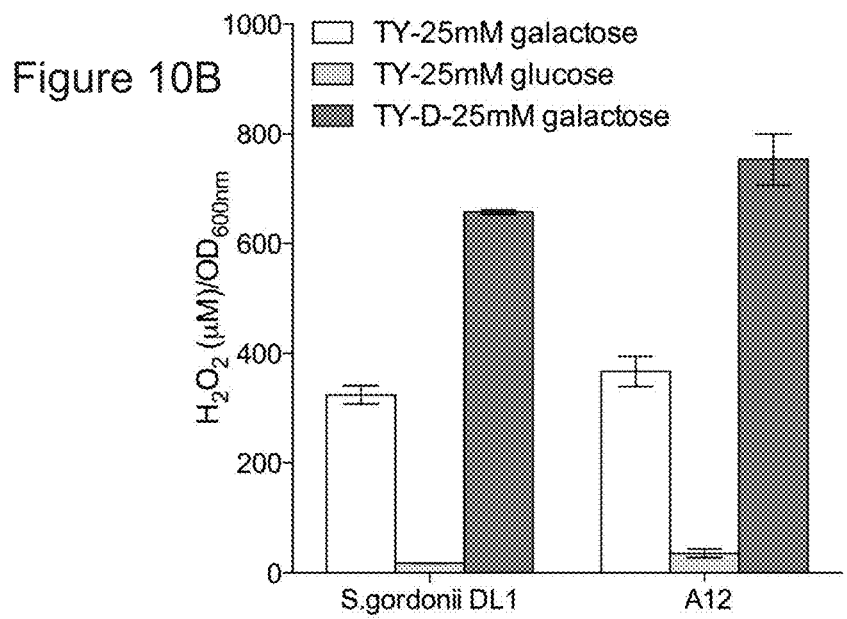
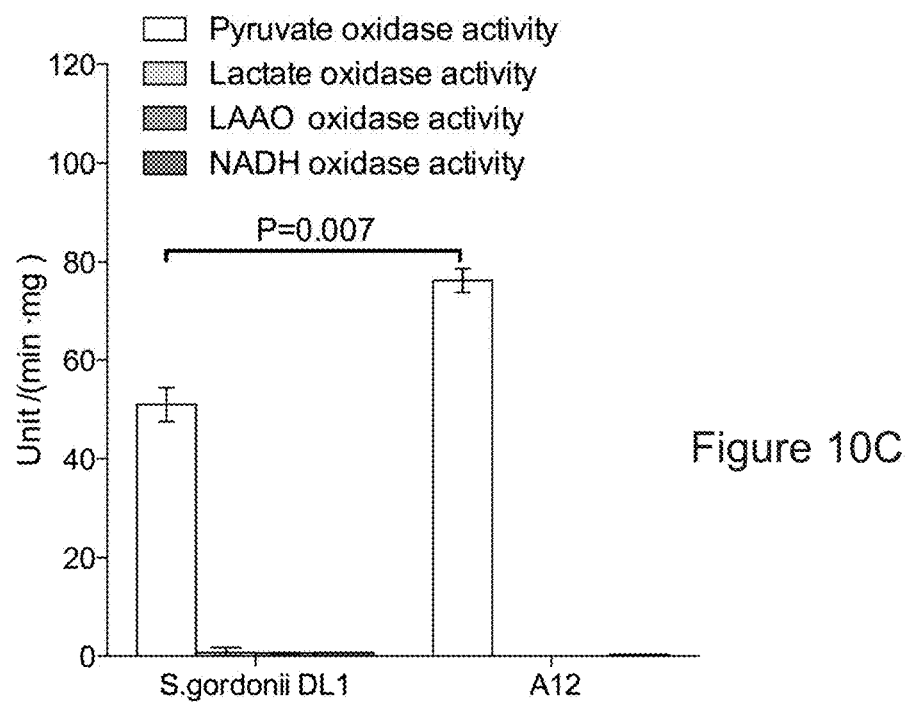

SEQUENCE LISTING

<160> NUMBER OF SEQ ID NOS: 22

<210> SEQ ID NO 1
<211> LENGTH: 20
<212> TYPE: DNA
<213> ORGANISM: Artificial Sequence
<220> FEATURE:
<223> OTHER INFORMATION: chemically synthesized forward 16S rRNA primer
      sequence

<400> SEQUENCE: 1
agagtttgat cctggctcag                                              20

<210> SEQ ID NO 2
<211> LENGTH: 21
<212> TYPE: DNA
<213> ORGANISM: Artificial Sequence
<220> FEATURE:
<223> OTHER INFORMATION: chemically synthesized reverse 16S rRNA primer
      sequence

<400> SEQUENCE: 2
tacgggtacc ttgttacgac t                                            21

<210> SEQ ID NO 3
<211> LENGTH: 20
<212> TYPE: DNA
<213> ORGANISM: Artificial Sequence
<220> FEATURE:
<223> OTHER INFORMATION: Chemically synthesized primer for A12-arcR-5'-F

<400> SEQUENCE: 3
tttcacaccc gagctcttac                                              20

<210> SEQ ID NO 4
<211> LENGTH: 32
<212> TYPE: DNA
<213> ORGANISM: Artificial Sequence
<220> FEATURE:
<223> OTHER INFORMATION: Chemically synthesized primer for
      A12-arcR-5'-R-SOE

<400> SEQUENCE: 4
actccttctg gtggcgactt tcaatcttat tc                                32

<210> SEQ ID NO 5
<211> LENGTH: 33
<212> TYPE: DNA
<213> ORGANISM: Artificial Sequence
<220> FEATURE:
<223> OTHER INFORMATION: Chemically synthesized primer for
      A12-arcR-Erm-F-SOE

<400> SEQUENCE: 5
gtcgccacca gaaggagtga ttacatgaac aaa         33

<210> SEQ ID NO 6
<211> LENGTH: 31
<212> TYPE: DNA
<213> ORGANISM: Artificial Sequence
<220> FEATURE:
<223> OTHER INFORMATION: Chemically synthesized primer for
      A12-arcR-Erm-R-SOE

<400> SEQUENCE: 6
gaggcagacc cctttagtaa cgtgtaactt t           31

<210> SEQ ID NO 7
<211> LENGTH: 30
<212> TYPE: DNA
<213> ORGANISM: Artificial Sequence
<220> FEATURE:
<223> OTHER INFORMATION: Chemically synthesized primer for
      A12-arcR-3'-F-SOE

<400> SEQUENCE: 7
actaaagggg tctgcctcat catctgtgaa             30

<210> SEQ ID NO 8
<211> LENGTH: 21
<212> TYPE: DNA
<213> ORGANISM: Artificial Sequence
<220> FEATURE:
<223> OTHER INFORMATION: Chemically synthesized primer for A12-arcR-3'-R

<400> SEQUENCE: 8
ctctccattg atgaacagca a                      21

<210> SEQ ID NO 9
<211> LENGTH: 22
<212> TYPE: DNA
<213> ORGANISM: Artificial Sequence
<220> FEATURE:
<223> OTHER INFORMATION: Chemically synthesized primer for A12-spxB-5'-F

<400> SEQUENCE: 9
gaattggcgc aagggatgat aa                     22

<210> SEQ ID NO 10
<211> LENGTH: 31
<212> TYPE: DNA
<213> ORGANISM: Artificial Sequence
<220> FEATURE:
<223> OTHER INFORMATION: Chemically synthesized primer for
      A12-spxB-5'-R-SOE

<400> SEQUENCE: 10
tttctacagg atagtgtcta cgccccatgt t           31

<210> SEQ ID NO 11
<211> LENGTH: 29
<212> TYPE: DNA
<213> ORGANISM: Artificial Sequence
<220> FEATURE:
<223> OTHER INFORMATION: Chemically synthesized primer for
      A12-spxB-Kan-F-SOE

<400> SEQUENCE: 11
gacactatcc tgtagaaaag aggaaggaa              29

<210> SEQ ID NO 12
<211> LENGTH: 32
<212> TYPE: DNA
<213> ORGANISM: Artificial Sequence
<220> FEATURE:
<223> OTHER INFORMATION: Chemically synthesized primer for
      A12-spxB-Kan-R-SOE

<400> SEQUENCE: 12
tggtacaagg agtatggaca gttgcggatg ta                           32

<210> SEQ ID NO 13
<211> LENGTH: 32
<212> TYPE: DNA
<213> ORGANISM: Artificial Sequence
<220> FEATURE:
<223> OTHER INFORMATION: Chemically synthesized primer for
      A12-spxB-3'-F-SOE

<400> SEQUENCE: 13
tccatactcc ttgtaccatt ccgtctcttc tt                           32

<210> SEQ ID NO 14
<211> LENGTH: 24
<212> TYPE: DNA
<213> ORGANISM: Artificial Sequence
<220> FEATURE:
<223> OTHER INFORMATION: Chemically synthesized primer for A12-spxB-3'-R

<400> SEQUENCE: 14
ccacttacta gcagggattc ggtt                                    24

<210> SEQ ID NO 15
<211> LENGTH: 23
<212> TYPE: DNA
<213> ORGANISM: Artificial Sequence
<220> FEATURE:
<223> OTHER INFORMATION: Chemically synthesized primer for A12-sgc-5'-F

<400> SEQUENCE: 15
ccatttggcc aaggagagtt gtt                                     23

<210> SEQ ID NO 16
<211> LENGTH: 31
<212> TYPE: DNA
<213> ORGANISM: Artificial Sequence
<220> FEATURE:
<223> OTHER INFORMATION: Chemically synthesized primer for
      A12-sgc-5'-R-SOE

<400> SEQUENCE: 16
cactccttcg aacagatcct aatagcaccg a                            31

<210> SEQ ID NO 17
<211> LENGTH: 31
<212> TYPE: DNA
<213> ORGANISM: Artificial Sequence
<220> FEATURE:
<223> OTHER INFORMATION: Chemically synthesized primer for
      A12-sgc-Erm-F-SOE

<400> SEQUENCE: 17
gatctgttcg aaggagtgat tacatgaaca a                            31

<210> SEQ ID NO 18
<211> LENGTH: 31
<212> TYPE: DNA

```
<213> ORGANISM: Artificial Sequence
<220> FEATURE:
<223> OTHER INFORMATION: Chemically synthesized primer for
      A12-sgc-Erm-R-SOE

<400> SEQUENCE: 18
caggattagc cctttagtaa cgtgtaactt t                                31

<210> SEQ ID NO 19
<211> LENGTH: 29
<212> TYPE: DNA
<213> ORGANISM: Artificial Sequence
<220> FEATURE:
<223> OTHER INFORMATION: Chemically synthesized primer for
      A12-sgc-3'-F-SOE

<400> SEQUENCE: 19
actaaagggc taatcctggt gctagtcaa                                   29

<210> SEQ ID NO 20
<211> LENGTH: 22
<212> TYPE: DNA
<213> ORGANISM: Artificial Sequence
<220> FEATURE:
<223> OTHER INFORMATION: Chemically synthesized primer for A12-sgc-3'-R

<400> SEQUENCE: 20
cctggagaag aactatacgt aa                                          22

<210> SEQ ID NO 21
<211> LENGTH: 25
<212> TYPE: DNA
<213> ORGANISM: Artificial Sequence
<220> FEATURE:
<223> OTHER INFORMATION: Chemically synthesized primer for cipB5'
      promoter region

<400> SEQUENCE: 21
tcatggattg agctcaaaaa gtaat                                       25

<210> SEQ ID NO 22
<211> LENGTH: 25
<212> TYPE: DNA
<213> ORGANISM: Artificial Sequence
<220> FEATURE:
<223> OTHER INFORMATION: Chemically synthesized primer for cipB3'
      promoter region

<400> SEQUENCE: 22
tgtattcatg gatccaatac ccctt                                       25
```

PROBIOTIC ARGINOLYTIC ORAL COMPOSITIONS AND METHODS OF MAKING AND USING PROBIOTIC ARGINOLYTIC ORAL COMPOSITIONS

CROSS-REFERENCE TO RELATED APPLICATIONS

This application is a continuation-in-part of U.S. patent application entitled "Probiotic Arginolytic Oral Compositions and Methods of Making and Using Probiotic Arginolytic Oral Compositions," having Ser. No. 14/767,181 filed on Aug. 11, 2015 and issued as U.S. Pat. No. 9,655,839 B2 on May 23, 2017, which is the 35 U.S.C. § 371 national stage application of PCT Application No. PCT/US2014/016139, filed Feb. 12, 2014, which claims priority to U.S. provisional application entitled, "Probiotic Oral Compositions and Methods of Using Probiotic Oral Compositions," having Ser. No. 61/764,579, filed on Feb. 14, 2013, all of which are entirely incorporated herein by reference.

STATEMENT REGARDING FEDERALLY SPONSORED RESEARCH OR DEVELOPMENT

This invention was made with government support under DE028832 and DE010362 awarded by The National Institutes of Health. The government has certain rights in the invention.

SEQUENCE LISTING

The instant application contains a sequence listing which has been submitted with the instant application via EFS-Web. The sequence listing file is named 222108_1121_ST25.txt, is 6 KB in size, and is incorporated herein by reference in its entirety.

BACKGROUND

Dental caries is the most prevalent infectious and chronic disease affecting humans, and is associated with costly treatment worldwide. The transition from dental health to dental caries is characterized by compositional and metabolic changes in the complex microbial communities of oral biofilms. Oral biofilms, often called dental plaque, constantly form and grow on all tooth surfaces. Although production of acid by the bacteria in oral biofilms is the direct cause of dental caries, it is noteworthy that increases in the proportions of aciduric organisms, such as the caries-associated *Streptococcus mutans*, appear to occur at the expense of species that are less acid tolerant (i.e. less "aciduric"). Of particular note, a subset of less aciduric organisms derives protection from plaque acidification by alkali generation, which shows a positive association with dental health.

One of the primary routes for alkali generation by oral bacteria is the arginine deiminase system (ADS), through which arginine is catabolized into ornithine, ammonia and $CO_2$, with the concomitant generation of ATP. Hence, the ADS serves key physiological functions in bacteria, providing protection from the deleterious effects of low pH and ATP for growth and maintenance. The ADS activity in oral biofilms can impact the ecology of oral microbial communities by moderating the pH through ammonia production.

A variety of bacteria that colonize the teeth and oral soft tissues and form oral biofilms express the ADS. An increased risk for dental caries has been associated with a reduced ability of oral biofilms to produce alkali from arginine via the arginine deiminase system (ADS). Specifically, plaque bacteria from caries-free subjects present higher levels of ADS activity when compared to plaque bacteria from caries-active subjects. Moreover, there is a high degree of variability in the rate of alkali production among individuals, in some cases greater than 1000-fold. A better understanding of the microbiological basis of inter-subject variation in ADS activity and methods for improving ADS activity for the improvement of oral health would be beneficial.

Other streptococcal species can also produce and secrete antimicrobial substances that suppress the growth of *S. mutans*, including hydrogen peroxide ($H_2O_2$). For example, *Streptococcus sanguinis* and *Streptococcus gordonii* produce sufficient amounts of $H_2O_2$ to inhibit growth of *S. mutans*, mainly via a pyruvate oxidase enzyme (Pox) encoded by the spxB gene. $H_2O_2$ production by *S. gordonii*, but not *S. sanguinis*, seems to be inversely correlated with carbohydrate availability. *S. oligofermentans* can also produce $H_2O_2$ from lactic acid through lactate oxidase (Lox) and less efficiently using L-amino acid oxidase enzymes (LAAO). Moreover, facultatively anaerobic lactic-acid bacteria, including commensal oral streptococci, were shown to have vigorous oxygen metabolism catalyzed by flavin-containing NADH oxidases, some of which yield $H_2O_2$ as an end product.

SUMMARY

Briefly described, embodiments of the present disclosure provide probiotic arginolytic oral compositions, methods of making probiotic arginolytic oral compositions, and methods of using probiotic arginolytic oral compositions to increase arginolytic activity in the oral cavity and/or to treat and/or prevent caries.

The present disclosure provides embodiments of methods of increasing the amount of ammonia-producing bacteria in the oral cavity of a host, the methods including administering to a host a probiotic oral composition including a mixture of isolated bacterial strains and a pharmaceutically acceptable oral carrier, where the mixture includes at least two different isolated arginolytic bacterial strains, each strain capable of producing ammonia via the arginine deiminase system (ADS) and each strain meeting at least one of the following criteria: expressing ADS activity in the absence of supplemental arginine, expressing ADS activity in the presence of glucose, expressing ADS activity in a non-acidic pH, expressing ADS activity under aerobic conditions, inhibiting the growth of at least one bacterial strain associated with dental caries, and resisting inhibition of growth by at least one bacterial strain associated with dental caries. In the methods of increasing the amount of ammonia-producing bacteria in the oral cavity of a host, the ability of the isolated arginolytic bacterial strain to express ADS activity under any of said criteria is determined with respect to an ADS activity level of *S. gordonii* DL1 under the same conditions, where an ADS activity level about the same or higher than the ADS activity of *S. gordonii* DL1 under the same conditions indicates the strain meets the criteria. In these methods, at least two of the criteria above are met by the mixture of bacterial strains, and these criteria are met at an ADS activity level greater than the ADS activity level of *S. gordonii* DL1 under the same conditions. Also, in these methods, the probiotic oral composition does not include *Streptococcus mutans*, and administration of the probiotic oral composition increases the amount of ammonia-producing bacteria in the oral cavity of the host over the amount of ammonia-producing bacterial in the oral cavity of the host prior to administration of the probiotic oral composition.

Embodiments of the present disclosure also include methods of increasing the amount of ammonia-producing bacteria in the oral cavity of a host, the method including administering to a host a probiotic oral composition including a mixture of isolated bacterial strains and a pharmaceutically acceptable oral carrier, where the mixture of isolated bacterial strains includes an isolated arginolytic bacterial strain Streptococcus A12 and at least one other isolated arginolytic bacterial strain capable of producing ammonia via the arginine deiminase system (ADS). In these embodiments, the at least one other isolated arginolytic bacterial strains meets at least one of the following criteria: expressing ADS activity in the absence of supplemental arginine, expressing ADS activity in the presence of glucose, expressing ADS activity in a non-acidic pH, expressing ADS activity under aerobic conditions, inhibiting the growth of at least one bacterial strain associated with dental caries, and resisting inhibition of growth by at least one bacterial strain associated with dental caries.

The present disclosure further provides methods of treatment including administering to a host a probiotic oral composition comprising an isolated arginolytic bacterial strain Streptococcus A12.

In embodiments, the present disclosure provides methods of preventing or reducing the incidence of dental caries to a host, methods of slowing or arresting the progression of dental caries lesions in a host, or a combination of these. The methods include administering to a host a probiotic oral composition including a mixture of isolated bacterial strains and a pharmaceutically acceptable oral carrier, where the mixture includes at least two different isolated arginolytic bacterial strains, each strain capable of producing ammonia via the arginine deiminase system (ADS) and each strain meeting at least one of the following criteria: expressing ADS activity in the absence of supplemental arginine, expressing ADS activity in the presence of glucose, expressing ADS activity in a non-acidic pH, expressing ADS activity under aerobic conditions, inhibiting the growth of at least one bacterial strain associated with dental caries, and resisting inhibition of growth by at least one bacterial strain associated with dental caries. In these methods, the ability of the isolated arginolytic bacterial strain to express ADS activity under any of the above criteria is determined with respect to an ADS activity level of *S. gordonii* DL1 under the same conditions, where an ADS activity level about the same or higher than the ADS activity of *S. gordonii* DL1 under the same conditions indicates the strain meets the criteria. Also in these methods, at least two of the criteria above are met by the mixture of bacterial strains, these criteria are met at an ADS activity level greater than the ADS activity level of *S. gordonii* DL1 under the same conditions, and the probiotic oral composition does not include *Streptococcus mutans*.

Further, the methods of the present disclosure also include methods of treating or preventing an oral disorder, the methods including administering to a host in need of treatment or prevention of an oral disorder a probiotic oral composition comprising an isolated arginolytic bacterial strain Streptococcus A12.

Other methods, compositions, plants, features, and advantages of the present disclosure will be or become apparent to one with skill in the art upon examination of the following drawings and detailed description. It is intended that all such additional compositions, methods, features, and advantages be included within this description, and be within the scope of the present disclosure.

BRIEF DESCRIPTION OF THE DRAWINGS

Further aspects of the present disclosure will be more readily appreciated upon review of the detailed description of its various embodiments, described below, when taken in conjunction with the accompanying drawings.

FIGS. 3A-3D are a series of bar graphs illustrating comparisons of the ADS activity levels of arginolytic isolates from caries-active and caries-free subjects grown under different environmental conditions: different sugars (FIG. 3A), different pH (FIG. 3B), the presence or absence of arginine (FIG. 2C), and aerobic vs. anaerobic conditions (FIG. 3D). Results represent the mean and standard deviations (error bars) of three independent experiments.

In FIG. 6A arginolytic strains were inoculated first followed by inoculation of *S. mutans* UA159 24 h later, and in FIG. 6B arginolytic strains and UA159 were inoculated simultaneously FIGS. 7A-7E are graphs illustrating production of $H_2O_2$ by arginolytic strains: $H_2O_2$ produced during growth in different broth media (FIG. 7A), pyruvate oxidase activity (FIG. 7B), lactate oxidase activity (FIG. 7C), L-arginine oxidase activity (FIG. 7D), and NADH oxidase activity (FIG. 7E). (*) indicates statistically significant difference between the arginolytic strain and DL1 in a given growth condition ($p<0.05$).

FIGS. 8A-8C illustrate growth inhibition zones of *S. mutans* UA159 on arginolytic strains in diluted TY (TY-D-25 mM galactose) agar plates with or without 20 mM arginine. Mean average of inhibition zones±standard deviation (millimeter). (FIG. 8A) aerobic growth condition, (FIG. 8B) anaerobic growth condition, and (FIG. 8C) growth inhibition zones in anaerobic growth condition. Statistically significant differences between growth conditions within the same strain is shown as () $p<0.01$ or (*) $p<0.001$.

FIG. 10B is a bar graph illustrating that $H_2O_2$ production by S. gordonii or A12 is dependent on carbohydrate source and nutrient availability. Cells were grown in aerobic conditions in the indicated medium, and the concentration of $H_2O_2$ in the supernates was measured as described in the methods section. Asterisks indicate statistical significance between growth on glucose versus galactose in each organism, alpha=0.05. FIG. 10C is a bar graph illustrating a comparison of pyruvate, lactate, L-amino acid (LAAO) and NADH oxidase enzyme levels in S. gordonii DL1 and A12 (See text for methodology). Pyruvate oxidase (Pox) activity was the dominant $H_2O_2$-producing oxidase measured in both organisms under the conditions tested, and A12 produce significantly higher levels of Pox enzyme activity than S. gordonii. The asterisk signifies statistical significance between pyruvate oxidase levels in A12 and S. gordonii.

DESCRIPTION

Figure 1:
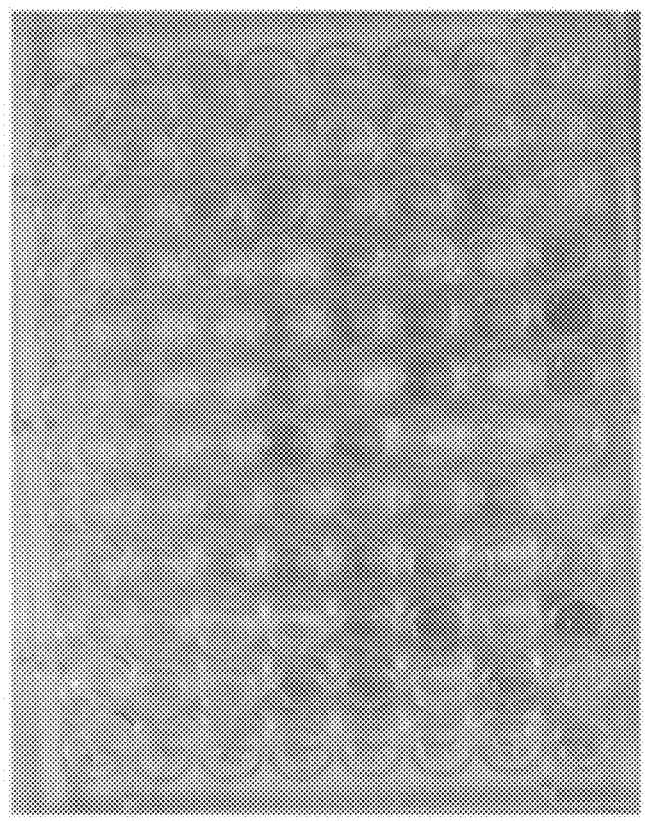
FIG. 1 illustrates a digital image of a screening of ADS-positive bacterial strains from dental plaque. ADS-positive phenotype is revealed by yellow-orange color when the Nessler's reagent detects the ammonia generated.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

Any publications and patents cited in this specification that are incorporated by reference are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, dentistry, biology, microbiology, statistics, biochemistry, molecular biology, pharmacology, and the like, which are within the skill of the art. Such techniques are explained fully in the literature.

It must be noted that, as used in the specification and the appended embodiments, the singular forms "a," "an," and "the" include plural referents unless the context clearly dictates otherwise. Thus, for example, reference to "a cell" includes a plurality of cells. In this specification and in the embodiments that follow, reference will be made to a number of terms that shall be defined to have the following meanings unless a contrary intention is apparent.

Prior to describing the various embodiments, the following definitions are provided and should be used unless otherwise indicated.

Definitions

In describing the disclosed subject matter, the following terminology will be used in accordance with the definitions set forth below.

The term "nucleic acid" as used herein refers to any natural and synthetic linear and sequential arrays of nucleotides and nucleosides, for example cDNA, genomic DNA, mRNA, tRNA, oligonucleotides, oligonucleosides and derivatives thereof. For ease of discussion, such nucleic acids may be collectively referred to herein as "constructs," "plasmids," or "vectors." Representative examples of the nucleic acids of the present disclosure include bacterial plasmid vectors including expression, cloning, cosmid and transformation vectors such as, but not limited to, pBR322, animal viral vectors such as, but not limited to, modified adenovirus, influenza virus, polio virus, pox virus, retrovirus, insect viruses (baculovirus), and the like, vectors derived from bacteriophage nucleic acid, and synthetic oligonucleotides like chemically synthesized DNA or RNA. The term "nucleic acid" further includes modified or derivatized nucleotides and nucleosides such as, but not limited to, halogenated nucleotides such as, but not only, 5-bromouracil, and derivatized nucleotides such as biotin-labeled nucleotides.

The term "isolated nucleic acid" refers to a nucleic acid with a structure (a) not identical to that of any naturally occurring nucleic acid or (b) not identical to that of any fragment of a naturally occurring genomic nucleic acid spanning more than three separate genes, and includes DNA, RNA, or derivatives or variants thereof. The term covers, for example but not limited to, (a) a DNA which has the sequence of part of a naturally occurring genomic molecule but is not flanked by at least one of the coding sequences that flank that part of the molecule in the genome of the species in which it naturally occurs; (b) a nucleic acid incorporated into a vector or into the genomic nucleic acid of a prokaryote or eukaryote in a manner such that the resulting molecule is not identical to any vector or naturally occurring genomic DNA; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, e.g., a gene encoding a fusion protein, and (e) a recombinant nucleotide sequence that is part of a hybrid sequence that is not naturally occurring. Isolated nucleic acid molecules of the present disclosure can include, for example, natural allelic variants as well as nucleic acid molecules modified by nucleotide deletions, insertions, inversions, or substitutions.

It is advantageous for some purposes that a nucleotide sequence is in purified form. The term "purified" in reference to nucleic acid represents that the sequence has increased purity relative to the natural environment.

The terms "polynucleotide," "oligonucleotide," and "nucleic acid sequence" are used interchangeably herein and include, but are not limited to, coding sequences (polynucleotide(s) or nucleic acid sequence(s) which are transcribed and translated into polypeptide in vitro or in vivo when placed under the control of appropriate regulatory or control sequences); control sequences (e.g., translational start and stop codons, promoter sequences, ribosome binding sites, polyadenylation signals, transcription factor binding sites, transcription termination sequences, upstream and downstream regulatory domains, enhancers, silencers, and the like); and regulatory sequences (DNA sequences to which a transcription factor(s) binds and alters the activity of a gene's promoter either positively (induction) or negatively (repression)). No limitation as to length or to synthetic origin is suggested by the terms described herein.

The terms "polypeptide" and "protein" as used herein refer to a polymer of amino acids of three or more amino acids in a serial array, linked through peptide bonds. The term "polypeptide" includes proteins, protein fragments, protein analogues, oligopeptides and the like. The term "polypeptides" contemplates polypeptides as defined above that are encoded by nucleic acids, produced through recombinant technology (isolated from an appropriate source such as a bird), or synthesized. The term "polypeptides" further contemplates polypeptides as defined above that include chemically modified amino acids or amino acids covalently or non-covalently linked to labeling ligands.

The term "fragment" as used herein to refer to a nucleic acid (e.g., cDNA) refers to an isolated portion of the subject nucleic acid constructed artificially (e.g., by chemical synthesis) or by cleaving a natural product into multiple pieces, using restriction endonucleases or mechanical shearing, or a portion of a nucleic acid synthesized by PCR, DNA polymerase or any other polymerizing technique well known in the art, or expressed in a host cell by recombinant nucleic acid technology well known to one of skill in the art. The term "fragment" as used herein may also refer to an isolated portion of a polypeptide, wherein the portion of the polypeptide is cleaved from a naturally occurring polypeptide by proteolytic cleavage by at least one protease, or is a portion of the naturally occurring polypeptide synthesized by chemical methods well known to one of skill in the art.

The term "gene" or "genes" as used herein refers to nucleic acid sequences (including both RNA and/or DNA) that encode genetic information for the synthesis of a whole RNA, a whole protein, or any portion of such whole RNA or whole protein. Genes that are not naturally part of a particular organism's genome are referred to as "foreign genes," "heterologous genes" or "exogenous genes" and genes that are naturally a part of a particular organism's genome are referred to as "endogenous genes". The term "gene product" refers to RNAs or proteins that are encoded by the gene. "Foreign gene products" are RNA or proteins encoded by "foreign genes" and "endogenous gene products" are RNA or proteins encoded by endogenous genes. "Heterologous gene products" are RNAs or proteins encoded by "foreign, heterologous or exogenous genes" and are, therefore, not naturally expressed in the cell.

As used herein the term "microbiome" refers to the living environment of microorganisms within a host organism. As used herein, "microbiome" generally refers to the community of microorganisms (e.g., bacteria) living within a host organism, such as within the oral cavity of a host organism. The term "microflora" similarly refers to the collective organisms living within the microbiome, the terms may be used interchangeably in the present disclosure. The term native microbiome also refers to the bacterial community of a host that has not been altered by (or prior to alteration by) the administration of drugs (e.g., antibiotics or probiotics) or procedures intended to alter the composition of the native bacterial colony. The native bacterial community of a host can change over time due to various natural and synthetic causes (e.g., illness, changes in diet, drugs, medical procedures, and the like).

The terms "taxonomic category" or "taxonomic classification" or "classification" as used herein refers to the categorization of organisms into the scientifically established taxonomic categories into which they have been assigned (e.g., kingdom, phylum, class, order, family, genus, species, strain), or, in the case of previously unidentified organisms, the category to which they would likely be assigned according to established scientific procedures based on similarity of genetics or characteristics. The "taxonomic category" may be a broad category (e.g., phylum, class) or a narrower category (e.g., genus, species), and the act of classification may involve multiple organisms or only one. "Classification" may also involve the act of grouping individuals into categories based on like characteristics, but generally, in the present disclosure "classification" refers to taxonomic classification" unless the context indicates otherwise.

A "strain" as used herein refers to a taxonomic sub-grouping within the species level, where a strain is a genetic variant or sub-type within a species. In the present disclosure a "strain" may refer to a clinical isolate that has close sequence identity (e.g., about 95% sequence identify, about 99% sequence identity, etc.) to a known species, but that may differ in one or more characteristics, such as, but not limited to, ADS activity level in certain environmental conditions.

An "isolated bacterial strain" or "bacterial isolate" refers to a bacterial strain or culture that has been produced from a bacterial organism that was isolated from a natural, heterogeneous environment (e.g., a host oral cavity) or population of microorganisms and separated via known microbiological techniques from the community of other microorganisms in its environment of origin. The isolated strain may then be grown in culture. An isolated bacterial strain or culture of the isolated bacterial strain is not necessarily free of all possible impurities, but it is a substantially homogenous culture of the bacterial isolate and can be distinguished from a naturally occurring, heterogeneous group of microorganisms.

As used herein, a "probiotic bacterium" refers to a bacterium that is generally regarded by the medical community as non-pathogenic and that confers a health benefit to the host. For instance, a bacterium that appears to have high ADS activity and thus promote an oral environment with reduced incidence of caries and that is not toxic to the host would be a non-limiting example of probiotic bacterium in the present disclosure.

As used herein "ADS activity" refers to the ability of a bacterial strain to produce alkali in the form of ammonia via the arginine deiminase system (ADS). The "ADS activity level" refers to the amount of ammonia a bacterial strain can produce via the ADS system. In embodiments, the ADS activity level is determined as nmol of citrulline generated (minute×mg protein)$^{-1}$. "Expressing ADS activity" or "expressing sufficient ADS activity" refers to the ability of some bacterial strains to metabolize arginine via the ADS at standard growth conditions or at growth under one or more adverse environmental factors, such as, but not limited to, non-acidic pH, low environmental arginine, high carbohydrate conditions (e.g., in presence of glucose), or aerobic conditions (e.g., the presence of oxygen). In embodiments, the ability of a strain to express ADS activity is determined with respect to the ADS activity of a known, well-characterized ADS-positive strain (e.g., *S. gordonii* DL1) under the same environmental assay conditions (e.g., under "standard growth conditions" or some other variation of growth conditions). In embodiments, if the strain expresses about the same activity, a greater activity, or a set percentage of ADS activity with respect to *S. gordonii* DL1, under the same assay conditions, the strain "expresses sufficient ADS activity". In other embodiments, the ability of a strain to express ADS activity under certain environmental conditions can be determined with respect to the ADS activity of the same strain. In some such embodiments, a strain is said to "express ADS activity" under the environmental assay conditions if it has a certain percentage of ADS activity (e.g., at least about 25% ADS activity, at least about 40% ADS activity, at least about 50% ADS activity, at least about 75% ADS activity, etc.) as compared to the ADS activity of that strain under standard growth conditions. In the present disclosure, "standard growth conditions", is a TY medium (tryptone-yeast extract broth) containing 25 mM galactose and 10 mM supplemental arginine at 5% $CO_2$, at 37° C. to an optical density at OD600+0.5-06.

The terms "treat", "treating", and "treatment" are an approach for obtaining beneficial or desired clinical results. Specifically, beneficial or desired clinical results include, but are not limited to, alleviation of symptoms, diminishment of extent of disease, stabilization (e.g., not worsening) of disease, delaying, slowing, or arresting disease progression, substantially preventing spread of disease, reducing, amelioration or palliation of the disease state, and remission (partial or total) whether detectable or undetectable. In addition, "treat", "treating", and "treatment" can also be therapeutic in terms of a partial or complete cure for a disease and/or adverse effect attributable to the disease. With respect to caries, "treating" includes reducing the appearance of dental caries lesions and slowing or arresting the progression of dental caries lesions (e.g., slowing or stopping the growth or severity of the lesions). "Treating" also includes "preventing"/"prophylactically treating." As used herein, the terms "prevent", "prophylactically treat," or "prophylactically treating" refers to completely, substantially, or partially preventing a disease/condition or one or more symptoms thereof in a host. Similarly, "delaying the onset of a condition" can also be included in "prophylactically treating", and refers to the act of increasing the time before the actual onset of a condition in a patient that is predisposed to the condition. With respect to caries, "preventing" or "prophylactic treatment" can include preventing the appearance of new caries lesions in a host.

By "administration" is meant introducing a compound of the present disclosure into a subject; it may also refer to the act of providing a composition of the present disclosure to a subject (e.g., by prescribing). The preferred route of administration of the compositions of the present disclosure is oral. However, any route of administration that will assist the composition to treat the oral condition of the host can be used.

The term "organism," "subject," or "host" refers to any living entity in need of treatment, including humans, mammals (e.g., cats, dogs, horses, chicken, pigs, hogs, cows, and other cattle), and other living species that are in need of treatment. In particular, the term "host" includes humans. As used herein, the term "human host" or "human subject" is generally used to refer to human hosts. In the present disclosure the term "host" typically refers to a human host, so when used alone in the present disclosure, the word "host" refers to a human host unless the context clearly indicates the intent to indicate a non-human host. Hosts that are "predisposed to" condition(s) can be defined as hosts that do not exhibit overt symptoms of one or more of these conditions but that are genetically, physiologically, or otherwise at risk of developing one or more of these conditions.

As used herein, the following terms have the meanings ascribed to them unless specified otherwise. In this disclosure, "consisting essentially of" or "consists essentially" or the like, when applied to methods and compositions encompassed by the present disclosure, refers to compositions like those disclosed herein but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments. Specifically, with respect to mixtures of arginolytic bacterial strains of the present disclosure, "consisting essentially of" indicates that minor amounts of other bacterial strains other than those with the criteria listed may be present in minor amounts, but that they do not affect the overall function of the mixture and do not affect the arginolytic activity of the mixture.

Discussion

The embodiments of the present disclosure encompass probiotic, arginolytic oral compositions, methods of making a mixture of arginolytic bacterial strains for oral use, methods and compositions for treating and/or preventing dental caries and slowing and/or arresting the progression of caries lesions in a patient, and methods and compositions for increasing the amount of arginolytic bacteria in the oral cavity of a host and increasing ammonia production in the oral cavity of a host. Embodiments of the present disclosure include compositions including a mixture of arginolytic bacterial strains. In embodiments, the compositions are probiotic oral compositions.

Evidence continues to accumulate from in vitro and clinical observations that support the role of alkali generation in oral ecology and inhibition of dental caries (Dawes and Dibdin, 2001; Margolis et al., 1988b; Nascimento et al., 2009a; Peterson et al., 1985; Shu et al., 2007a; Wijeyeweera and Kleinberg, 1989a). A positive correlation between oral arginine metabolism and absence of caries activity has been clinically demonstrated in adults (Nascimento et al., 2009a), and more recently in children (Nascimento et al., 2012). Specifically, oral bacteria from dental plaque of caries-free subjects presents higher ADS activity compared with those from caries-active subjects. There is also a high degree of variability in the rate of ammonia production among individuals, in some cases greater than 1000-fold. Previous studies using laboratory strains of oral streptococci indicate that the expression of ADS genes is substrate inducible, sensitive to carbon catabolite repression (CCR), and thrives low pH and anaerobic conditions. Specific and global transcriptional regulators, multiple two-component systems (TCS) and other factors have been shown to regulate ADS activity through transcriptional and post-transcriptional mechanisms (Burne, 1991; Dong et al., 2004; Liu and Burne, 2009; Liu et al., 2008). An in vitro study showed that as little as a five-fold decrease in the ammonia-generating capacity of a genetically-modified strain of the caries pathogen *Streptococcus mutans* resulted in the loss of ability to offset environmental acidification by glycolysis (Clancy et al., 2000). Therefore, many individuals may lack sufficient ADS activity to neutralize dental plaque during fasting periods or following a cariogenic challenge. Thus, the ADS activity of plaque bacteria can impact the pH profiles of resting and carbohydrate-challenged plaque, and therefore, the risk for caries development.

Differences in the microbial composition of oral biofilms and differential expression of the ADS are the most likely factors that affect the capacity of oral samples from different individuals to metabolize arginine. The use of qPCR in a previous clinical study (Nascimento et al., 2009a) did not reveal a statistically significant association between the proportions of two recognized arginolytic species, *S. sanguinis* and *S. gordonii* and the caries-status of adults. These results suggested that the diminution in ADS activity associated with caries experience may not be due simply to lower proportions of known ADS-positive bacteria, and also raised the possibility that species other than those examined may contribute to overall oral ADS activity. It is also possible that environmental conditions and host factors encourage differential expression of the ADS in caries-active versus caries-free subjects. Thus, in the present disclosure, the organisms that contribute to arginolysis in the oral cavity were more thoroughly characterized and studied. Providing new insight into the fundamental microbiology and ecology of oral arginolytic bacterial communities and their relationship to dental health and dental caries, the examples below demonstrate isolation and characterization of arginolytic bacterial strains from supragingival dental plaque of caries-free and caries-active adult subjects, and the responses of these isolates to environmental stimuli.

As discussed briefly above and in greater detail below, some bacteria have the ability to produce ammonia via the arginine deiminase system (ADS). Such "arginolytic" bacteria, when found in a host (particularly the oral cavity of a host) can be beneficial in increasing ammonia production in the oral cavity of a host, thereby providing an environmental factor for reducing the incidence of caries. Some such bacterial strains are found more prevalently in the oral biofilms of caries-free individuals. As described below, the studies in the examples identified various bacterial strains capable of ADS activity and described methods for identification of various strains capable of ADS activity. Additionally, the studies described in the examples below further identified and described how to identify bacterial strains capable of maintaining ADS activity in the presence of conditions traditionally associated with a reduction in ADS activity. Many such conditions are also associated with higher incidence of caries. Thus, the ability to identify strains meeting certain criteria and expressing ADS activity in the presence of certain conditions is beneficial for increasing the level of these bacteria in a host and for methods of treating, preventing, slowing, or arresting the incidence of caries in a patient. In embodiments, some strains identified as having ADS activity and expressing ADS activity under certain conditions can be included in a probiotic oral composition. Such compositions can be used in embodiments of methods of the present disclosure to increase the amount of ammonia-producing bacteria in the oral cavity of a host, methods to treat or prevent caries, and/or methods to slow or arrest the progression of caries lesions in a patient with dental caries.

Probiotic Oral Compositions:

The present disclosure thus provides probiotic oral compositions including a mixture of bacterial strains, where the mixture includes at least two different isolated arginolytic bacterial strains. Each of the at least two isolated arginolytic bacterial strains in the mixture is capable of producing ammonia via the arginine deiminase system (ADS), and each strain meets at least one ADS-related criteria. In embodiments the ADS-related criteria include, but are not limited to, the following: expressing ADS activity in the absence of supplemental arginine (where "supplemental arginine" is arginine (in addition to arginine naturally present in the growth medium), (e.g., greater than about 5 mM of arginine) added to the base growth medium), expressing ADS activity in the presence of glucose (e.g., addition of glucose to base growth medium), expressing ADS activity in a non-acidic pH (e.g., pH of at least about 7), expressing ADS activity under aerobic conditions (e.g., in the presence of additional oxygen), inhibiting the growth of at least one bacterial strain associated with dental caries, and resisting inhibition of growth by at least one bacterial strain associated with dental caries. In embodiments of the probiotic oral compositions of the present disclosure, at least two of the above criteria are met by the mixture of bacterial strains, and each bacterial strain in the mixture may meet more than one of the criteria.

As most bacterial species associated with dental carries are not arginolytic, there will likely not be much overlap between such species. However, for clarification, in embodiments, the mixture of isolated arginolytic bacterial strains specifically excludes any strains of bacteria from a bacterial species associated with dental caries (e.g., $S.$ $mutans$ and the like). In embodiments of the compositions of the oral compositions of the present disclosure, the mixture consists of at least two different isolated arginolytic bacterial strains, with each strain capable of producing ammonia via the ADS and each strain meeting at least one of the criteria listed above.

The probiotic compositions of the present disclosure also can include a pharmaceutically acceptable oral carrier, such as, but not limited to, water, other pharmaceutically acceptable liquids, gels, powders, and the like. The compositions can be formulated into oral formulations such as, but not limited to, liquid mouth rinses, oral sprays, gels, pastes (e.g., toothpaste), certain foodstuffs, candies/mints, gum, or chewable tablets, and the like. Methods of producing such formulations are known to those of skill in the art of pharmacology and/or compounding.

In embodiments the bacterial strains for the mixture can be selected from any ADS positive bacterial strain identified or capable of identification by the methods of the present disclosure described below that show ADS activity. In embodiments arginolytic bacterial strains can be selected from strains, such as, but not limited to those identified in Tables 1 and 2 below that show ADS activity. In embodiments, the ADS activity is at least about 225 units (mg protein)$^{-1}$, at least about 250 units (mg protein)$^{-1}$, at least about 275 units (mg protein)$^{-1}$, at least about 300 units (mg protein)$^{-1}$, and so on, as measured by ADS assays under standard growth conditions, such as the ADS assay described below in Example 1. Briefly, an embodiment of an ADS assay includes measuring activity by monitoring citrulline production from arginine, as described in Example 1, below. Cells are harvested by centrifugation, washed with 10 mM Tris-maleate buffer (pH 6.8) and resuspended using $\frac{1}{10}$ the original culture volume in the same buffer. The cells were permeabilized by vortexing them with toluene and were collected by centrifugation at 18,000×g. The supernatant fluid was discarded and the pellet resuspended in 10 mM Tris-maleate buffer and used to measure AD activity in a reaction mixture containing 20 nM arginine, 10 mM hexanoic acid, and 50 mM Tris-maleate buffer (pH 6.0). The concentration of protein used in each assay was determined as described in Example 1.

In some embodiments, the ADS activity of the isolated arginolytic bacterial strains in the mixture is at least about the same as the ADS activity of the well-characterized lab strain $Streptococcus$ $gordonii$ DL1 ($Streptococcus$ $gordonii$ (strain Challis/ATCC 35105/CH1DL1/V288)) under standard growth conditions. In some embodiments the ADS activity is at least about 300 nmol of citrulline (minute×(mg of protein))$^{-1}$ (see table 1: ADS activity of $S.$ $gordonii$ DL1 of about 339.3+/−33.0) under standard growth conditions. In some embodiments, the bacterial strains for the mixture have an ADS activity of about 50% to about 100% of the activity of $S.$ $gordonii$ DL1 under standard growth conditions. In some embodiments the ADS activity of the bacterial strain is less than that of $S.$ $gordonii$ under standard growth conditions but is greater than the ADS activity of $S.$ $gordonii$ under other environmental conditions, as described in more detail below. In embodiments, the ADS activity of at least one of the isolated arginolytic bacterial strains in the mixture is greater than the ADS activity of *S. gordonii* DL1 under at least one of the conditions set forth above for the ADS-related criteria. In some embodiments, the ADS activity of at least two of the isolated arginolytic bacterial strains in the mixture is greater than the ADS activity of *S. gordonii* DL1 under at least one of the conditions set forth above for the ADS-related criteria, and in some embodiments, the ADS activity of each of the isolated arginolytic bacterial strains in the mixture is greater than the ADS activity of *S. gordonii* DL1 under at least one of the conditions set forth above for the ADS-related criteria. In other words, even if the strain had a lower ADS activity than *S. gordonii* DL1 under standard growth conditions, it has greater ADS activity under one of the conditions set forth above (e.g., in the absence of supplemental arginine, in a non-acidic pH environment, in the presence of glucose, in aerobic conditions, in the presence of at least one bacterial strain associated with dental caries.)

In some embodiments of the probiotic oral composition of the present disclosure, the bacterial strains are selected from arginolytic strains of bacteria from the species including, but not limited to, *Streptococcus* parasanguinis, *Streptococcus intermedius*, *Streptococcus gordonii*, *Streptococcus australis*, *Streptococcus sanguinis*, and *Streptococcus cristatus*. In embodiments, the bacterial strains are selected from arginolytic strains with sequence similarity of at least 99% to the following strains: *Streptococcus parasanguinis* PTO10 (Accession No. GU561390.1), *Streptococcus intermedius* C270 (Accession No. CP003858.1), *Streptococcus gordonii* str. Challis sbustr. CH1 (Accession No. AB690250.1), *S. gordonii* str. Challis sbustr. CH1 (Accession No. NR_074516.1), *S. gordonii* ATCC 10558 (Accession No. AY485606.1), *Streptococcus australis* A1-1 (Accession No. JX861483.1), *Streptococcus sanguinis* JCM 5708 (Accession NO. AB596946.1), and *Streptococcus cristatus* F0329 (Accession No. AY005047.1). It should be noted that for some of these clinical isolates set forth above and below in Tables 1 and 2, the species designations were given based on closest 16S rRNA match, but such isolates could later be classified as different species based on additional genomic analysis. For instance, the isolate A12 was indicated in Example 1 as *Streptococcus australis* A12, but further genomic analysis may indicate possible classification in a different species. Thus, for clarity, the strain A12 may be referred to as *Streptococcus australis* A12 in a few instances, but will generally be referred to simply as *Streptococcus* A12. A deposit of *Streptococcus* A12 was made on Mar. 9, 2017 with the American Type Culture Collection (ATCC®) under ATCC patent deposit designation PTA-123884.

In some embodiments the probiotic oral compositions include at least one bacterial strain selected from the following strains identified in Table 1 (Example 1), below: *Streptococcus* parasanguinis A1, *Streptococcus intermedius* A2, *S. intermedius* A3, *S. intermedius* A5, *Streptococcus gordonii* A7, *S. gordonii* A8, *S. gordonii* A9, *S. gordonii* A10, *S. gordonii* A11, *Streptococcus* A12, *S. australis* A13, *Streptococcus sanguinis* A41, and *Streptococcus cristatus* A55. In embodiments of the compositions of the present disclosure, at least one of the isolated arginolytic bacterial strains is *Streptococcus* A12.

In embodiments, at least one strain in the mixture expresses ADS activity in the presence of glucose (e.g., glucose (e.g., about 25 mM glucose) instead of galactose in the growth medium). In embodiments, bacterial strains that express ADS activity in the presence of glucose that are selected for the mixture have at least about the level of ADS activity as *S. gordonii* DL1, or greater, under the same glucose conditions, or, at least about 50%, at least about 75%, at least about 90%, at least about 100% of the ADS activity of *S. gordonii* under the same glucose conditions. In some embodiments, at least one strain in the mixture that expresses ADS activity under added glucose conditions (e.g., 25 mM glucose instead of galactose added to growth medium) has at least about 25% of the ADS activity of the same strain under standard growth conditions. In embodiments, the strain that expresses ADS activity under added glucose conditions has at least about 40%, at least about 50%, at least about 75%, and so on, of the ADS activity of the same strain under standard growth conditions. In embodiments, the strains expressing ADS activity in the presence of glucose are selected from strains from bacterial species including, but not limited to: *Streptococcus parasanguinis, Streptococcus intermedius, Streptococcus gordonii,* and *Streptococcus australis*. In embodiments, the bacterial strains are selected from arginolytic strains with sequence similarity of at least 99% to the following strains: *Streptococcus* parasanguinis PTO10 (Accession No. GU561390.1), *Streptococcus intermedius* C270 (Accession No. CP003858.1), *Streptococcus gordonii* str. Challis sbustr. CH1 (Accession No. AB690250.1), *S. gordonii* str. Challis sbustr. CH1 (Accession No. NR_074516.1), *S. gordonii* ATCC 10558 (Accession No. AY485606.1), and *Streptococcus australis* A1-1 (Accession No. JX861483.1). Some representative bacterial strains express ADS activity of greater than DL1 (e.g., ADS>about 52.5 units) in the presence of glucose include but are not limited to the following strains: *S. parasanguinis* A1, *S. intermedius* A2, *S. intermedius* A3, *S. intermedius* A5, *S. gordonii* A7, *S. gordonii* A8, *S. gordonii* A9, *S. gordonii* A10, *S. gordonii* A11, *Streptococcus* A12, and *S. australis* A13.

In embodiments, at least one strain in the mixture expresses ADS activity in a non-acidic pH (e.g., pH at least about 7). In embodiments, bacterial strains that express ADS activity in a non-acidic pH that are selected for the mixture have at least about the level of ADS activity as *S. gordonii* DL1, or greater, under the same pH conditions, or at least about 75% of the ADS activity as *S. gordonii* DL1 under the same pH conditions. In embodiments, the bacterial strains have at least about 50% of the ADS activity as *S. gordonii* DL1 under the same pH conditions. In some embodiments, at least one strain in the mixture that expresses ADS activity in a non-acidic pH has at least about 50% of the ADS activity of the same strain under standard growth conditions, or under an acidic pH of about 5.7. In embodiments, the strain that expresses ADS activity under a non-acidic glucose conditions has at least about 40%, at least about 50%, at least about 75%, and so on, of the ADS activity of the same strain under standard growth conditions, and/or with an acidic pH of about 5.7. In embodiments, the strains expressing ADS activity in non-acidic pH are selected from strains from bacterial species including, but not limited to: *Streptococcus parasanguinis, Streptococcus intermedius, Streptococcus gordonii,* and *Streptococcus australis*. In embodiments, the bacterial strains are selected from arginolytic strains with sequence similarity of at least 99% to the following strains: *Streptococcus parasanguinis* PTO10 (Accession No. GU561390.1), *Streptococcus intermedius* C270 (Accession No. CP003858.1), *Streptococcus gordonii* str. Challis sbustr. CH1 (Accession No. NR_074516.1), and *Streptococcus australis* AI-1 (Accession No. JX861483.1). Some representative bacterial strains that express ADS activity of greater than DL1: (ADS>about 344.5 units) in a non-acidic pH include, but are not limited to the following strains: *S. parasanguinis* A1, *S. intermedius* A2, *S. intermedius* A3, *S. gordonii* A8, and *Streptococcus* A12.

In embodiments, at least one strain in the mixture expresses ADS activity in the absence of supplemental arginine (e.g., less than about 5 mM arginine added to the growth medium). In embodiments, bacterial strains that express ADS activity in the absence of supplemental arginine have at least the level of ADS activity as *S. gordonii* DL1, or greater, under the same arginine-deficient conditions, or have at least 40%, at least 50%, at least 75%, and so on, of ADS activity as *S. gordonii* DL1 under the same arginine-deficient conditions. In embodiments, the strain that expresses ADS activity in the absence of supplemental arginine has at least about 60% of the ADS activity of the same strain under standard growth conditions. In embodiments, the strain that expresses ADS activity in the absence of supplemental arginine conditions has at least about 40%, at least about 50%, at least about 75%, and so on, of the ADS activity of the same strain under standard growth conditions. In embodiments, the strains expressing ADS activity in the absence of supplemental arginine are selected from strains from bacterial species including, but not limited to: *Streptococcus* parasanguinis, *Streptococcus intermedius*, *Streptococcus gordonii*, and *Streptococcus australis*. In embodiments, the bacterial strains are selected from arginolytic strains with sequence similarity of at least 99% to the following strains: *Streptococcus* parasanguinis PTO10 (Accession No. GU561390.1), *Streptococcus intermedius* C270 (Accession No. CP003858.1), *Streptococcus gordonii* str. Challis sbustr. CH1 (Accession No. NR_074516.1), and *Streptococcus australis* A1-1 (Accession No. JX861483.1). Some representative strains that express ADS activity greater than DL1 (ADS>about 232.5 units) in the absence of supplemental arginine include, but are not necessarily limited to the following: *S. parasanguinis* A1, *S. intermedius* A2, *S. intermedius* A3, *S. gordonii* A8, *Streptococcus* A12, and *S. australis* A13.

In embodiments, at least one strain in the mixture expresses ADS activity in aerobic conditions (e.g., in the presence of O$_2$, e.g., aeration induced by agitation, such as by a rotary shaker.). In embodiments, bacterial strains that express ADS activity in aerobic conditions have at least the level of ADS activity as *S. gordonii* DL1, or greater, under the same oxygenation, or have at least 60%, 75%, 90%, and so on of the ADS activity of *S. gordonii* DL1 under the same oxygenation. In embodiments strains expressing ADS activity in aerobic conditions have at least about 60% of the ADS activity of the same strain under standard growth conditions without aeration (e.g., in an anaerobic chamber). In embodiments, the strain that expresses ADS activity in aerobic conditions has at least about 40%, at least about 50%, at least about 75%, at least about 100% and so on, of the ADS activity of the same strain under standard growth conditions without aeration. In embodiments, the strains expressing ADS activity in aerobic conditions are selected from strains from bacterial species including, but not limited to: *Streptococcus parasanguinis, Streptococcus intermedius, Streptococcus gordonii, Streptococcus australis, Streptococcus sanguinis,* and *Streptococcus cristatus*. In embodiments, the bacterial strains are selected from arginolytic strains with sequence similarity of at least 99% to the following strains: *Streptococcus parasanguinis* PTO10 (Accession No. GU561390.1), *Streptococcus intermedius* C270 (Accession No. CP003858.1), *S. gordonii* str. Challis sbustr. CH1 (Accession No. NR_074516.1), *Streptococcus australis* A1-1 (Accession No. JX861483.1), *Streptococcus sanguinis* JCM 5708 (Accession NO. AB596946.1), and *Streptococcus cristatus* F0329 (Accession No. AY005047.1). Representative bacterial strains that express ADS activity greater than DL1 (e.g., ADS>14.4 units) under aerobic conditions include, but are not limited to the following: *S. parasanguinis* A1, *S. intermedius* A2, *S. intermedius* A3, *S. intermedius* A5, *S. gordonii* A8, *Streptococcus* A12, *S. sanguinis* A41, and *S. cristatus* A55.

In embodiments of the probiotic oral composition of the present disclosure one or more of the isolated arginolytic bacterial strains in the mixture inhibits the growth of at least one bacterial strain associated with dental caries and/or resists inhibition of growth by at least one bacterial strain associated with dental caries. In embodiments of the probiotic oral composition of the present disclosure where a bacterial strain inhibits the growth of at least one bacterial strain associated with dental caries and/or resists inhibition of growth by at least one bacterial strain associated with dental caries, the bacterial strain associated with dental caries can be, but is not limited to, one or more strains of *Streptococcus mutans*. Other bacterial strains associated with dental caries include, but are not limited to, strains of *Streptococcus sobrinus*, various *Lactobacillus* species, certain *Scardovia* species and some *Actinomyces* species.

Since *Streptococcus* A12 has demonstrated the ability to maintain ADS activity in each of the ADS criteria set forth above, as well as to inhibit the growth of *S. mutans* and resist inhibition by *S. mutans*, in some embodiments the arginolytic probiotic oral composition of the present disclosure may include a mixture of isolated bacterial strains, where at least one of the strains is selected from *Streptococcus* A12. In embodiments, the arginolytic probiotic oral composition including *Streptococcus* A12 does not include any strains of bacteria from a bacterial species associated with dental caries (e.g., *S. mutans*). In some embodiments a composition for treatment of an oral disorder may include at least the isolated *Streptococcus* A12 strain.

In embodiments of the present disclosure, the probiotic composition may also include one or more compounds to increase the ADS activity of the bacterial strains. For instance, such additional compound may be a substance that can alter an aspect of the oral environment to make the environment more conducive to ADS activity. In embodiments, the one or more compounds to increase the ADS activity of the bacterial strains can include arginine and/or arginine-containing peptides and proteins (e.g. those derived from foodstuffs). In embodiments of the present disclosure, the probiotic composition includes arginine. It will be understood that since these compositions are to be administered orally to a host that the components should be pharmaceutically and biologically acceptable (e.g., generally recognized as safe, non-toxic, and the like).

Other components can be included in the oral probiotic compositions of the present disclosure to improve performance or other aspects of the composition (such as taste, smell, mouth feel, and the like). It will be understood that the bacterial strains included in embodiments of the compositions of the present disclosure are isolated strains and are not merely a samples obtained from a natural environment and placed directly in an oral composition.

Methods of Selecting Arginolytic Bacterial Strains for Oral Use:

The present disclosure also provides methods of identifying and selecting arginolytic bacterial strains and making mixtures of arginolytic bacterial strains for oral use in a host. In embodiments, the methods include obtaining a plurality of bacterial strains isolated from oral samples (e.g., samples taken from a host, such as a caries free host). From the plurality of bacterial strains, assays are conducted to identify and isolate arginolytic bacterial strains capable of producing ammonia via the arginine deiminase system (ADS). Embodiments of such methods are described in the examples below. After isolating and selecting the ADS positive strains, one or more additional assays can be conducted to identify arginolytic bacterial strains capable of expressing ADS activity in environmental conditions that are generally not conducive the arginine production in a host and/or that are conducive to caries. In embodiments, assays are used to mimic such environmental conditions for identification and selection of bacterial isolates that express ADS activity under such conditions. In embodiments, the environmental assay conditions include, but are not limited to, the absence of supplemental arginine, the presence of glucose, a non-acidic pH, aerobic conditions, and the presence of at least one bacterial strain associated with dental caries. In embodiments, the bacterial strain associated with dental caries is *S. mutans*. In embodiments, one or more assays for such conditions are carried out separately for strains of ADS-positive bacteria identified in the preceding step. The method further includes, selecting at least two different isolated arginolytic bacterial strains identified in the environmental condition assay step and using the selected strains to prepare a mixture of arginolytic bacterial that expresses ADS activity in at least two of the selected environmental conditions.

The ADS activity for the strains and the ability of the strain to express ADS activity under various conditions is determined as set forth above (e.g., with respect to a certain % of the ADS activity of the same strain under standard growth conditions and/or with respect to the ADS activity of the lab strain *S. gordonii* DL1 under the same environmental conditions as the selected strain).

Once the strains are selected, various mixtures of strains with ADS activity under different environmental conditions can be prepared. Such mixtures can then be used to prepare probiotic oral compositions of the present disclosure described above. The mixtures can be combined with one or more compounds capable of increasing the ADS activity of the bacterial strains (e.g., arginine, galactose, acidic compounds, and the like).

Methods of Use

The compositions described above can be used in a number of ways to affect the oral environment of a host. In embodiments, the compositions can be used to increase the amount of ammonia-producing bacteria in the oral cavity of a host, to increase the ammonia production in the oral cavity of a host, to increase production of hydrogen peroxide in the oral cavity of a host, and/or to treat dental disorders (e.g., dental caries, periodontal disease, oral fungal disease, and the like) in patients, including both children and adults. As demonstrated in the examples below, the ADS-positive strains described above and used in the compositions of the present disclosure meet various criteria, such as retaining ADS activity in environments that normally suppress such activity, or in the presence of antagonizing bacterial strains, such as *S. mutans*. Many of the environments that typically suppress ADS activity and ADS-positive bacterial strains, such as low acid, high glucose, and aerobic conditions also encourage the growth of bacterial strains associated with dental caries (such as, but not limited to *S. mutans*). However, as discussed above and demonstrated in the examples, arginolytic bacterial isolates that retain ADS activity under such conditions and that suppress or resist suppression by *S. mutans* or other caries associated bacterial strains, can help to reverse these conditions, suppress *S. mutans*, and to treat disorders associated with such conditions. For instance, many ADS-positive strains produce ammonia and $H_2O_2$, which antagonizes *S. mutans* and other caries-associated bacteria. The production of $H_2O_2$ is also detrimental to periodontal pathogens, which are susceptible to reactive oxygen species. Other oral pathogens, such as oral fungal pathogens (including, but not limited to *Candida*) also proliferate in the absence of beneficial bacterial organisms, such as the arginolytic strains described here. Thus, treatment with compositions including such strains can also help in the treatment of these other oral disorders.

In embodiments, the methods can include use of compositions described above including mixtures of isolated bacterial strains, where at least two different strains are capable of producing ammonia via ADS and each strain meets at least one of the criteria set forth above. In some embodiments, the methods can include use of a probiotic oral composition including one or more isolated bacterial strains having ADS activity, where at least one of the strains is *Streptococcus* A12.

Embodiments include methods of treatment by administering to a host a probiotic oral composition including an isolated arginolytic bacterial strain *Streptococcus* A12. In embodiments, the *Streptococcus* A12 can be used alone in a probiotic oral composition for treating/preventing an oral disorder, preventing/reducing/slowing progression of dental caries, increasing ADS activity in the oral cavity of a host, increasing the amount of ammonia-producing bacteria in the oral cavity of a host, and the like, or the *Streptococcus* A12 can be combined with other probiotic bacterial strains, either arginolytic and/or non-arginolytic.

In embodiments, the compositions of the present disclosure can be administered to a host to increase the amount of ammonia-producing arginolytic bacteria in the oral cavity of the host. In embodiments, the composition may be administered during times when the oral environment of the host is least likely to be conducive to ADS activity in order to increase the potential for ADS activity and reduce potential for creating a caries-conducive environment. For instance, the compositions may be administered after a meal (e.g., a high-carbohydrate meal), or before sleep. In embodiments, administering the probiotic oral composition increases the amount of ammonia-producing bacteria to an amount greater than existed in the oral cavity of the host prior to administration of the composition. The increased amount of ammonia-producing bacteria may be sustained for only a short time period (e.g., a few hours), or it may persist for a longer period (e.g., several hours to days). The length of time may depend on the formulation of the composition (e.g., a mouth rinse or oral spray vs. a saliva-resistant gel or paste applied to the oral/dental surfaces or a long-lasting chewing gum or lozenge). Even if the higher level of ADS-producing bacterial persists for a relatively short time, with optimal timing, this should still be sufficient to provide benefits to a host in terms of providing a healthier oral environment to discourage caries growth.

In embodiments, the method of increasing the amount of ammonia-producing bacteria in the oral cavity of a host also increases the ammonia production in the oral cavity of the host, with respect to the amount of ammonia production prior to administration of the probiotic oral composition. Also, many ADS-producing bacterial strains have been shown (see Examples below) to produce hydrogen peroxide ($H_2O_2$), which antagonizes the growth strains, such as *S. mutans*, associated with dental caries and other dental disorders.

In other embodiments, the compositions can be administered to patients to help treat or prevent dental caries in a patient predisposed to dental caries, who has had a history of dental caries, or who has an active case of dental caries. In embodiments, the composition can be administered to a host with active dental caries to slow or arrest the progression of a caries lesion. In embodiments, the compositions can be administered to patients to help treat or prevent other oral disorders, such as, but not limited to, other disorders associated with oral pathogens that may proliferate in the absence of arginolytic and/or $H_2O_2$ producing bacterial species. In embodiments, the oral disorders can include, but are not limited to, caries, periodontal disease, oral fungal infections, and the like.

In embodiments of the present disclosure, the probiotic compositions may include or may be administered with one or more compounds to increase the ADS activity of the bacterial strains. For instance, such additional compound may be a substance that can alter an aspect of the oral environment to make the environment more conducive to ADS activity. In embodiments, the one or more compounds to increase the ADS activity of the bacterial strains can include arginine and/or arginine-containing peptides and proteins (e.g. those derived from foodstuffs). In embodiments of the present disclosure, the probiotic composition includes arginine. It will be understood that since these compositions are to be administered orally to a host that the components should be pharmaceutically and biologically acceptable (e.g., generally recognized as safe, non-toxic, and the like). In embodiments compounds such as arginine or other compounds to increase the ADS activity of the bacterial strains can be administered in same compounds as the probiotic compositions or at the same time (but not necessarily in the same formulation) as the probiotic compositions, or within a specified amount of time before or after the probiotic compositions (e.g., they can be administered in a separate "prebiotic" composition, such as toothpaste, gum, mouth rinse, lozenge, etc. that can be used by the patient before administration of the probiotic compositions of the present disclosure or at some other time near the time of administration of the probiotic compositions of the present disclosure).

The compositions of the present disclosure can be administered to patients according to a regimen determined by their dental care provider. In embodiments of the present disclosure, the composition may be administered in a single dose or it may be administered on a regular repeating schedule. In some embodiments, the composition may be administered during regular dental visits, such as when being used for prevention. In yet other embodiments, the composition may be provided to a patient in the form of a self-administered oral formulation for administration on a regular basis for a period of time, such as daily, weekly, or some other regular schedule for a period of time such as a number of weeks, months, and so on. In some embodiments, such a regimen may be implemented for a patient with active caries, a history of caries, or considered at-risk for caries development. The amount, timing, and dosing of the compositions of the present disclosure can be determined for each patient by their dental health provider or by recommendation of a dental health association or guidelines.

Additional details regarding the tests and methods of the present disclosure are provided in the Examples below. The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following embodiments.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Characterization of the Arginolytic Microflora of Human Oral Biofilms

The present example describes the isolation and characterization of arginolytic bacterial species from caries-free and caries-active subjects. A selected group of oral bacteria commonly associated with dental health is capable of producing alkali in the form of ammonia via the arginine deiminase system (ADS), which has a profound impact on the pH of human oral biofilms. An increased risk for dental caries has been associated with reduced ADS activity of the bacteria in oral biofilms. In this example, arginolytic bacterial strains from dental plaque samples of caries-free (CF) and caries-active (CA) adults were isolated and characterized to study the basis for differences in plaque ADS activity between individuals. Fifty ADS-positive bacterial strains were identified by 16S rRNA gene sequencing, and their ADS activity levels were compared under standard growth conditions. The spectrum of bacterial AD activity ranged from 45.2 to 688.0 units (mg protein)$^{-1}$. *Streptococcus sanguinis* was the most prevalent species/phylotypes. Biochemical assays carried out using 27 ADS-positive strains under conditions to induce or repress ADS gene expression showed variation in arginolytic activity in response to pH, oxygen, and the availability of carbohydrate or arginine. This study reveals that the basis for the wide spectrum of arginolytic expression observed among clinical isolates is, at least in part, attributable to differences in the regulation of expression of the ADS within and between species. The results provide insights into the microbiological basis for inter-subject differences in ADS capacity of oral biofilms and enhance our understanding of dental caries as an ecologically-driven disease in which arginine metabolism moderates plaque pH and promotes dental health and provides methods for identifying bacteria for probiotic compositions and uses.

Materials and Methods

Isolation of Bacterial Strains.

Supragingival dental plaque was collected from 11 caries-free (CF) subjects with no clinical or reported evidence of present or past caries experience [decayed, missing and filled teeth (DMFT)=0] and 3 caries-active (CA) subjects with at least four active, cavitated (dentin level) and unrestored caries lesions (DT≥4, MFT≥0) as described in Nascimento et al., (2009a) and Schulte et al., (2009). The activity of caries lesions was determined by clinical appearance, plaque stagnation, and tactile sensation. To acquire a variety of cultivable microflora, plaque samples were dispersed by external sonication (W375, Sonicator Heat Systems-Ultrasonics Inc, Farmingdale, N.Y., USA) for 2 cycles of 15 seconds, with cooling on ice during the interval. Samples were then serially diluted in 10 mM sodium phosphate buffer (pH 7.0), and 100 µl of the $10^{-4}$ to $10^{-7}$ diluted samples were cultured on Sheep Blood Agar plates (Columbia Agar containing 5% of anti-coagulated sheep blood, Difco Laboratories, Detroit, Mich., USA) and on Brain-Heart Infusion (BHI) Agar plates (Difco Laboratories, Detroit, Mich., USA). Plates were incubated at 37° C. in anaerobic jars (BBL GasPak™ Systems, BD, Sparks, Md., USA) for 3 days with subsequent aerobic incubation at 37° C. in 5% $CO_2$ for 2 days. After the incubation period, colonies of clinical isolates representing all morphological types were subcultured on the same media until pure colonies were obtained.

Screening of ADS-Positive Strains.

Bacterial strains were screened for the potential to liberate ammonia from arginine in a microtiter-based assay (Schulte et al., 2009). Briefly, strains were grown in clear polystyrene microtiter-plates (Fisher Scientific Inc., USA) containing tryptone-vitamin (TV)-based broth with 0.2% galactose and 10 mM arginine. The plates were incubated under anaerobic conditions (85% $N_2$, 5% $CO_2$, 10% $H_2$, 80% relative humidity) at 37° C. for 48 hours. Bacterial cells were collected by centrifuging the plates for 3 min at 10,000×g in a refrigerated microcentrifuge, washed once with 10 mM Tris-maleate (pH 7.0) and resuspended in 100 µl of 50 mM Tris-maleate buffer (pH 6.0). The ADS-positive phenotype was identified by detecting the ammonia generated from the incubation of bacteria in the presence of 50 mM arginine-HCl for 2 hours at 37° C. using the Nessler's reagent (Sigma-Aldrich Inc., USA) (FIG. 1). Controls for background and interference were routinely included in each reaction. The library of the ADS-positive strains was stored at −80° C. for further analysis. From this library, 56 ADS-positive strains were randomly selected from the plaque of the various CF and CA subjects to be identified by 16S rRNA gene sequencing and characterized in this study.

Amplification and Sequencing of 16S rRNA Genes by PCR.

Genomic DNA from ADS-positive bacteria was isolated using the QIAamp DNA mini kit (Qiagen Inc., CA, USA) according to the instructions of the supplier. The 16S rRNA genes were amplified under standardized conditions using a universal primer set (Forward: 5'-AGA GTT TGA TCC TGG CTC AG-3' (SEQ ID NO: 1), Reverse: 5'-TAC GGG TAC CTT GTT ACG ACT-3 (SEQ ID NO: 2)). Purified PCR-products of 16S rRNA inserts were sequenced using an ABI PCR conditions and the data analyzed as described in Aas et al., (2005); Paster et al., (2001). The PCR sequences were compared to the 16S rRNA sequences deposited at the Human Oral Microbiome Database (HOMD), Ribosomal Database Project, and the GenBank database. The complete 16S rRNA gene sequences generated in this study are available for electronic retrieval from the EMBL, GenBank, and DDBJ nucleotide sequence databases.

ADS Activity, Growth Conditions and Reagents.

To ensure that novel phylotypes and known bacterial species not previously reported as ADS-positive were, in fact, capable of metabolizing arginine, ADS activity of bacterial isolates was measured by monitoring citrulline production from arginine using protocols validated by Liu et al., (2008). Bacterial isolates were maintained on fresh cultures of BHI agar and inoculated on tryptone-yeast (TY) extract broth at 37° C. for 24 hours prior to the biochemical assays for determination of ADS activity. ADS activity of the 56 selected and identified ADS-positive strains was determined under the following standard growth condition: TY medium containing 25 mM galactose and 10 mM arginine at 5% $CO_2$, at 37° C. for 24 hours Liu et al., (2008). The concentration of protein was determined using a Pierce BCA protein assay kit (Waltham, Mass., USA) with bovine serum albumin served as the standard. ADS activity levels of bacterial isolates were normalized to protein content and defined as nmol of citrulline generated [minute×(mg protein)]$^{-1}$.

Figure 2A:
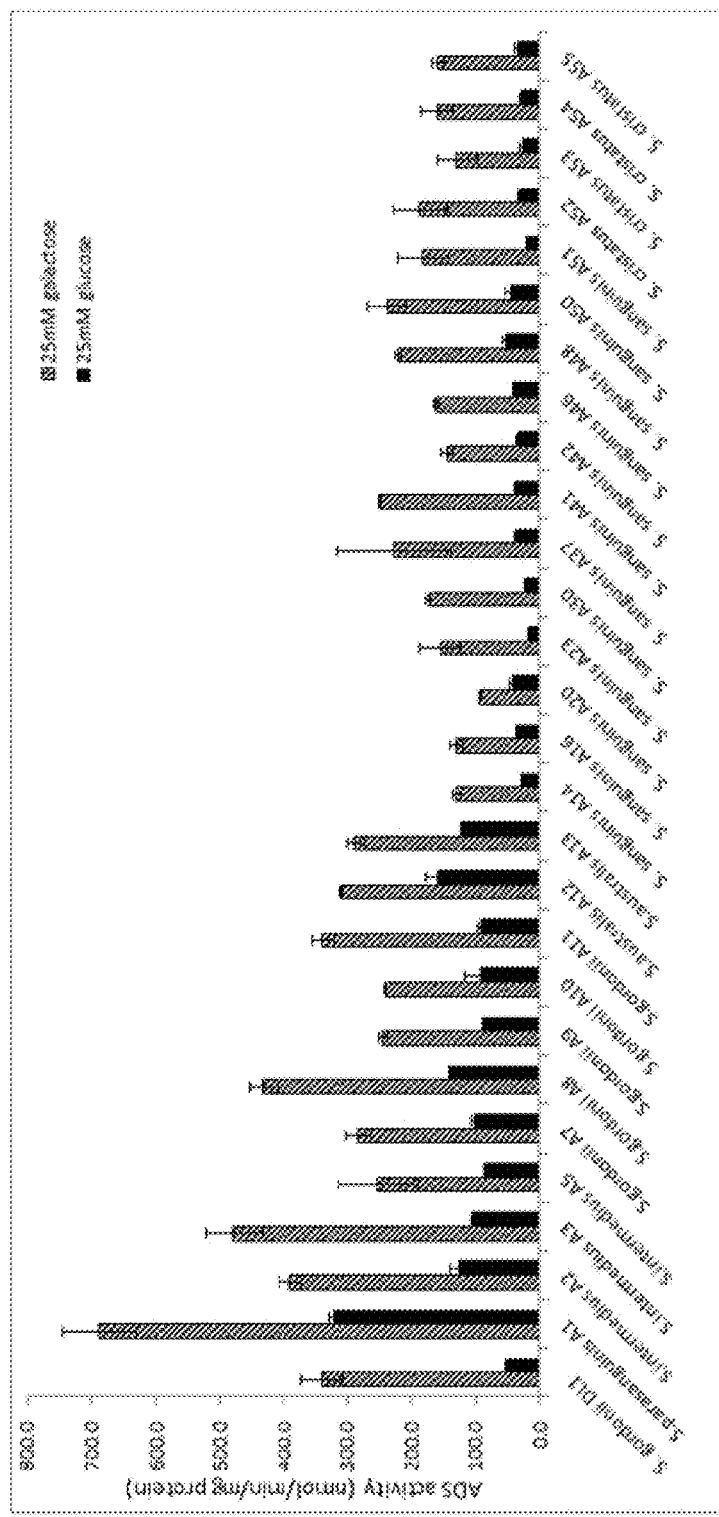
FIGS. 2A-2D represent a series of bar graphs illustrating the ADS activity levels of *S. gordonii* DL1 and ADS-positive isolates under different environmental conditions. The graphs illustrate the ADS activity in response to different sugars (FIG. 2A), different pH (FIG. 2B), the presence or absence of arginine (FIG. 2C), and aerobic (w/$O_2$) or anaerobic (w/o $O_2$) conditions (FIG. 2D). Results represent the mean and standard deviations (error bars) of three independent experiments.
Figure 2B:
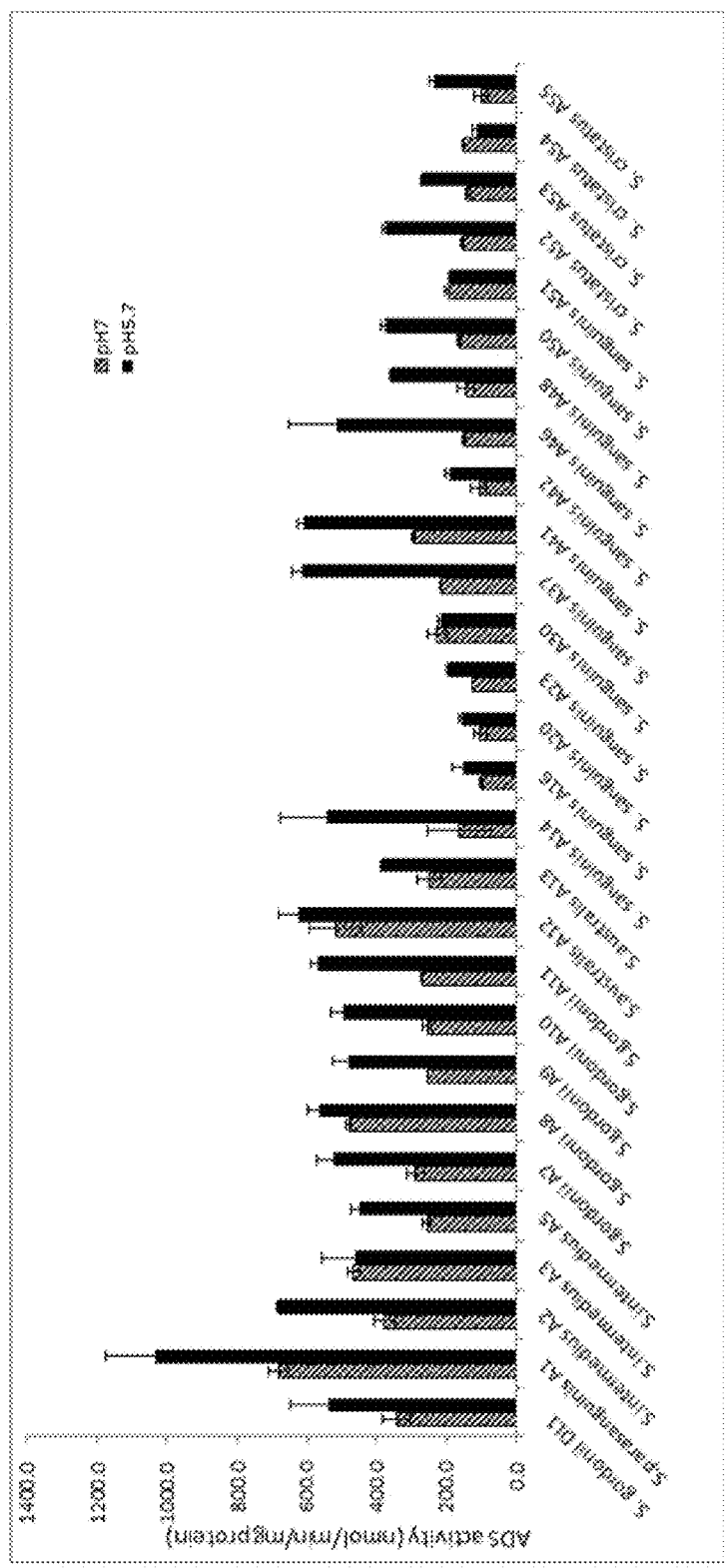

To monitor AD expression as a function of environmental conditions known to induce or repress the ADS, 27 representatives of different bacterial species were grown in TY base medium. For assays comparing ADS activity in response to different sugars, the base medium also contained 10 mM arginine and either 25 mM galactose or 25 mM glucose (FIGS. 2A and 3A). For the pH comparison assays (FIGS. 2B and 3B), the base medium also contained 25 mM galactose and 10 mM arginine that had been acidified to pH 5.7 with HCl or buffered at pH 7.0 with 50 MM $K_2HPO_4$—$KH_2PO_4$ buffer (TY/50 mM KPB). For the assays comparing the presence or absence of arginine (FIGS. 2C and 3C), the base medium also contained 25 mM galactose with or without 10 mM arginine. For the oxygen comparison assays (FIGS. 2D and 3D), the base medium also contained 25 mM galactose and 10 mM arginine with the cultures incubated under aerobic or anaerobic conditions. For aerobic growth, the cells were inoculated into a 250-ml conical flask containing 40 ml of TY medium supplemented with galactose and arginine and grown on a rotary shaker (50 rpm) at 37° C. (Liu and Burne, 2011). For anaerobic growth, cultures were incubated in an anaerobic chamber (85% $N_2$, 5% $CO_2$, 10% $H_2$, 80% relative humidity) at 37° C. for 24 hours. All the cells were collected at $OD_{600}$=0.5-0.6 for the detection of ADS activity.

Statistical Analysis.

For descriptive analysis, distribution of percentages and means were calculated when appropriate. Student's t-test or ANOVA were used to test the differences of continuous variables; and chi-square test was used for categorical variables. The correlation between the proportions of ADS-positive bacterial strains to the total cultivable organisms and the subjects' caries status was analyzed using the Two Proportions Z-test. The level of significance was determined at $p<0.05$.

Results

Arginolytic Bacterial Strains of Oral Biofilms.

A total of 2328 bacterial strains were isolated from plaque samples of the 14 participating subjects (11 CF and 3 CA; ratio of 166.3 strains isolated per subject) and screened for arginolytic capacity by detection of ADS activity. Of these 2328 strains, 288 were ADS-positive, which represents a ratio of 20.5 strains per subject, or 15.8 strains per CF subject (minimum of 5 ADS+ and maximum of 51 ADS+ strains within this caries group) and 38 strains per CA subject (minimum of 6 ADS+ and maximum of 84 ADS+ strains within this caries group). Despite considerable variation among the number of ADS-positive isolates identified within subjects and within the caries groups, there was a fair or unbiased distribution of the strains tested across subjects. There was no significant correlation between the proportions of ADS-positive strains in the total cultivable flora with the subjects' caries status.

Table 1 shows the diversity of arginolytic species isolated from supragingival dental plaque and identified by 16S rRNA gene sequencing. All 56 ADS-positive strains identified had greater than 99% sequence similarity with their assigned bacterial taxa. A total of 6 different bacterial taxa from the Firmicutes phyla were detected as the following: *S. sanguinis* (38%), *S. gordonii* (9%), *S. intermedius* (9%), *S. cristatus* (9%), *S. australis* (3%), and *S. parasanguinis* (2%).

TABLE 1

Identification and AD activities of ADS -positive isolates.

| SPECIES DESCRIPTION | STUDY CODE | ACCESSION NUMBER | SOURCE | ADS ACTIVITY (Mean ± SD) |
|---|---|---|---|---|
| *Streptococcus gordonii* DL1 | DL1 | | Lab strain | 339.3 ± 33.0 |
| arcA-deficient strains of *S. gordonii* | arcA- | | Lab strain | 0 |
| *S. parasanguinis* PTO10 | A1 | GU561390.1 | CF | 688.0 ± 57.1* |
| *S. intermedius* C270 *** | A2 | CP003858.1 | CF | 390.1 ± 17.3* |
| *S. intermedius* C270 *** | A3 | CP003858.1 | CF | 476.9 ± 43.8* |
| *S. intermedius* C270 *** | A4 | CP003858.1 | CF | 233.1 ± 15.7 |
| *S. intermedius* C270 *** | A5 | CP003858.1 | CF | 252.85 ± 61.79 |
| *S. intermedius* C270 *** | A6 | CP003858.1 | CF | 237.5 ± 11.5 |
| *S. gordonii* str. Challis substr. CH1 | A7 | AB690250.1 | CA | 283.3 ± 5.2 |
| *S. gordonii* str. Challis substr. CH1 | A8 | NR_074516.1 | CF | 431.9 ± 15.4* |
| *S. gordonii* ATCC 10558 | A9 | AY485606.1 | CA | 244.8 ± 10.7 |
| *S. gordonii* ATCC 10558 | A10 | AY485606.1 | CA | 241.3 ± 15.9 |
| *S. gordonii* ATCC 10558 | A11 | AY485606.1 | CF | 354.8 ± 20.9* |
| *S. australis* Al-1 | A12 | JX861483.1 | CF | 309.2 ± 1.4 |
| *S. australis* Al-1 | A13 | JX861483.1 | CF | 287.3 ± 12.7 |
| *S. sanguinis* SK36 | A14 | CP000387.1 | CF | 129.0 ± 5.6 |
| *S. sanguinis* SK36 | A15 | CP000387.1 | CF | 119.7 ± 3.7 |
| *S. sanguinis* SK36 | A16 | CP000387.1 | CF | 129.1 ± 10.4 |
| *S. sanguinis* SK36 | A17 | CP000387.1 | CF | 94.1 ± 4.3 |
| *S. sanguinis* SK36 | A18 | CP000387.1 | CF | 107.1 ± 9.1 |
| *S. sanguinis* SK36 | A19 | CP000387.1 | CF | 98.0 ± 5.7 |
| *S. sanguinis* SK36 | A20 | CP000387.1 | CF | 93.1 ± 1.4 |
| *S. sanguinis* SK36 | A21 | CP000387.1 | CF | 116.8 ± 14.0 |
| *S. sanguinis* SK36 | A22 | CP000387.1 | CF | 88.9 ± 10.0 |
| *S. sanguinis* SK1284_K2-1 | A23 | AB821291.1 | CA | 127.6 ± 1.1 |
| *S. sanguinis* JCM 5708 | A24 | AB596946.1 | CF | 45.2 ± 6.0 |
| *S. sanguinis* JCM 5708 | A25 | AB596946.1 | CF | 50.2 ± 3.4 |
| *S. sanguinis* JCM 5708 | A26 | AB596946.1 | CF | 46.0 ± 0.3 |
| *S. sanguinis* JCM 5708 | A27 | AB596946.1 | CF | 63.4 ± 0.0 |
| *S. sanguinis* JCM 5708 | A28 | AB596946.1 | CF | 56.4 ± 13.0 |
| *S. sanguinis* JCM 5708 | A29 | AB596946.1 | CF | 187.1 ± 20.3 |
| *S. sanguinis* JCM 5708 | A30 | AB596946.1 | CF | 173.3 ± 4.0 |
| *S. sanguinis* JCM 5708 | A31 | AB596946.1 | CF | 246.2 ± 2.4 |
| *S. sanguinis* JCM 5708 | A32 | AB596946.1 | CF | 227.3 ± 0.0 |
| *S. sanguinis* JCM 5708 | A33 | AB596946.1 | CF | 199.2 ± 8.3 |
| *S. sanguinis* JCM 5708 | A34 | AB596946.1 | CF | 200.6 ± 14.6 |
| *S. sanguinis* JCM 5708 | A35 | AB596946.1 | CF | 201.9 ± 15.2 |
| *S. sanguinis* JCM 5708 | A36 | AB596946.1 | CF | 263.4 ± 29.9 |
| *S. sanguinis* JCM 5708 | A37 | AB596946.1 | CF | 227.9 ± 89.7 |
| *S. sanguinis* JCM 5708 | A38 | AB596946.1 | CF | 167.7 ± 9.9 |
| *S. sanguinis* JCM 5708 | A39 | AB596946.1 | CF | 198.1 ± 5.1 |
| *S. sanguinis* JCM 5708 | A40 | AB596946.1 | CF | 212.5 ± 0.6 |
| *S. sanguinis* JCM 5708 | A41 | AB596946.1 | CF | 250.8 ± 1.3 |
| *S. sanguinis* JCM 5708 | A42 | AB596946.1 | CF | 144.0 ± 10.0 |

TABLE 1-continued

Identification and AD activities of ADS -positive isolates.

| SPECIES DESCRIPTION | STUDY CODE | ACCESSION NUMBER | SOURCE | ADS ACTIVITY (Mean ± SD) |
|---|---|---|---|---|
| S. sanguinis JCM 5708 | A43 | AB596946.1 | CF | 190.1 ± 10.6 |
| S. sanguinis JCM 5708 | A44 | AB596946.1 | CF | 106.4 ± 4.0 |
| S. sanguinis JCM 5708 | A45 | AB596946.1 | CF | 104.3 ± 4.1 |
| S. sanguinis JCM 5708 | A46 | AB596946.1 | CA | 161.3 ± 3.3 |
| S. sanguinis JCM 5708 | A47 | AB596946.1 | CA | 169.8 ± 6.4 |
| S. sanguinis JCM 5708 | A48 | AB596946.1 | CA | 221.3 ± 4.8 |
| S. sanguinis JCM 5708 | A49 | AB596946.1 | CA | 136.9 ± 4.3 |
| S. sanguinis JCM 5708 | A50 | AB596946.1 | CA | 238.2 ± 31.1 |
| S. sanguinis JCM 5708 | A51 | AB596946.1 | CA | 182.0 ± 39.3 |
| S. cristatus ATCC 51100 | A52 | AY584476.1 | CA | 187.5 ± 41.4 |
| S. cristatus ATCC 51100 | A53 | AY584476.1 | CA | 129.2 ± 31.6 |
| S. cristatus F0329 | A54 | AY005047.1 | CA | 160.0 ± 26.2 |
| S. cristatus F0329 | A55 | AY005047.1 | CA | 159.0 ± 9.1 |
| S. cristatus F0329 | A56 | AY005047.1 | CA | 185.9 ± 41.8 |

The 56 ADS-positive strains identified had greater than 99% sequence similarity with their assigned bacterial taxa. Database accession numbers are provided.
(*) Human Oral Taxon ID (HOT) from the Human Oral Microbiome Database (HOMD);
*ADS activity levels of bacterial strains are higher than that of S. gordonii DL1; ADS activity was expressed as nmol of citrulline generated [minute × (mg of protein)]$^{-1}$;
CF: caries-free and CA: caries-active subjects; SD: standard deviation.

The spectrum of bacterial AD activity ranged from 45.2 to 688.0 units (mg protein)$^{-1}$ when bacterial cells were incubated under standard growth conditions. There was no statistical difference between the average of bacterial ADS activity among the caries groups.

ADS Expression as a Function of Environmental Stimuli.

Figure 2C:
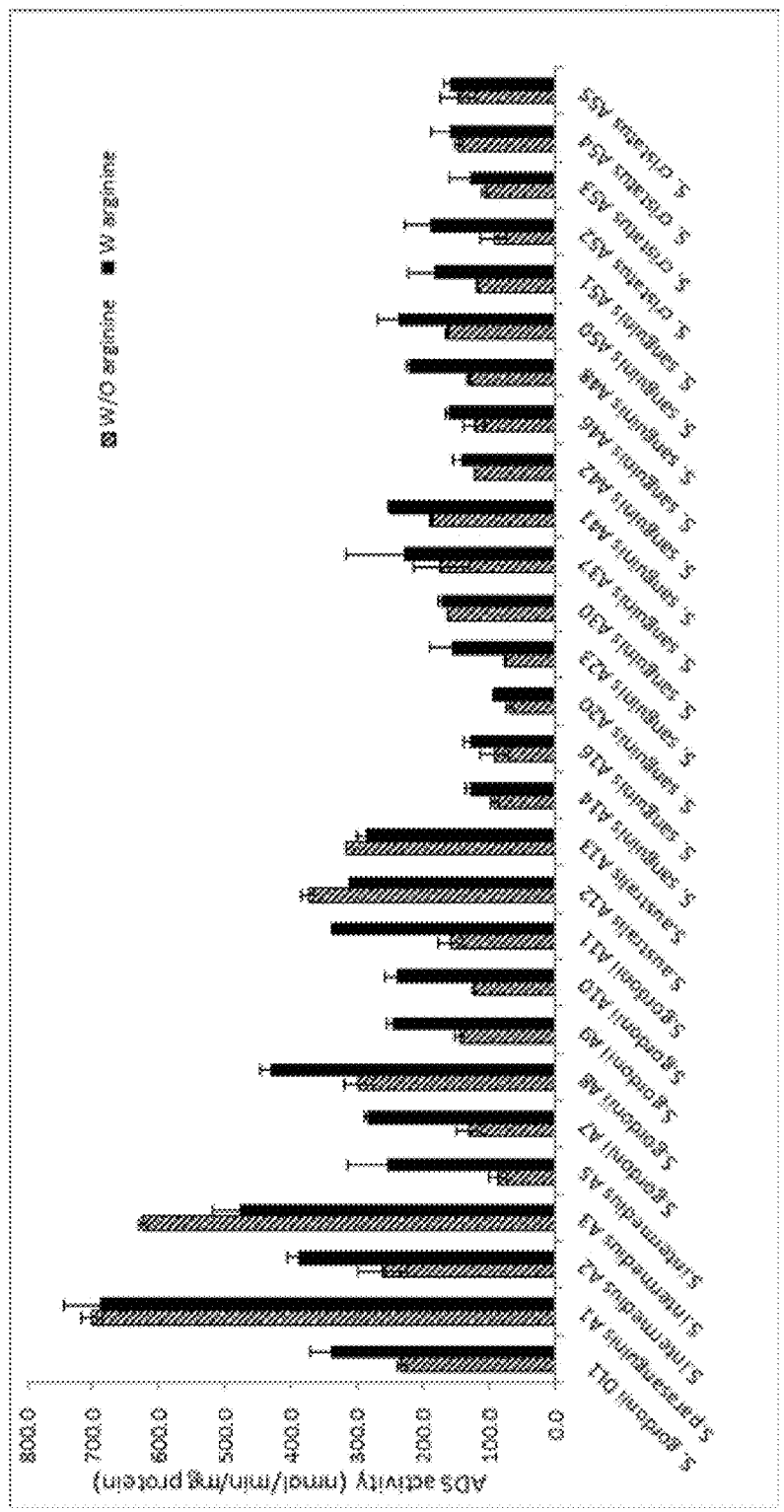

To examine regulation of ADS activity in high expressers, AD enzyme activity was measured under growth conditions known to affect the expression of ADS genes in oral bacteria, including low pH, availability of oxygen, arginine and carbohydrate. A substantial variation in ADS expression patterns was observed in response to pH, oxygen, and the availability of arginine and carbohydrate as illustrated in FIGS. 2 and 3. FIG. 2C shows that for most strains, including the laboratory strain S. gordonii DL1, optimal expression of ADS was strongly dependent on the presence of arginine. However, strains such as S. parasanguinis A1, S. intermedius A2, S. intermedius A3, S. gordonii A8, Streptococcus A12, and S. australis A13 demonstrated higher ADS expression compared to S. gordonii DL1, even in the absence of arginine. Also of note, the availability of arginine had no apparent effect on ADS expression of strains presenting lower ADS activity levels, which included S. sanguinis A14, S. sanguinis A16, and S. sanguinis A20.

A low pH environment is known to enhance ADS activity in S. gordonii DL1, however, S. parasanguinis A1, S. intermedius A2, S. intermedius A3, S. gordonii A8, and Streptococcus A12 were capable of expressing high levels of ADS activity even when cells were cultured at neutral pH (FIG. 2B), with lower fold-induction levels observed at pH 5.7.

The ADS activity of S. gordonii DL1 is also very sensitive to CCR (Dong et al., 2004), with growth in glucose resulting in 5-fold lower ADS activity compared to cells cultivated in galactose (Dong et al., 2004), which is less effective at eliciting CCR than glucose. Similarly, glucose could lower ADS activity by 8- to 10-fold in many ADS-positive strains when compared to growth in galactose (FIG. 2A). Yet, no observable repression of ADS activity by glucose was detected in S. parasanguinis A1, S. intermedius A2, S. intermedius A3, S. intermedius A5, S. gordonii A7, S. gordonii A8, S. gordonii A9, S. gordonii A10, S. gordonii A11, Streptococcus A12, and S. australis A13.

Figure 2D:
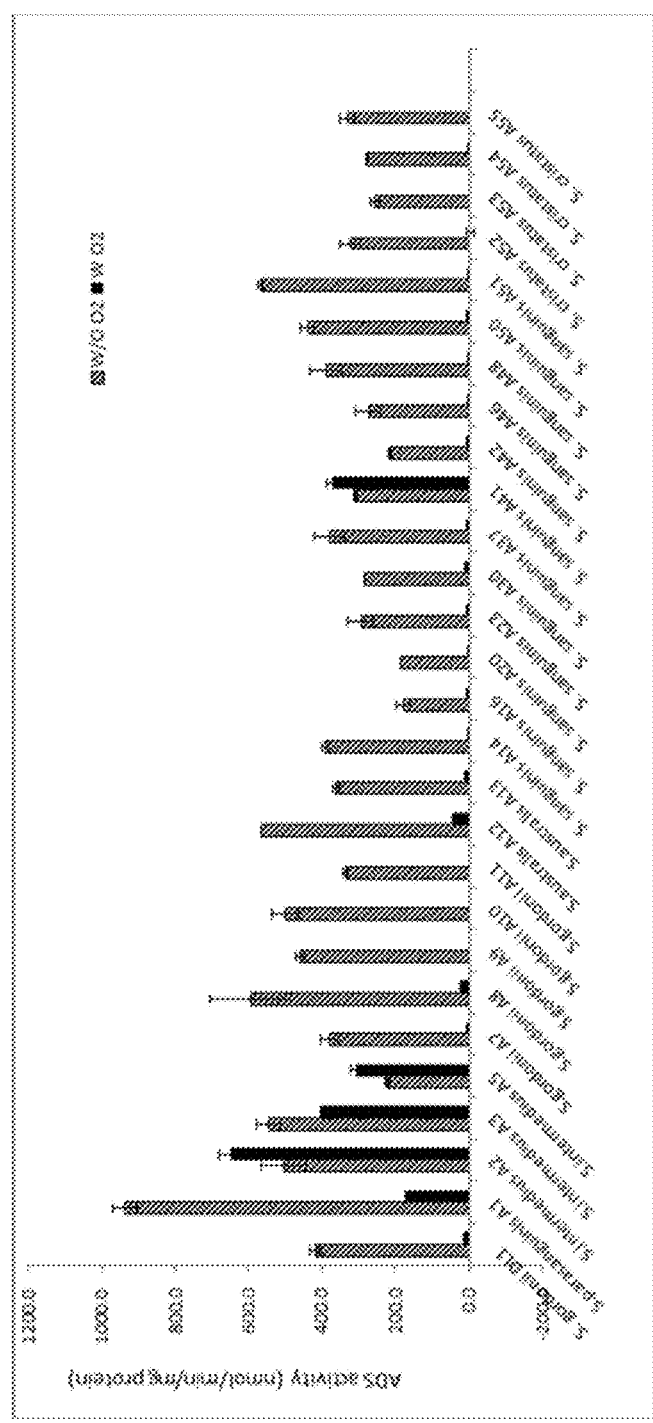

FIG. 2D shows that ADS expression of S. gordonii DL1 was highly repressed by growth under aerobic conditions and similar repression by oxygen was observed in other clinical strains. However, the ADS activity levels of some strains, such as S. parasanguinis A1, S. intermedius A2, S. intermedius A3, S. intermedius A5, S. gordonii A8, Streptococcus A12, S. sanguinis A41, and S. cristatus A55, were insensitive to the repressive effects of growth in aerated conditions.

ADS Expression and Caries Status.

As shown in Table 1, different levels of ADS activity were observed among strains of the same species isolated from plaque of CF and CA subjects. For example, the strains S. sanguinis A24 [45.2 units (mg protein)$^{-1}$] from a CF subject and A48 [221.3 units (mg protein)$^{-1}$] from a CA subject presented considerably different ADS expression under standard growth conditions. To further explore whether the arginolytic capacity of oral bacteria was related to the subjects' caries status, ADS expression in response to different environmental conditions was compared for clinical strains of same species isolated from the different caries groups (FIG. 3). The selected strains included those with highest 16S rRNA sequence similarity to S. gordonii Challis substr. CH1 (A7 and A8), S. gordonii ATCC 10558 (A10 and A11), S. sanguinis JCM 5708 (A37, A41, A48 and A50).

The strains of S. gordonii and S. sanguinis strains showed similar repression of ADS expression by glucose (FIG. 3A). Similar patterns for ADS expression and induction by acidic pH were also observed among the strains of S. gordonii and S. sanguinis from both caries (FIG. 3B). FIG. 3C shows that most strains of the same species presented comparable differences in ADS expression in response to arginine independently of the subjects' caries status. For example, both S. gordonii A7 from a CA subject and S. gordonii A8 from a CF subject showed 2-fold higher ADS activity in the presence of arginine compared to growth in the absence of arginine. Most strains showed repression of the ADS by oxygen (FIG. 3D); except for S. sanguinis A41 of a CF subject.

Discussion

Arginine metabolism in oral biofilms offers the opportunity for the development of novel anti-caries approaches from the standpoint of its short-term moderation of acid challenges to teeth and long-term effects on the persistence of desirable bacteria in dental plaque. For arginolysis is to be used in the development of strategies to assess caries risk and to control caries, insight into the distribution, regulation and function of the ADS in oral biofilms in health and disease was needed. Although genome sequencing and other molecular techniques have revealed new levels of complexity in the cariogenic microflora and in the nature of individual bacterial species (Aas et al., 2008; Corby et al., 2005; Crielaard et al., 2011; Mager et al., 2003; Russell, 2008), limited attempts (Sissons et al., 1988a; Sissons et al., 1988b; Sissons et al., 1994) have been made to identify and characterize clinically-relevant oral organisms capable of producing alkali that can potentially affect the cariogenicity of oral biofilms. In this example, a rapid and simple protocol was developed for screening of cultivable arginolytic bacteria isolated from dental plaque samples. Even though the majority of the ADS-positive bacterial species identified were strains of *S. sanguinis* and *S. gordonii*, we were able to disclose additional cultivable taxa that contribute to the total oral arginolysis, such as species of *Actinomyces, Bacillus*, and *Neisseria*. In conjunction with previous microbiological studies demonstrating the abundance in human oral biofilms of the commensal streptococci identified here (Aas et al., 2008; Aas et al., 2005; Corby et al., 2005; Crielaard et al., 2011; Dewhirst et al., 2010; Gross et al., 2010; Mager et al., 2003), the results in these examples revealed that these abundant streptococci likely have a dominant influence on the arginolytic capacity of human oral biofilms. Importantly, this study clearly demonstrated that the ADS of clinical strains is in fact regulated in response to those specific environmental factors that have the greatest impact on the composition and biochemical activities of supragingival biofilms; e.g. availability and source of carbohydrate, low pH and oxygen, which are also environmental factors that can influence the development of caries.

The diversity of the oral microbiota associated with health and disease is only beginning to be described by high-throughput methodologies (Aas et al., 2008; Corby et al., 2005; Crielaard et al., 2011; Gross et al., 2010; Mager et al., 2003). While this species- or taxa-level identification is tremendously valuable (Dewhirst et al., 2010), it does not address the fact that there is significant heterogeneity within given species of oral bacteria. Based on current sequencing efforts, the majority of ADS-positive oral bacterial species is cultivable, and mostly includes abundant oral streptococci. Uncultivable organisms may also contribute to the total arginolytic activity measured in oral biofilms. However, this theory is not supported by the above results, in which there was no association of alkali-generating potential with organisms that were unlikely to grow under the conditions used in the present examples to cultivate plaque samples or that are generally recognized as uncultivable, e.g. certain spirochetes. Thus, any contribution to total ADS of uncultivable organisms is probably negligible. Not only are uncultivable bacterial species represented in plaque in far lower amounts compared to cultivable species (Aas et al., 2008; Corby et al., 2005; Crielaard et al., 2011; Gross et al., 2010; Mager et al., 2003), but many or most of the uncultivable bacteria do not appear to harbor the ADS genes. This present study enhances ongoing oral microbiome efforts by highlighting the phenotypic heterogeneity of the more abundant species in the oral cavity in the context of their abilities to modulate the pH, and thus the cariogenic potential, of oral biofilms. This study also presents novel concepts regarding the molecular basis for heterogeneity in alkali production, while concurrently generating knowledge, strains, probes and reagents that will advance existing methodologies for evaluating and understanding the pathogenic potential of the oral microbiome.

Markedly less is known about the production of alkali than is known about sugar metabolism in oral biofilms. The causal relationship between bacterial sugar metabolism and acid production by a mixed population of plaque bacteria was first described by Stephan in 1940 (Stephan, 1940). Stephan also pointed out that the drop in plaque pH detected after sugar challenge is followed by a gradual rise in plaque pH that eventually reaches a plateau. Later, the plateau, or resting pH, of caries-active plaque was found to be more acidic than that of caries-free plaque (Margolis et al., 1988a), further supporting a correlation between acid production and dental caries. Subsequent studies showed that the rise in plaque pH is largely due to ammonia production from arginine or urea by a subset of acid-sensitive organisms present in saliva and plaque (Wijeyeweera and Kleinberg, 1989b). Marquis suggested that the buffering capacity from ammonia production in oral biofilms moderates the speed of the pH drop and allows time for the base-producing bacteria to adjust their physiology for survival (Marquis, 1995). Kleinberg showed that carbohydrate-starved plaque was more alkaline than the saliva bathing the plaque, mainly in regions of greater saliva flow (Kleinberg and Jenkins, 1964), so it was suggested that plaque bacteria generate ammonia from salivary substrates more rapidly than the forces of diffusion can clear them from dental plaque (Kleinberg and Jenkins, 1964). Kleinberg also indicated that the plaque pH would be determined by the acid-base metabolism of plaque organisms, which in turn could be affected by plaque thickness, the proportions of acid- and base-producing organisms in plaque, and the relative availability of nitrogenous and carbohydrates substrates (Kleinberg, 1970).

Clinical studies to date support that caries susceptibility involves a deficiency in alkali production and not solely acid production, as has been traditionally assumed (Nascimento et al., 2009b; Nascimento et al., 2012; Shu et al., 2007b). In the present example, we examined whether the heterogeneity of oral bacterial strains, the constitutional difference in the ADS genes expression levels, and/or differential sensitivity of the ADS genes to induction or repression by environmental factors, could account for the high degree of variability in alkali production detected in dental health and when caries activity is evident. Although ADS-positive strains from caries-free subjects showed slightly higher levels of ADS activity than those isolated from caries-active subjects, there was no significant correlation between levels of bacterial ADS activity and hosts' caries status. Yet, this study examining a collection of arginolytic plaque bacteria, or more specifically, the ADS activity in closely-related but physiologically-diverse commensal streptococci, revealed a considerable and surprising spectrum of responses of the ADS to multiple environmental stimuli. In the complex environment of oral biofilms where many variables can influence microbial behavior, the arginolytic expression of clinical strains may be dependent on the growth conditions. Thus, it is possible that the basis for differences in arginolysis observed between caries-free and caries-active subjects can be associated with a combination of factors: (i) the carriage in oral biofilms of strains that have inherent differences in the regulation of the ADS by environmental factors, and/or (ii) host and biofilm micro-environmental factors that influence ADS expression in vivo. For example, the biofilms of caries-active subjects appear to be in-conducive to high ADS expression or to provide some inhibitory factors that decrease ADS activity. Thus, arginolytic clinical strains with constitutionally high ADS-expressing phenotypes and those in which ADS expression is insensitive to conditions known to cause dental caries, such as sugar availability and acidic environment, have use in probiotic therapies to prevent and control dental caries.

This study reveals that the microbial basis for intra-subject variations in oral arginolysis is more complex than previously appreciated; not only may the arginolytic potential of oral biofilms be associated with the carriage of certain strains of bacteria, but also arginolytic species display a range of ADS activity as a function of environmental factors. The results are highly significant in the context of understanding caries as an ecologically-driven disease by supporting that high ADS-expressing strains could positively affect plaque ecology synergistically by moderating plaque pH and reducing the risk for caries. This study expanded the knowledge on the diversity of the oral alkali-generating bacteria and their role in oral health and disease.

Example 2

ADS Activity and Interspecies Antagonism

A survey of a spectrum of supragingival clinical isolates in Example 1, above, demonstrated that ADS gene expression can be highly variable within and between species, and that the variability was attributable to both constitutional and environmentally-modulated differences in the expression of ADS activity. Considering that isolates that have a high potential to catabolize arginine and that it would be particularly beneficial to the host if they could also suppress the growth of caries pathogens, the present example examined the capacity of selected oral arginolytic isolates to antagonize the growth of S. mutans or to be inhibited by S. mutans.

This example investigated the antagonistic potential and mechanisms of clinical isolates of arginolytic streptococci identified in Example 1 on and by Streptococcus mutans UA159, a well-characterized cariogenic human isolate. Low-passage isolates of Streptococcus gordonii, Streptococcus sanguinis, Streptococcus parasanguinis, Streptococcus australis and Streptococcus cristatus inhibited the growth of S. mutans to various degrees when they were inoculated on growth media first or simultaneously with S. mutans. The antagonistic effects of arginolytic strains against S. mutans and the production of $H_2O_2$ by these strains were enhanced during growth in a less-rich medium or when galactose was substituted for glucose as the primary carbohydrate source. Pyruvate oxidase was the dominant pathway for $H_2O_2$ production by arginolytic strains, but lactate oxidase activity was also detected in some strains of S. gordonii and S. cristatus.

Methods and Materials

Bacterial Strains, Media, and Growth Conditions.

The reference strains S. mutans UA159 and S. gordonii DL1, along with 56 ADS-positive low-passage clinical isolates were routinely grown in brain heart infusion (BHI) broth (3.7% containing a final concentration of 2 g of glucose/L; Difco Laboratories, Detroit, Mich., USA) or on BHI agar plates. The arginolytic strains were previously isolated from supragingival dental plaque samples of caries-free (CF) and caries-active (CA) subjects and characterized as described in Example 1, above. Based on complete 16S sequence, the arginolytic clinical strains used in this study were most similar (>98% rDNA sequence identity) to the following species: S. sanguinis (n=38), S. parasanguinis (n=1), S. intermedius (n=5), S. gordonii (n=5), S. australis (n=2) and S. cristatus (n=5). Several modified agar media were formulated with different carbohydrate sources and nutrient composition: TY (3% tryptone and 0.5% yeast extract) supplemented with 25 mM galactose (TY-25 mM galactose) or 25 mM glucose (TY-25 mM glucose), a more dilute version of TY (1% tryptone, 0.2% yeast extract) supplemented with 25 mM galactose (TY-D-25 mM galactose), half-strength TY-25 mM galactose (1.5% tryptone, 0.25% yeast extract and 12.5 mM galactose) with or without 20 mM arginine, and half-strength BHI (1.85% BHI with a final concentration of 1 g of glucose/L).

Preparation of Gradient Agar Plates.

Gradient BHI or TY-25 mM galactose agar plates were used to detect the influence of nutritional gradients on the antagonistic capacity of the tested strains. Briefly, 15 mL of agar (constituted in $dH_2O$ and without nutrients) were poured into the plates and the plates were tilted. After the agar had solidified (approximately 1 hour after pouring the agar), the plates were placed in a horizontal position and another 15 mL of BHI or TY-25 mM galactose agar were poured as the top layer.

Preparation of Saliva Agar.

Saliva agar plates were used for bacterial competition assays and prepared as described in De Jong et al., 1986 (hereby incorporated by reference herein), with certain modifications. Whole stimulated saliva was collected from members of our laboratory by asking them to chew on sterile paraffin wax. Informed consent was obtained from all saliva donors under a protocol reviewed and approved by the Institutional Review Board of the University of Florida Health Science Center. The saliva donors were not users of toothpaste containing compounds with strong antimicrobial activities, nor were they being treated with antimicrobial drugs at the time of saliva collection. The saliva samples were pooled and subsequently diluted with sterile demineralized water in a 2:1 ratio. Dithiothreitol (DTT) was added to the saliva mix to a final concentration of 2.5 mmol/L and then the saliva mix was slowly stirred for 10 min. To inactive catalase and peroxidase enzymes, the saliva mix was heated at 60° C. for 10 min, centrifuged and filter-sterilized. Glucose, galactose or arginine was added to the treated saliva to a final concentration of 5 mM. Finally, 5 ml of melted 6% agar (approximately at 50° C. and constituted in $dH_2O$) was mixed with 15 ml of the saliva media and immediately poured into sterile petri dishes.

Competition Assays.

TY-25 mM galactose, TY-25 mM glucose, half-strength BHI and BHI agar plates were used for competition assays between the arginolytic strains and S. mutans UA159. Overnight cultures of each strain grown in BHI broth had their optical density at 600 nm ($OD_{600}$) adjusted to 0.5. Each strain (6 µl) was then inoculated adjacent to one another on agar plates as follows: (i) arginolytic strains first, followed by UA159 24 h later; (ii) UA159 first, followed by arginolytic strains 24 h later; or (iii) arginolytic strains and UA159 inoculated at the same time. The plates were incubated for an additional 24 h at 37° C., in 5% $CO_2$ and 95% air. AlphaEaseFC software was used to measure the zones of growth inhibition on all tested agar media.

Of the 56 arginolytic strains tested (see results in Table 2, below), 10 strains were selected for further assessments of the environmental factors that may influence their antagonistic capacity. The selection criteria were based primarily on differences in species and antagonistic capacities against S. mutans UA159, as compared to the reference strain S.

*gordonii* DL1. The 16S sequences of the selected strains were most similar (>98% identity) to five bacterial species: *S. sanguinis, S. parasanguinis, S. gordonii, S. australis*, and *S. cristatus*.

Half-strength TY-25 mM galactose plates with or without 20 mM arginine were used to assess the effect of arginine availability on antagonistic potential. Competition assays were also performed in anaerobic (85% $N_2$, 5% $CO_2$, 10% $H_2$) or aerobic (5% $CO_2$, 95% air) conditions to assess the impact of oxygen. To further explore the mechanisms of growth inhibition by *S. mutans* UA159, 2.5 µg/µL of catalase (2950 units/mg solid, Sigma, St. Louis, Mo., USA) or 1 µg/µL proteinase K (7.5 units/mg solid, Sigma, St. Louis, Mo., USA) was added to the agar plates. Specifically, 6 µl of overnight cultures of arginolytic bacteria were spotted on the agar plates. Next, 5 µl phosphate-buffered saline (PBS: 137 mM NaCl, 2.7 mM KCl, 4.3 mM $Na_2HPO_4.7H_2O$, 1.4 mM $KH_2PO_4$, pH 7.3), or catalase or proteinase K in PBS, was applied adjacent to the inoculation spot on the agar plate or before spotting 5 µl of an overnight culture of UA159 as follows: (a) arginolytic bacteria first, followed by UA159 24 h later or (b) arginolytic bacteria first, followed by UA159 immediately after.

$H_2O_2$ Production.

To test the capacity of the strains to produce $H_2O_2$, overnight cultures of selected arginolytic bacteria were diluted (1:20) into TY-25 mM glucose, TY-25 mM galactose or TY-D-25 mM galactose and allowed to grow to $OD_{600}=0.3$ in static culture in a 37° C. aerobic incubator. The cultures were then shaken at 200 RPM in a 37° C. aerobic shaker/incubator for 30 min. The assay for $H_2O_2$ production was performed as previously described in Tong et al., 2007 (hereby incorporated by reference herein) with some modifications. First, 0.6 ml of culture supernate was added to 0.6 ml of a solution containing 2.5 mM of 4-aminoantipyrine (4-amino-2,3-dimethyl-1-phenyl-3-pyrazolin-5-one; Sigma) and 0.17 M phenol (Fisher Scientific, Pittsburgh, Pa., USA). After 4 min of incubation at room temperature, horseradish peroxidase (Pierce, Thermo Scientific, Grand Island, N.Y., USA) diluted in 0.2 M potassium phosphate buffer (pH 7.2) was added to the reaction solution at a final concentration of 13 mU/ml. After 20 min of incubation at room temperature, the culture absorbance was measured at $OD_{510}$. A standard curve with known concentrations of fresh $H_2O_2$ (30% w/w, Fisher Scientific) was generated at each time the assays were performed.

Activity of $H_2O_2$-Generating Oxidase Enzymes.

To measure the activity of certain $H_2O_2$-generating enzymes, BHI overnight cultures of the selected arginolytic bacteria were centrifuged at 4,000×g for 10 min, washed twice with 2 ml of PBS and the pelleted cells were resuspended in 2 ml of PBS. Aliquots of the cell suspension were used for determining lactate oxidase activity, and the remaining cell suspensions were permeabilized for determination of pyruvate oxidase, L-arginine oxidase, and NADH oxidase activities by mixing the cell suspension with 0.02 volumes of toluene-acetone (1:9, v/v) and vortexing the mixture for 2 min. The protein concentration in the cell preparations was determined by using a Pierce BCA protein assay kit (Waltham, Mass., USA) with bovine serum albumin as the standard.

Pyruvate oxidase activity was determined by measuring the production of acetyl phosphate (AcP) as described in Fowler et al., 2011, Liu et al., 2102, and Huang et al., 2016 (hereby incorporated by reference herein), with some modifications. The reaction mixture consisted of 0.45 ml of the permeabilized cell suspension and 0.45 ml of a solution containing 50 mM potassium phosphate buffer ($KPO_4$; pH 6.0), 10 µM $MgCl_2$, 0.2 µM thiamine pyrophosphate (Sigma), 50 mM potassium pyruvate, and 12 µM flavin adenine dinucleotide (FAD; Sigma). Controls included reactions without permeabilized cells or without potassium pyruvate. The reaction mixtures were incubated at 37° C. for 30 min with shaking at 250 rpm, and the amount of acetyl phosphate generated during the reaction was then measured as follows. Aliquots of cell suspensions (0.3 ml) were pre-incubated at 37° C. for 1 min in a 111002 heat block (Boekel Scientific, Feasterville, Pa., USA) followed by the addition of 50 µL of 2 M hydroxylamine hydrochloride solution, and further incubation at 60° C. for 5 min in the heat block. Next, 100 µl of a development solution containing equal volumes of 0.5 M ferric chloride in 5 M HCl and 30% trichloroacetic acid was added to the reaction solution, and color was allowed to develop for at least 1 min at room temperature. The samples were centrifuged and the absorbance of the supernates was measured at $OD_{540}$. A standard curve was generated with known concentrations of lithium potassium acetyl phosphate (Sigma).

The activity of lactate, L-arginine and NADH oxidases was assessed by measuring $H_2O_2$ production as described in Liu and Huang, incorporated above. For lactate oxidase assays, 0.45 ml of intact cells was added to 0.45 ml of 0.2 M sodium phosphate buffer (pH 7.0) containing 20 mM sodium L-lactate. The mixtures were incubated at 37° C. with shaking at 250 rpm for 30 min. For L-arginine oxidase assays, 0.45 ml of permeabilized cell suspensions was added to 0.45 ml of 0.2 M sodium phosphate buffer (pH 7.0) containing 20 mM L-arginine. The mixtures were incubated at 37° C. with shaking at 250 rpm for 2 h. For NADH oxidase assays, 0.45 ml of permeabilized cell suspensions was added to 0.45 ml of 0.2 M sodium phosphate buffer (pH 7.0) containing 13 mM NADH. The mixtures were incubated at 37° C. with shaking at 250 rpm for 3 h, and the concentration of $H_2O_2$ in the supernates was determined. Controls included reaction solutions without sodium salts of L-lactate, L-arginine or NADH, respectively.

Statistical Analysis.

For descriptive analysis, the distribution of percentages and means were calculated when appropriate. Student's t test was used to analyze the influence of growth conditions (TY-25 mM galactose versus TY-25 mM glucose, 1/2 strength BHI versus BHI), source of the isolate (CF versus CA subjects), and the zones of inhibition of *S. mutans* grown with or without arginine. Two-way ANOVA was used to analyze the influence of the type of strain and growth conditions, and Dunnet test in one-way ANOVA was used to compare the strains growth in a given condition. The level of significance was determined at $p<0.05$.

Results

Interspecies Antagonism.

Table 2 shows results of antagonism studies of and by *S. mutans* UA159 with 56 different ADS activities isolates examined using plate inhibition assays. Highly ADS-active isolates showed the ability to survive in the presence of *S. mutans*. Isolates of *S. gordonii, S. australis* and *S. sanguinis* showed a potent ability to inhibit the growth of *S. mutans* UA159. Since the growth of many of the ADS-positive isolates was not inhibited by *S. mutans*, not only may the arginolytic potential of oral biofilms be associated with the carriage of certain strains of bacteria, but also arginolytic species display a range of abilities to inhibit, and to be inhibited by, *S. mutans*.

TABLE 2

Inhibitory effects of ADS-positive isolates on the growth S. mutans UA159.

| | | Antagonistic activity (on TY-galactose medium) | | |
|---|---|---|---|---|
| SPECIES DESCRIPTION | STUDY CODE | Testing strain first (unit: 0.1 mm) | S. mutans first (unit: 0.1 mm) | At the same time (unit: 0.1 mm) |
| Streptococcus gordonii DL1 | | 7.2 ± 0.4 | −64.8 ± 2.2 | 6.8 ± 0.8 |
| arcA-deficient strains of S. gordonii | | 7.2 ± 0.4 | −62.0 ± 2.2 | 5.0 ± 0.8 |
| S. parasanguinis PTO10 | A1 | 5.0 ± 0 | 0 ± 0 | 0 ± 0 |
| S. intermedius C270 *** | A2 | 0 ± 0 | −80.0 ± 0 | −25.0 ± 1.4 |
| S. intermedius C270 *** | A3 | 0 ± 0 | −80.0 ± 0 | −32.3 ± 3.1 |
| S. intermedius C270 *** | A4 | 0 ± 0 | −80 ± 0 | −39.4 ± 2.6 |
| S. intermedius C270 *** | A5 | 0 ± 0 | −80 ± 0 | −57.3 ± 2.8 |
| S. intermedius C270 *** | A6 | 0 ± 0 | −80 ± 0 | −55.0 ± 3.0 |
| S. gordonii str. Challis substr. CH1 | A7 | 6.0 ± 0.7 | −70.0 ± 0 | 3.0 ± 0.8 |
| S. gordonii str. Challis substr. CH1 | A8 | 22.8 ± 2.2** | −18.3 ± 2.1 | 13.0 ± 0.8 |
| S. gordonii ATCC 10558 | A9 | 5.8 ± 0.4 | −66.8 ± 2.4 | 5.2 ± 0.8 |
| S. gordonii ATCC 10558 | A10 | 4.6 ± 0.5 | −71.8 ± 9.5 | 4.4 ± 0.5 |
| S. gordonii ATCC 10558 | A11 | 12.5 ± 1.8** | −40.0 ± 0 | 3.0 ± 1.2 |
| S. australis Al-1 | A12 | 20.6 ± 1.3** | −65.0 ± 6.0 | 8.6 ± 0.9 |
| S. australis Al-1 | A13 | 22.4 ± 3.6** | −63.7 ± 3.8 | 7.2 ± 0.8 |
| S. sanguinis SK36 | A14 | 12.7 ± 1.6** | −80.0 ± 0 | 6.4 ± 3.1 |
| S. sanguinis SK36 | A15 | 11.4 ± 1.1** | −80 | 2.8 ± 0.8 |
| S. sanguinis SK36 | A16 | 18.5 ± 2.4** | −25.3 ± 4.5 | 9.6 ± 1.1 |
| S. sanguinis SK36 | A17 | 21.0 ± 2.0** | 0 ± 0 | 12.5 ± 1.0 |
| S. sanguinis SK36 | A18 | 14.3 ± 1.7** | 0 ± 0 | 7.0 ± 1.0 |
| S. sanguinis SK36 | A19 | 17.8 ± 1.0** | −29.5 ± 4.5 | 13.4 ± 1.5 |
| S. sanguinis SK36 | A20 | 14.5 ± 0.6** | −80 ± 0 | 4.8 ± 0.5 |
| S. sanguinis SK36 | A21 | 13.0 ± 1.1** | −64.3 ± 3.1 | 5.2 ± 0.8 |
| S. sanguinis SK36 | A22 | 6.0 ± 1.7 | −73.3 ± 5.2 | 4.0 ± 1.0 |
| S. sanguinis SK1284_K2-1 | A23 | 7.0 ± 0.9** | −75 ± 5.8 | 4 ± 1.2 |
| S. sanguinis JCM 5708 | A24 | 4.6 ± 0.9 | −80.0 ± 0 | −15.0 ± 4.0 |
| S. sanguinis JCM 5708 | A25 | 0 ± 0 | −80.0 ± 0 | −7.25 ± 0.5 |
| S. sanguinis JCM 5708 | A26 | 5.6 ± 1.7 | −80.0 ± 0 | 1.6 ± 0.9 |
| S. sanguinis JCM 5708 | A27 | 0 ± 0 | −80 ± 0 | 0.2 ± 2.4 |
| S. sanguinis JCM 5708 | A28 | 2.0 ± 0 | −65.8 ± 2.9 | 2.0 ± 0 |
| S. sanguinis JCM 5708 | A29 | 2.4 ± 0.9 | −80.0 ± 0 | 0 ± 0 |
| S. sanguinis JCM 5708 | A30 | 6.3 ± 0.5 | −80.0 ± 0 | 0 ± 0 |
| S. sanguinis JCM 5708 | A31 | 2.6 ± 0.5 | −76.7 ± 5.8 | −14.6 ± 3.2 |
| S. sanguinis JCM 5708 | A32 | 4.2 ± 0.8 | −70.0 ± 5.3 | 0 ± 0 |
| S. sanguinis JCM 5708 | A33 | 20.4 ± 1.1** | −61.5 ± 3.0 | 6.8 ± 1.3 |
| S. sanguinis JCM 5708 | A34 | 9.8 ± 0.4** | −71.75 ± 2.6 | 1.8 ± 0.5 |
| S. sanguinis JCM 5708 | A35 | 9.0 ± 0.9** | −69.5 ± 1.9 | 4.0 ± 1.2 |
| S. sanguinis JCM 5708 | A36 | 1.0 ± 0 | −66.5 ± 1.0 | 2.0 ± 0 |
| S. sanguinis JCM 5708 | A37 | 5.6 ± 1.7 | −68.5 ± 3.7 | 1.0 ± 0.7 |
| S. sanguinis JCM 5708 | A38 | 3.6 ± 0.9 | −68.5 ± 2.5 | −5.8 ± 1.7 |
| S. sanguinis JCM 5708 | A39 | 6.8 ± 0.8 | −63.3 ± 7.2 | 2.5 ± 1.3 |
| S. sanguinis JCM 5708 | A40 | 1.8 ± 0.8 | −61.8 ± 2.8 | 1.6 ± 0.5 |
| S. sanguinis JCM 5708 | A41 | 0 ± 0 | −80 ± 0 | −9 ± 3.3 |
| S. sanguinis JCM 5708 | A42 | 11.6 ± 2.1** | −29.0 ± 1.0 | 9.4 ± 0.5 |
| S. sanguinis JCM 5708 | A43 | 12.8 ± 1.7** | −68.0 ± 3.5 | 14.7 ± 1.4 |
| S. sanguinis JCM 5708 | A44 | 5.8 ± 0.5 | −43.8 ± 4.8 | 3.8 ± 1.1 |
| S. sanguinis JCM 5708 | A45 | 8.0 ± 1.2** | −80 ± 0 | 8.5 ± 1.0 |
| S. sanguinis JCM 5708 | A46 | 0.7 ± 1.0 | −80 ± 0 | 0.7 ± 1.0 |
| S. sanguinis JCM 5708 | A47 | 2.58 ± 2.4 | −80.0 ± 0 | 0.68 ± 0.9 |
| S. sanguinis JCM 5708 | A48 | 0.4 ± 0.9 | −80.0 ± 0 | 0 ± 0 |
| S. sanguinis JCM 5708 | A49 | 5.8 ± 0.5 | 0 | 6.6 ± 0.5 |
| S. sanguinis JCM 5708 | A50 | 0 ± 0 | −69.2 ± 2.0 | 0 ± 0 |
| S. sanguinis JCM 5708 | A51 | 5.2 ± 0.4 | 2.0 ± 0 | 4.7 ± 1.5 |
| S. cristatus ATCC 51100 | A52 | 16.0 ± 1.3** | −80.0 ± 0 | −19.0 ± 5.3 |
| S. cristatus ATCC 51100 | A53 | 4.8 ± 1.2 | −80.0 ± 0 | 1.8 ± 0.5 |
| S. cristatus F0329 | A54 | 1.5 ± 1.0 | −80.0 ± 0 | 1.3 ± 0.5 |
| S. cristatus F0329 | A55 | 16.5 ± 0.5** | −80.0 ± 0 | 4.0 ± 0.8 |
| S. cristatus F0329 | A56 | 5.6 ± 2.1 | −80.0 ± 0 | −19.3 ± 5.1 |

**Antagonistic activity levels of bacterial strains are higher than that of S. gordonii DL1 when arginolytic isolate were inoculated first (before the S. mutans strain);
(−) Arginolytic isolates were inhibited by S. mutans;
SD: standard deviation.

Arginolytic Strains have Variable Capacity to Inhibit the Growth of S. mutans UA159.

Table 3 shows the mean average of the growth inhibition zones of the closest relative species representing the 56 arginolytic strains of Table 2 tested for antagonistic capacity on and by S. mutans UA159. The growth of all arginolytic strains was inhibited when S. mutans was inoculated first on the different media tested. However, clinical strains of S. sanguinis, S. parasanguinis, S. gordonii, S. australis and S. cristatus could inhibit the growth of UA159 to various degrees when inoculated first on the different media tested. Strains of S. intermedius were the only group that was not able to inhibit the growth of S. mutans when inoculated first or simultaneously on the various agar media. When inoculated first on TY-25 mM galactose, strains of S. gordonii, S. australis and S. cristatus showed greater inhibition of S. mutans, compared to the reference strain S. gordonii DL1. When inoculated first on TY-25 mM glucose plates, strains of S. australis and S. cristatus also presented greater inhibition of S. mutans, compared to the reference strain. Overall, S. australis displayed the strongest inhibitory effects on S. mutans when inoculated first onto TY agar, whereas DL1 displayed the strongest inhibitory effects when inoculated first onto BHI agar.

Strains of S. parasanguinis, S. sanguinis, S. gordonii, and S. australis could inhibit the growth of S. mutans to different degrees when inoculated simultaneously on TY-25 mM galactose agar. Strains of S. gordonii and S. australis could also inhibit the growth of S. mutans when inoculated simultaneously onto half-strength BHI agar. In fact, strains of S. australis were the only group of clinical isolates capable of inhibiting S. mutans when inoculated simultaneously onto the media tested. Of note, S. australis showed greater inhibitory effects on UA159 than did S. gordonii DL1 when the clinical strains were inoculated simultaneously with UA159 on TY-25 mM galactose or TY-25 mM glucose plates.

Two strains of S. sanguinis isolated from CF subjects showed differences in their antagonistic capacity against S. mutans. Specifically, one strain of S. sanguinis (A17), for which the best BLAST match on 16S rDNA was S. sanguinis SK36, showed significant inhibition of S. mutans (2.1±0.2 mm zone of inhibition when colonizing first, 1.3±0.1 mm when colonizing simultaneously) on TY-25 mM galactose plates, while another strain of S. sanguinis (A51), with a 16S rDNA sequence most similar to S. sanguinis ChDC B357, showed no capacity to inhibit the growth of S. mutans under any condition. Table 4 shows the mean of the zones of growth inhibition on S. mutans by strains with similar 16S matches, but that were isolated from either from CF or CA subjects. Strains isolated from CF subjects showed a significantly stronger inhibitory effect on S. mutans than those from CA subjects in the media tested, except for strains most similar to S. sanguinis JCM 5708 grown on TY-25 mM glucose and BHI plates.

TABLE 3

Mean average of growth inhibition zones of the arginolytic bacterial strains on or by S. mutans UA159.

|  | TY-25 mM galactose | TY-25 mM glucose | ½ strength BHI | BHI |
|---|---|---|---|---|
| On S. mutans UA159 | | | | |
| S. gordonii DL1 | 0.7 ± 0.0[a] | 0.6 ± 0.1 | 1.4 ± 0.3 | 1.3 ± 0.2 |
| S. parasanguinis | 0.5 ± 0.0[a] | 0.3 ± 0.1 | 1.0 ± 0.3 | 0.9 ± 0.2 |
| S. intermedius | 0 | 0 | 0 | 0 |
| S. gordonii | 1.0 ± 0.7[a] | 0.4 ± 0.2 | 0.6 ± 0.4 | 0.5 ± 0.4 |
| S. australis | 2.2 ± 0.3[a] | 0.9 ± 0.1 | 1.3 ± 0.3 | 1.0 ± 0.5 |
| S. sanguinis | 0.7 ± 0.6[a] | 0.3 ± 0.4 | 0.8 ± 0.6[b] | 0.5 ± 0.4 |
| S. cristatus | 1.0 ± 0.7 | 0.8 ± 0.4 | 0.4 ± 0.4 | 0.5 ± 0.3 |
| By S. mutans UA159 | | | | |
| S. gordonii DL1 | −6.5 ± 0.2[a] | −2.4 ± 0.9 | −1.7 ± 0.3 | −1.6 ± 0.4 |
| S. parasanguinis | −5.6 ± 0.4[a] | −1.2 ± 0.2 | −1.9 ± 0.7 | −1.7 ± 0.6 |
| S. intermedius | −8.0 ± 0 | −7.7 ± 0.6 | −7.6 ± 1.0 | −7.2 ± 1.4 |
| S. gordonii | −5.6 ± 2.1[a] | −1.5 ± 1.5 | −4.8 ± 1.3 | −4.3 ± 1.4 |
| S. australis | −6.3 ± 0.5[a] | −2.7 ± 1.0 | −3.3 ± 0.3 | −4.1 ± 0.4 |
| S. sanguinis | −6.4 ± 2.2[a] | −4.5 ± 2.2 | −4.4 ± 2.3 | −5.3 ± 2.2 |
| S. cristatus | −8.0 ± 0[a] | −4.8 ± 1.9 | −6.5 ± 0.5[b] | −7.6 ± 0.6 |
| Simultaneously | | | | |
| S. gordonii DL1 | 0.7 ± 0.1[a] | 0.4 ± 0.0 | 0.4 ± 0.1 | 0.4 ± 0.0 |
| S. parasanguinis | 0.3 ± 0.1[a] | 0.1 ± 0.1 | 0 | 0 |
| S. intermedius | −4.0 ± 1.2 | −3.7 ± 0.8 | −2.1 ± 0.6 | −2.1 ± 0.5 |
| S. gordonii | 0.6 ± 0.4 | −0.2 ± −0.2 | 0.1 ± 0.3[b] | −0.2 ± 0.4 |
| S. australis | 0.8 ± 0.1 | 1.0 ± 0.3 | 0.3 ± 0.2 | 0.3 ± 0.2 |
| S. sanguinis | 0.3 ± 0.7[a] | −0.1 ± 0.6 | −0.3 ± 0.7[b] | −0.6 ± 0.7 |
| S. cristatus | −0.6 ± 1.1 | −0.4 ± 1.2 | −1.5 ± 1.5[b] | −2.5 ± 1.1 |

For Table 3: Mean average of inhibition zones ± standard deviation (millimeter). The 56 arginolytic strains tested are grouped and listed by their closest relative species. Competition assays occurred as follows: (1) arginolytic strain first followed by S. mutans UA159 24 h later; (2) S. mutans UA159 first followed by arginolytic strain 24 h later, and (3) arginolytic strain and S. mutans UA159 simultaneously. Positive values show that arginolytic strains inhibit the growth of S. mutans UA159 while negative values show that the growth of arginolytic strains was inhibited by S. mutans UA159.
[a]indicates significant differences between TY-25 mM galactose and TY-25 mM glucose inhibition zones in a given species.
[b]indicates significant differences between ½ strength BHI and BHI inhibition zones in a given species (p < 0.05).

TABLE 4

Mean average of growth inhibition zones of arginolytic strains on S. mutans UA159 by type of isolation source.

| Closest relative species | Caries Status | TY-25 mM galactose | TY-25 mM glucose | ½ strength BHI | BHI |
|---|---|---|---|---|---|
| S. gordonii str. Challis substr. CH1 strain | CF | 2.3 ± 0.2* | 0.7 ± 0.1* | 1.3 ± 0.3* | 1.2 ± 0.1* |
|  | CA | 0.6 ± 0.1 | 0.3 ± 0.1 | 0.4 ± 0.1 | 0.3 ± 0.0 |
| S. gordonii strain ATCC 10558 | CF | 1.3 ± 0.2* | 0.6 ± 0.1* | 0.8 ± 0.1* | 0.5 ± 0.1* |
|  | CA | 0.5 ± 0.1 | 0.3 ± 0.1 | 0.4 ± 0.1 | 0.3 ± 0.1 |
| S. sanguinis JCM 5708 | CF | 0.6 ± 0.5* | 0.2 ± 0.3 | 0.6 ± 0.4* | 0.4 ± 0.4 |
|  | CA | 0.3 ± 0.3 | 0.4 ± 0.4 | 0.3 ± 0.2 | 0.3 ± 0.2 |

Mean average of inhibition zones ± standard deviation (millimeter). Isolation source refers to the caries status of the subjects from which the strains were isolated: CF (caries-free) and CA (caries-active).
*indicates statistically significant difference between the inhibition zones of strains isolated from CF versus CA within the same closest relative species and growth media ($p < 0.05$).

TABLE 5

Mean average of growth inhibition zones of arginolytic strains on or by S. mutans UA159.

Table 5 part 2

| Strains | Closest relative species | Caries status | ½ strength BHI | | | BHI | | |
|---|---|---|---|---|---|---|---|---|
| | | | 1 | 2 | 3 | 1 | 2 | 3 |
| DL1 | S. gordonii DL1 |  | 1.4 ± 0.3 | −1.7 ± 0.3 | 0.4 ± 0.1 | 1.3 ± 0.2 | −1.6 ± 0.4 | 0.4 ± 0.0 |
| A1 | S. parasanguinis ChDC B356 | CF | 1.0 ± 0.3 | −1.9 ± 0.7 | 0.0 ± 0.0 | 0.9 ± 0.2 | −1.7 ± 0.6 | 0.0 ± 0.0 |
| A10 | S. gordonii ATCC 10558 | CA | 0.5 ± 0.1 | −4.6 ± 0.3 | 0.2 ± 0.1 | 0.2 ± 0.1 | −3.0 ± 0.0 | 0.1 ± 0.0 |
| A11 | S. gordonii ATCC 10558 | CF | 0.8 ± 0.1 | −4.1 ± 0.4 | 0.2 ± 0.1 | 0.5 ± 0.1 | −4.0 ± 0.4 | −0.9 ± 0.1 |
| A12 | S. australis AI-1 | CF | 1.6 ± 0.1* | −3.3 ± 0.2 | 0.5 ± 0.1* | 1.5 ± 0.2* | −4.1 ± 0.3 | 0.5 ± 0.1* |
| A13 | S. australis AI-1 | CF | 1.1 ± 0.2 | −3.3 ± 0.3 | 0.2 ± 0.1 | 0.5 ± 0.1 | −4.1 ± 0.4 | 0.1 ± 0.1 |
| A17 | S. sanguinis SK36 | CF | 2.0 ± 0.3* | −1.7 ± 0.3 | 0.5 ± 0.1* | 1.0 ± 0.2 | −3.1 ± 0.1 | 0.1 ± 0.0 |
| A42 | S. sanguinis JCM 5708 | CF | 1.3 ± 0.1 | −8.0 ± 0.1 | −2.8 ± 0.2 | 0.9 ± 0.2 | −8.0 ± 0.0 | −0.3 ± 0.1 |
| A49 | S. sanguinis JCM 5708 | CA | 0.0 ± 0.0 | −5.2 ± 0.2 | −0.5 ± 0.1 | 0.0 ± 0.0 | −4.7 ± 0.4 | −0.6 ± 0.1 |
| A52 | S. cristatus ATCC 51100 | CA | 0.9 ± 0.1 | −4.9 ± 0.2 | −2.1 ± 0.4 | 1.2 ± 0.2 | −7.4 ± 1.2 | −2.8 ± 0.4 |
| A55 | S. cristatus F0329 | CA | 0.9 ± 0.1 | −6.5 ± 0.4 | −0.7 ± 0.2 | 0.7 ± 0.2 | −8.0 ± 0.0 | −2.3 ± 0.3 |

Table 5 part 3

| Strains | Closest relative species | Caries status | TY-25 mM galactose | | | TY-25 mM glucose | | |
|---|---|---|---|---|---|---|---|---|
| | | | 1 | 2 | 3 | 1 | 2 | 3 |
| DL1 | S. gordonii DL1 |  | 0.7 ± 0.0 | −6.5 ± 0.2 | 0.7 ± 0.1 | 0.6 ± 0.1 | −2.4 ± 0.9 | 0.4 ± 0.0 |
| A1 | S. parasanguinis ChDC B356 | CF | 0.5 ± 0.0 | −5.6 ± 0.4 | 0.0 ± 0.0 | 0.3 ± 0.1 | −1.2 ± 0.2 | 0.0 ± 0.0 |
| A10 | S. gordonii ATCC 10558 | CA | 0.5 ± 0.1 | −7.2 ± 0.1 | 0.4 ± 0.1 | 0.4 ± 0.1 | −0.5 ± 0.1 | 0.2 ± 0.0 |
| A11 | S. gordonii ATCC 10558 | CF | 1.3 ± 0.2* | −4.0 ± 0.0 | 0.3 ± 0.1 | 0.6 ± 0.1 | −4.0 ± 0.0 | 0.3 ± 0.1 |
| A12 | S. australis AI-1 | CF | 2.1 ± 0.1* | −6.5 ± 0.6 | 0.9 ± 0.1* | 0.9 ± 0.1* | −3.5 ± 0.4 | 1.2 ± 0.1* |
| A13 | S. australis AI-1 | CF | 2.3 ± 0.4* | −6.0 ± 0.2 | 0.7 ± 0.1 | 0.8 ± 0.0* | −1.6 ± 0.3 | 0.7 ± 0.1* |
| A17 | S. sanguinis SK36 | CF | 2.1 ± 0.2* | −1.0 ± 0.3 | 1.3 ± 0.1* | 1.5 ± 0.2* | −1.5 ± 0.3 | 0.4 ± 0.0 |
| A42 | S. sanguinis JCM 5708 | CF | 1.2 ± 0.1* | −6.8 ± 0.3 | 0.6 ± 0.6 | 0.6 ± 0.1 | −8.0 ± 0.0 | −2.1 ± 0.2 |
| A49 | S. sanguinis JCM 5708 | CA | 0.0 ± 0.0 | −6.9 ± 0.2 | 0.0 ± 0.0 | 0.0 ± 0.0 | −3.4 ± 0.5 | −0.5 ± 0.1 |
| A52 | S. cristatus ATCC 51100 | CA | 1.6 ± 0.1* | −8.0 ± 0.0 | −1.9 ± 0.5 | 1.7 ± 0.3* | −4.0 ± 0.0 | −0.5 ± 0.1 |
| A55 | S. cristatus F0329 | CA | 1.7 ± 0.1* | −8.0 ± 0.0 | 0.4 ± 0.1 | 0.9 ± 0.1* | −4.0 ± 0.0 | 0.6 ± 0.1* |

Table 5 part 1

| Strains | Closest relative species | Caries status | TY-D-25 mM galactose aerobic | | | TY-D-25 mM galactose anaerobic | | |
|---|---|---|---|---|---|---|---|---|
| | | | 1 | 2 | 3 | 1 | 2 | 3 |
| DL1 | S. gordonii DL1 |  | 1.7 ± 0.2 | −3.2 ± 0.2 | 0.9 ± 0.1 | 0.0 ± 0.0 | −1.0 ± 0.1 | 0.0 ± 0.0 |
| A1 | S. parasanguinis ChDC B356 | CF | 2.2 ± 0.7* | −4.6 ± 0.9 | 2.0 ± 0.5* | 1.0 ± 0.1* | −1.6 ± 0.1 | 0.0 ± 0.0 |
| A10 | S. gordonii ATCC 10558 | CA | 0.4 ± 0.1 | −5.0 ± 2.0 | 0.6 ± 0.3 | 0.0 ± 0.0 | −0.5 ± 0.0 | 0.0 ± 0.0 |
| A11 | S. gordonii ATCC 10558 | CF | 2.0 ± 0.1* | −4.7 ± 0.7 | 1.0 ± 0.2* | 0.5 ± 0.5* | −0.8 ± 0.3 | 0.0 ± 0.0 |
| A12 | S. australis AI-1 | CF | 2.6 ± 0.7* | −4.4 ± 1.5 | 1.6 ± 0.2* | 0.4 ± 0.1 | −2.0 ± 0.0 | 0.0 ± 0.0 |
| A13 | S. australis AI-1 | CF | 2.4 ± 0.7* | −4.3 ± 1.5 | 1.4 ± 0.2* | 0.2 ± 0.1* | −1.8 ± 0.0 | 0.0 ± 0.0 |
| A17 | S. sanguinis SK36 | CF | 1.4 ± 0.3 | −4.6 ± 1.1 | 1.3 ± 0.3* | 0.4 ± 0.1* | 2.0 ± 0.1 | 0.3 ± 0.1* |
| A42 | S. sanguinis JCM 5708 | CF | 1.1 ± 0.3 | −8.0 ± 0.0 | 0.7 ± 0.5 | 0.2 ± 0.3* | −6 ± 0.33 | −1.2 ± 0.3 |
| A49 | S. sanguinis JCM 5708 | CA | 0.0 ± 0.0 | −5.6 ± 0.5 | 0.5 ± 0.2 | 0.0 ± 0.0 | −3.3 ± 0.2 | 0.0 ± 0.0 |

TABLE 5-continued

Mean average of growth inhibition zones of arginolytic strains on or by S. mutans UA159.

| A52 | S. cristatus ATCC 51100 | CA | 3.1 ± 0.3* | −7.1 ± 0.4 | 1.8 ± 0.6* | 0.3 ± 0.0* | −5.6 ± 0.5 | −0.8 ± 0.9 |
| A55 | S. cristatus F0329 | CA | 1.3 ± 0.1 | −8.0 ± 0.0 | 2.0 ± 0.6* | 0.5 ± 0.1* | −5.7 ± 0.5 | −1.2 ± 0.7 |

Table 5 (legend):
mean average of inhibition zones ± standard deviation (millimeter).
Competition assays occurred as follows:
(1) arginolytic strain first followed by S. mutans UA159 24 h later;
(2) S. mutans UA159 first followed by arginolytic strain 24 h later, and
(3) arginolytic strain and S. mutans UA159 simultaneously.
Positive values show that arginolytic strains inhibit the growth of S. mutans UA159 while negative values show that the growth of arginolytic strains was inhibited by S. mutans UA159.
*indicates that the inhibition zone of the arginolytic clinical strain on S. mutans UA159 is greater than that of S. gordonii DL1 on S. mutans UA159 in a given growth media ($p < 0.05$).

Table 5 shows the mean average of the zones of growth inhibition on and by S. mutans of 10 arginolytic strains that were chosen to investigate in more detail some environmental factors that may affect their antagonistic capacities. All strains inhibited the growth of S. mutans to different degrees when inoculated first, except for A49 (best 16S match: S. sanguinis JCM 5708). Growth in TY-25 mM galactose, half-strength BHI or TY-D-25 mM galactose under aerobic conditions appeared to favor the antagonistic effects of most arginolytic strains against S. mutans when they were inoculated first. S. mutans inhibited the growth of all arginolytic strains when it was inoculated first, especially in aerobic conditions. All strains inhibited the growth of S. mutans to differing degrees when inoculated simultaneously with UA159 on TY-25 mM galactose, expect for A52 (best 16S match: S. cristatus ATCC 51100). However, all strains, including A52, inhibited the growth of S. mutans when inoculated simultaneously with UA159 on TY-D-25 mM galactose under aerobic conditions.

Factors Affecting the Antagonistic Capacity of Arginolytic Bacteria.

Carbohydrate source. To explore how the source of carbohydrate on which the organisms were grown affected the antagonistic capacity of the arginolytic strains on or by S. mutans, the zones of inhibition on TY-25 mM galactose were compared to those on TY-25 mM glucose agar plates (Tables 3 and 5). Clearly, a stronger antagonistic capacity against S. mutans was observed when the strains were grown on galactose.

Nutrient Availability.

Figure 4:
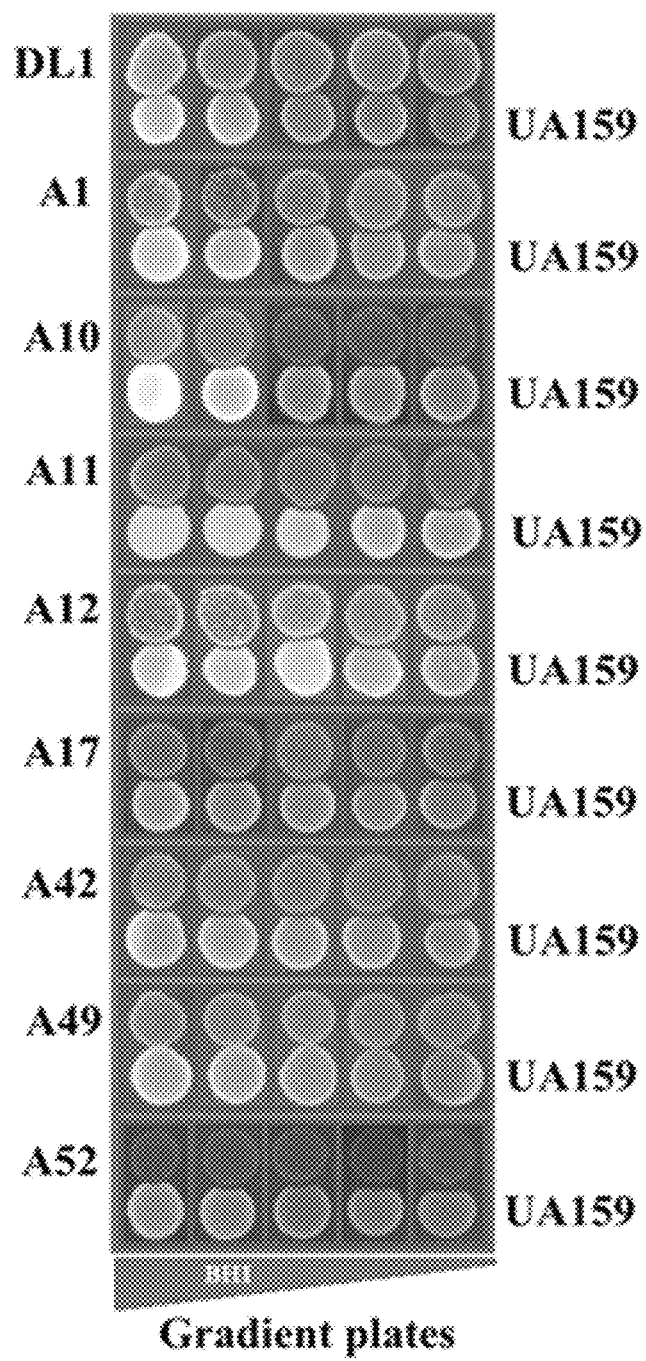
FIG. 4 illustrates an image of growth inhibition of arginolytic strains on *S. mutans* UA159 using gradient BHI plates. Arginolytic strains were spotted first, and *S. mutans* was spotted 24 hr later.

Interbacterial antagonism was evaluated in diluted and modified versions of the full-strength media tested. The concentration of nutrients affected antagonistic interactions, with greater antagonism of S. mutans being evident on TY-D-25 mM galactose agar, compared to that seen on full-strength TY-25 mM galactose (Table 5); TY-D contains 1/3 of the tryptone and yeast extract found in TY medium. For example, S. parasanguinis A1 could not inhibit S. mutans when inoculated simultaneously onto TY-25 mM galactose, but displayed strong inhibitory effects on UA159 onto TY-D-25 mM galactose agar. An increased antagonistic capacity against UA159 was also observed when S. gordonii A11, S. australis A13, and S. cristatus A52 were inoculated simultaneously with S. mutans onto TY-D-25 mM galactose agar. Gradient TY-25 mM galactose (25 agar plates were also used, and larger inhibition zones were evident in the regions of the plates that contained lower nutrient concentrations (FIG. 4). Specifically, growth of S. mutans was completely inhibited by S. sanguinis A17 and A42 (FIG. 4) in the area of the plates containing lower concentrations of nutrients.

Saliva agar plates supplemented with galactose or glucose, and with or without arginine, were used to mimic nutritional conditions in the oral cavity. All strains displayed substantial antagonistic capacity against S. mutans on saliva agar (FIG. 5), but antagonism was more pronounced when galactose was the primary carbohydrate source, as compared with glucose. The addition of arginine to the saliva plates clearly enhanced the antagonistic capacity of the strains, especially when the medium was supplemented with galactose instead of glucose. The table below shows the mean average of inhibition zones±standard deviation (millimeter) from the gradient plates in FIG. 5. (*) indicates that the inhibition zone of the arginolytic strain on S. mutans UA159 is significant different compared to S. gordonii DL1 in a given growth condition.

TABLE 6

Figure 5:
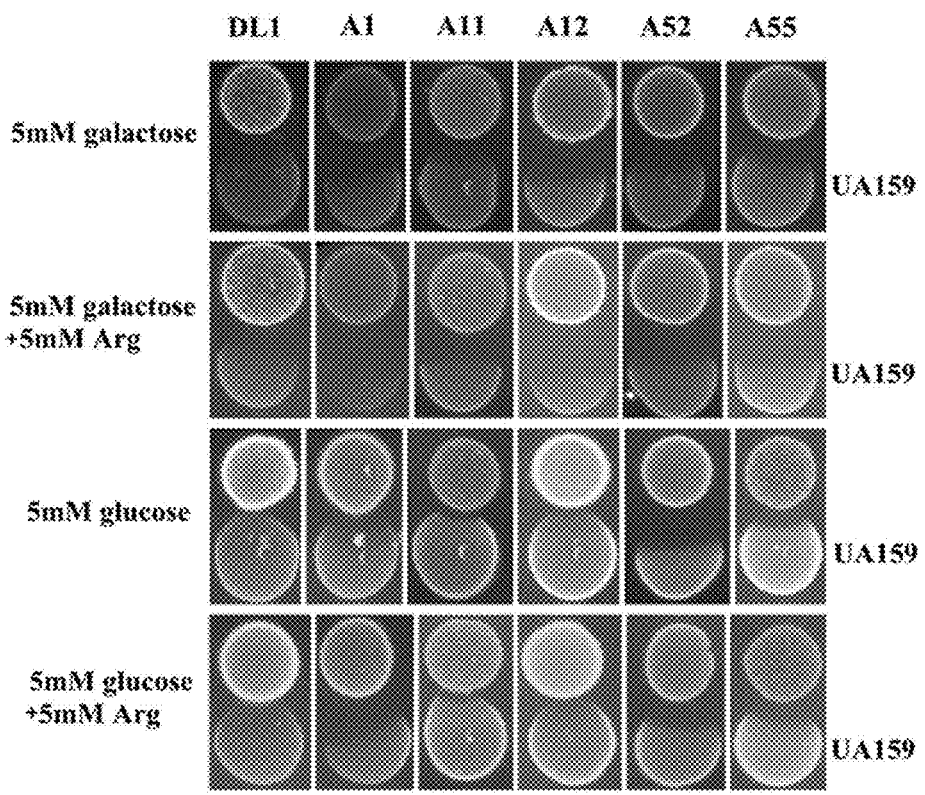
FIG. 5 illustrates growth inhibition zones of arginolytic strains on *S. mutans* UA159 on saliva agar plates under different growth conditions. Arginolytic strains were inoculated first and *S. mutans* UA159 was inoculated 24 h later. Table 6, below, shows the mean average of inhibition zones±standard deviation (millimeter).

(corresponding to FIG. 5)

| | DL1 | A1 | A11 | A12 | A52 | A55 |
|---|---|---|---|---|---|---|
| 5 mM galactose | 2.6 ± 0.1 | 3.0 ± 0.1 | 1.9 ± 0.2** | 3.1 ± 0.1 | 2.7 ± 0.3 | 2.4 ± 0.2 |
| 5 mM galactose + 5 mM Arg | 2.4 ± 0.2 | 6.3 ± 0.4*** | 2.4 ± 0.5 | 3.9 ± 0.9 | 3.2 ± 0.0 | 3.1 ± 0.6 |
| 5 mM glucose | 0.8 ± 0.1 | 1.9 ± 0.1*** | 1.3 ± 0.1* | 1.2 ± 0.1* | 3.6 ± 1.4*** | 1.6 ± 0.1** |
| 5 mM glucose + 5 mM Arg | 1.9 ± 0.1 | 3.3 ± 0.2*** | 1.1 ± 0.1** | 1.9 ± 0.1 | 2.6 ± 0.1** | 2.1 ± 0.0 |

Oxygen.

While anaerobes do persist, and in some cases thrive in the oral cavity, the microorganisms in all habitats of the human mouth are exposed continuously to relatively high concentrations of oxygen. To explore how the presence of oxygen influenced the antagonistic capacity of the arginolytic strains on and by S. mutans, growth on TY-D-25 mM galactose was compared under aerobic and anaerobic conditions (Table 5). In all cases, growth in aerobic conditions favors the antagonistic capacity of the arginolytic strains against UA159.

$H_2O_2$ is an Antagonistic Compound Produced by the Arginolytic Isolates.

Figure 6A:
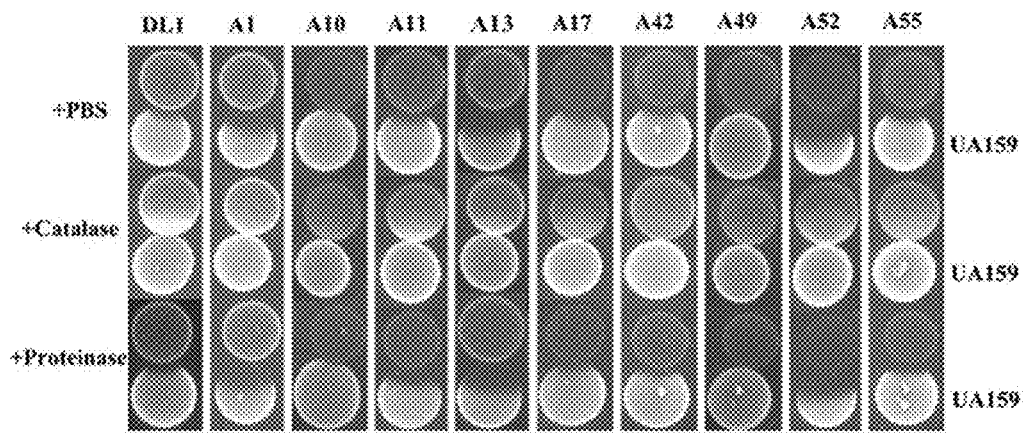
FIGS. 6A-6B illustrate characterization of a growth inhibitory substance produced by arginolytic strains on a dilute version of TY (TY-D; 1% tryptone and 0.2% yeast extract) agar plates supplemented with 25 mM galactose.
Figure 6B:
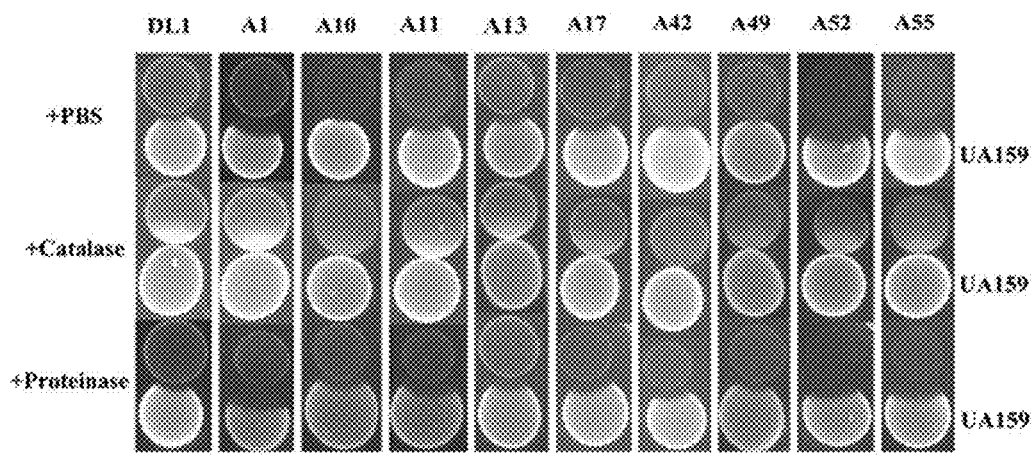
Figure 7D:
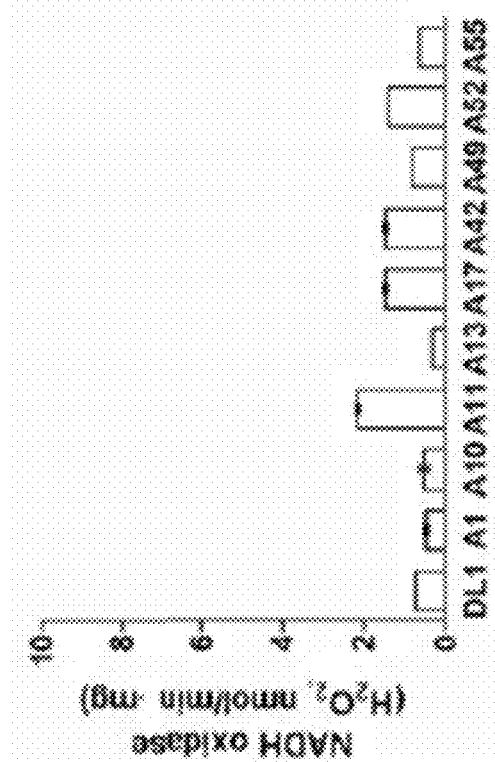
Figure 7E:
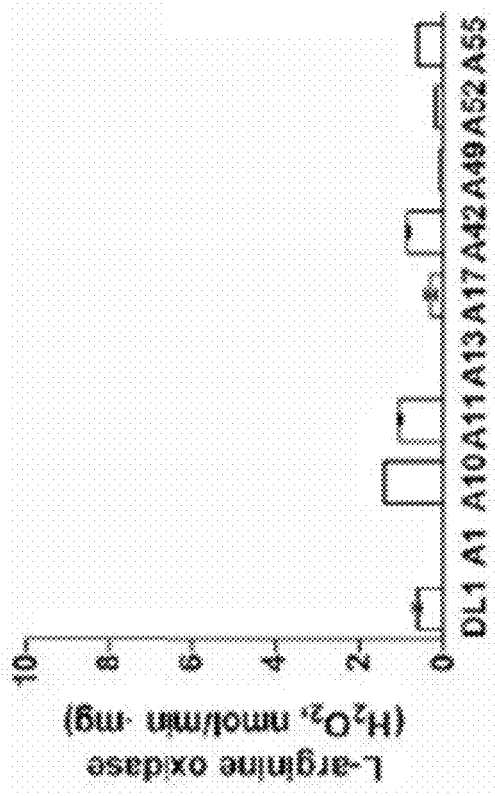

FIGS. 6A-6B illustrate the zones of growth inhibition of the arginolytic strains on and by *S. mutans* UA159 on agar plats containing catalase or proteinase K, or an equivalent amount of the carrier (PBS) used for these enzymes as control. Irrespective of the inoculation order of commensals and *S. mutans*, no zones of inhibition were observed in media containing catalase. FIGS. 7A-7E show that there was substantial variation in the capacity of the different strains to produce $H_2O_2$ under the conditions tested. Two-way ANOVA supported that the type of strain and the growth conditions influenced the production of $H_2O_2$ ($p<0.001$; FIG. 7A). Generally speaking, greater levels of $H_2O_2$ were measured after growth in TY-D-25 mM galactose broth, as compared to TY-25 mM galactose broth ($p=0.002$) and TY-25 mM glucose broth ($p<0.001$). The presence of glucose inhibited $H_2O_2$ production by all strains compared to galactose ($p=0.022$). Of note, the strains A52 (best 16S match: *S. cristatus* ATCC 51100) and A55 (best 16S match: *S. cristatus* F0329) produced significantly more $H_2O_2$ compared to the other strains in all growth conditions tested ($p<0.001$).

To determine the primary metabolic pathways for the production of $H_2O_2$ by the commensal streptococci, the activity of various $H_2O_2$-generating oxidases was assayed as detailed in the methods section (FIGS. 7B-E). The strains *S. parasanguinis* A1, *S. gordonii* A10, *S. australis* A13, *S. sanguinis* A42, *S. cristatus* A52 and *S. cristatus* A55 presented with higher levels of pyruvate oxidase activity, compared to the reference strain of *S. gordonii*, DL1 ($p<0.001$). *S. gordonii* A10 and A11, and *S. cristatus* A52 and A55 also produced significant quantities of lactate oxidase, which during the conversion of lactate to pyruvate generates $H_2O_2$. All strains produced very low levels of L-arginine oxidase activity and NADH oxidase activity under the growth conditions tested.

*S. mutans* UA159 Inhibits the Growth of Arginolytic Bacteria when Inoculated First.

*S. mutans* UA159 appeared to be able to inhibit the growth of the arginolytic strains when inoculated first, albeit to differing degrees. Strains of *S. cristatus* and *S. intermedius* appeared to be more sensitive to inhibition by UA159 compared to *S. parasanguinis*, *S. gordonii* and *S. australis* (Tables 3 and 5). Table 5 and FIGS. 8A-8C show that the antagonistic capacity of UA159 on the arginolytic strains was also affected by the carbohydrate source, richness of the medium, and presence of arginine or oxygen. Table 5 shows that oxygen favors the antagonistic capacity of *S. mutans* against the arginolytic strains, which is consistent with the observation that growth in an aerobic conditions induces mutacin gene expression. Arginine was shown to significantly enhance the resistance of arginolytic strains to inhibition by *S. mutans* during growth in either aerobic or anaerobic conditions. Significantly smaller zones of inhibition were elicited by *S. mutans* against the arginolytic strains during aerobic growth in the presence of arginine, as compared to growth without arginine ($p<0.01$), with the exception of *S. sanguinis* A42 and *S. cristatus* A55 ($p>0.05$). FIG. 8C shows no zones of inhibition of *S. mutans* with *S. gordonii* A11, or with *S. australis* A12 or *S. cristatus* A52 during anaerobic growth in the presence of arginine ($p<0.001$).

Discussion

The application of new molecular methodologies, such as next-generation sequencing, to the study of the human oral microbiome has revealed remarkable diversity in the microbiota in oral biofilms. Inherent to the ecological view of any natural environment is that bacterial populations evolve competitive and cooperative strategies to survive and persist. However, the evolutionary mechanisms that select for and maintain traits that benefit certain bacteria and populations in the oral cavity, ultimately affecting dental health, are not well characterized. This study investigated the antagonistic potential of a spectrum of low-passage clinical isolates of commensal arginolytic strains against and by the strongly cariogenic and well-characterized human isolate *S. mutans* UA159. Although previous studies have demonstrated the antagonistic capacity of laboratory strains of *S. gordonii* and *S. sanguinis* against *S. mutans* (Kreth et al., 2005; Kreth et al., 2008; Zhu and Kreth, 2012)], to our knowledge, this study is the first to focus on a diverse group of clinical isolates of known arginine metabolic capacity to compete with a cariogenic bacterium. Not only was there a great degree of heterogeneity in the capacity of strains to compete with *S. mutans*, but also the order in which the organisms were established and environmental factors greatly influenced the outcomes of interbacterial interactions. *S. mutans* UA159 consistently inhibited the growth of arginolytic bacteria when it was allowed to become established prior to inoculation of the commensal organisms. However, some arginolytic bacteria could also inhibit the growth of UA159 when they were inoculated first or simultaneously with UA159. Importantly, most of the arginolytic bacteria studied here, such as *S. sanguinis*, *S. parasanguinis*, *S. gordonii*, and *S. cristatus* are pioneer colonizers of the tooth surfaces and therefore have the potential to become established on the teeth prior to acquisition of *S. mutans*. In fact, early colonization of *S. sanguinis* in the oral cavity of infants was shown to delay the colonization of *mutans* streptococci (Caufield et al., 2000), which in turn has been associated with lower caries prevalence in the primary (Kohler et al., 1988) and permanent dentition (Kohler and Andreen, 2012). Thus, early establishment on tooth surfaces of strongly arginolytic strains with high capacities to compete with *S. mutans* in oral biofilms may be a potent deterrent to the initiation of carious lesions.

Long-term persistence of an organism in a complex ecosystem requires effective mechanisms to prevent being dominated or eliminated by competitors. In the context of dental caries, lesions begin to form on tooth surfaces when the cycles of acidification outweigh those of alkalization of oral biofilms; driving the eventual emergence of a more aciduric microflora and lowers biofilm pH values levels that results in a net loss of tooth mineral. Metabolic activities by oral bacteria that help to promote a more neutral pH and to prevent the outgrowth of cariogenic species should have a strong anti-caries effect. Importantly, ammonia production from arginine metabolism is a typical example of a strategy used by many abundant oral streptococci to survive acidification of oral biofilms and to compete with bacteria in oral biofilms that can better tolerate acidic conditions. A microflora that is both robustly arginolytic and capable of interfering with the colonization, growth or expression of virulence attributes of *S. mutans* should be beneficial to the host.

In this study, the antagonistic capacity of the arginolytic strains on *S. mutans* UA159 varied between different species, between isolates of the same taxa, and between strains isolated from subjects of different caries status. A wide spectrum of antagonistic capacity against *S. mutans* was observed among strains of *S. intermedius, S. sanguinis, S. parasanguinis, S. gordonii, S. australis* and *S. cristatus*. More specifically, strains of *S. intermedius* showed no antagonistic capacity against *S. mutans*, whereas strains of *S. australis* showed the highest capacity to inhibit the growth of *S. mutans* when inoculated first or simultaneously on the different media tested. Furthermore, two strains of *S. sanguinis* isolated from a CF subject, most similar in 16S sequence to SK36 and ChDC B357, also presented different antagonistic capacities against *S. mutans*. A strain of *S. gordonii* (A8, 16S most similar to str. Challis substr. CH1) isolated from a CF subject presented greater inhibitory effect on *S. mutans* compared to a similar strain (A7) isolated from a CA subject. In fact, strains isolated from CF subjects generally displayed stronger antagonistic capacity against *S. mutans* than those from CA subjects. This observation provides support for the position that there is significant heterogeneity in the phenotypic capabilities across and within species of oral bacteria that can impact their influence on oral health and caries development. Efforts on comprehensive comparative genomics of abundant commensals associated with CA and CF individuals can be expanded and used to establish whether there are genotypes or clearly definable genetic differences that can allow for the discrimination of commensals that are beneficial from those that are merely not harmful, or that may be overtly harmful.

Mutacin production by *S. mutans*, ADS expression and $H_2O_2$ production by commensal oral streptococci, and a variety of other factors that may influence the persistence of these species in oral biofilms are subject to regulation by environmental inputs and other signals. The findings presented here clearly show that nutrient source and availability, oxygen and other factors (e.g. factors susceptible to proteinase K) affect the competition between commensal/beneficial streptococci and a caries pathogen. During fasting periods, galactose is one of the more abundant carbohydrates secreted into the oral cavity, and certain commensal streptococci have a higher capacity to transport and metabolize galactose than most *S. mutans* isolates (Zeng et al., 2012). Periodic ingestion of dietary carbohydrates provides other carbohydrates to oral bacteria, such as glucose, which leads to rapid acid production by *S. mutans*, but can also leads to repression of ADS gene expression via carbohydrate catabolite repression (CCR). Moreover, $H_2O_2$ production may also be down-regulated by CCR (Zheng et al., 2011). The findings of the present example revealed greater inhibition of growth of *S. mutans* by arginolytic strains and higher levels of $H_2O_2$ production when cells were grown with galactose as the primary carbohydrate source, compared to glucose. Other factors favoring the antagonistic capacity of, and $H_2O_2$ production by, arginolytic bacteria included decreased availability of nutrients in tryptone and/or yeast extract, and the presence of arginine or oxygen. Particularly, arginine has been recently shown to influence the architecture and physicochemical properties of the biofilm matrix formed in mixed cultures of *S. mutans* UA159 and *S. gordonii* DL1 (He et al., 2016). Arginine decreased the expression of gtfB, encoding an enzyme involved in water-insoluble glucan synthesis, and a bacteriocin (SMU.150), while increasing the expression of spxB of *S. gordonii*, which produces $H_2O_2$ from pyruvate.

These findings expand our knowledge of the effects of arginine metabolism on the ecology of oral biofilms, and clearly demonstrate that there is heterogeneity among commensal streptococci in their arginolytic and antagonism capacities, which cannot be discerned simply by 16S sequence comparisons. Certain commensals may have a particularly beneficial impact on the ecology of oral biofilms by synergistically moderating plaque pH and antagonizing the growth and virulence of caries pathogens, and perhaps periodontal pathogens, through $H_2O_2$ production and other metabolic mechanisms. Of significant clinical relevance, this approach coupled with analysis of the genomes of these organisms can guide the formulation of probiotic preparations composed of beneficial commensals for control of oral diseases.

Example 3

Characterization of a *Streptococcus* A12

As demonstrated in the examples above, the ability of certain oral biofilm bacteria to moderate pH through arginine metabolism by the arginine deiminase system (ADS) is a deterrent to the development of dental caries. The present example further characterized a novel *Streptococcus*, designated A12, isolated from supragingival dental plaque of a caries-free individual (deposited on Mar. 9, 2017 with ATCC under designation PTA-123884). As set forth in Examples 1 and 2, above, A12 not only expressed the ADS pathway at high levels under a variety of conditions, but also effectively inhibited growth of *S. mutans*. The complete genome sequence of A12 was determined and phylogenomic analyses compared A12 to streptococcal reference genomes. A12 was most similar to *Streptococcus australis* and *Streptococcus parasanguinis*, but sufficiently different that it may represent a new species. A12-like organisms may play crucial roles in promotion of stable, health-associated oral biofilm communities by moderating plaque pH and interfering with the growth and virulence of caries pathogens.

Materials and Methods

Bacterial Strains, Growth Conditions, and Reagents.

The bacterial strains and plasmids used in this study are shown in Table 7. A12 was isolated from supragingival plaque of a CF subject. *Escherichia coli* DH5a was grown in Luria broth. A12, *S. mutans* UA159 and derivatives of these strains were routinely grown in brain heart infusion (BHI, 3.7%) broth or BHI agar plates (Difco), or in the chemically defined medium FMC.

TABLE 7

Bacterial strains and plasmids used in this study

| Strain or plasmid | Relevant characteristic(s) | Source or reference |
| --- | --- | --- |
| Stains | | |
| *Escherichia coli* DH5α | | Lab stock |
| *S. mutans* UA159 | *S. mutans* wild-type reference strain | Lab stock (ATCC 700610) |
| *S. gordonii* DL1 | *S. gordonii* wild-type reference strain | Lab stock |
| *S. sanguinis* SK150 | *S. sanguinis* wild-type reference strain | Lab stock |

TABLE 7-continued

Bacterial strains and plasmids used in this study

| Strain or plasmid | Relevant characteristic(s) | Source or reference |
|---|---|---|
| A12 | Isolated from supragingival dental plaque of caries-free subject | Clinical strain (48) |
| SAB358 | S. mutans UA159::P$_{comX}$-lacZ; Km$^r$ | (36) |
| SAB249 | S. mutans UA159::P$_{cipB}$-lacZ; Km$^r$ | This study |
|  | S. mutans UA159::pBGS; Sp$^r$ | This study |
|  | S. gordonii DL1ΔarcR; Km$^r$ | (47) |
|  | S. gordonii DL1Δsgc; Em$^r$ | This study |
|  | Streptococcus gordonii DL1ΔspxB; Km$^r$ | This study |
|  | Streptococcus gordonii DL1Δsgc spxB; Em$^r$ Km$^r$ | This study |
|  | A12ΔarcR; Em$^r$ | This study |
|  | A12Δsgc; Em$^r$ | This study |
|  | A12ΔspxB; Km$^r$ | This study |
|  | A12Δsgc spxB; Em$^r$ Km$^r$ | This study |
| Plasmid |  |  |
| pVA838 | Escherichia coli-Streptococcus shuttle vector; Em$^r$ |  |
| pJL184 | Escherichia coli Streptococcus shuttle vector; Km$^r$ | (45) |
| pDL278 | Escherichia coli-Streptococcus shuttle vector; Sp$^r$ | (52) |
| pBGS | Escherichia coli-Streptococcus shuttle vector; Sp$^r$ |  | a. Km, kanamycin; Em, erythromycin; Sp, spectinomycin.
b. In A12, arcR, sgc and spxB are the homologs of arcR, sgc and spxB gene of S. gordonii, respectively Multiple media formulations were developed empirically to examine the effects of carbohydrate-source and nutrient availability on interspecies interactions: i) TY (3% tryptone, 0.5% yeast extract) agar plates were supplemented with 25 mM galactose or 25 mM glucose, ii) a more dilute version of TY (TY-D; 1% tryptone, 0.2% yeast extract) agar plates supplemented with 25 mM galactose, or iii) half-strength BHI (1.85% BHI). For the selection of antibiotic-resistant colonies after genetic transformation or for enumeration of bacteria from mixed cultures, erythromycin (300 μg ml$^{-1}$ for E. coli or 12 μg ml$^{-1}$ for S. mutans), kanamycin (50 μg ml$^{-1}$ for E. coli or 1 mg ml$^{-1}$ for S. mutans) or spectinomycin (50 μg ml$^{-1}$ for E. coli or 1 mg ml$^{-1}$ for S. mutans) was added to the medium. Unless noted otherwise, cultures were grown overnight in BHI medium, with antibiotics when necessary, at 37° C. in a 5% CO$_2$ aerobic atmosphere.

Synthetic CSP (sCSP), corresponding to the 21-aa peptide (Hossain, et al., 2012 and Guo, et al., 2014 incorporated by reference herein), was synthesized by the Interdisciplinary Center for Biotechnology Research (ICBR) facility at University of Florida and its purity was confirmed by high performance liquid chromatography (HPLC). Synthetic XIP (sXIP), corresponding to residues 11-17 of ComS (aa sequence=GLDVWVSL), was synthesized and purified to 96% homogeneity by NeoBioSci (Cambridge, Mass., USA). The lyophilized sXIP was reconstituted in 99.7% dimethyl sulfoxide (DMSO) to a final concentration of 2 mM and stored in 40 μl aliquots at −20° C.

Construction of Mutant Strains and Reporter Gene Fusions.

Mutant strains of A12 were constructed by double crossover recombination using linear DNA engineered to replace the gene of interest with an antibiotic resistance gene. Briefly, using a colony of A12 as template, 0.5-kbp fragments upstream and downstream of the genes of interest were amplified by PCR using primers (SEQ ID NOs: 3-20 in Table 8, below) based on the genome sequence of A12. Antibiotic resistance markers were amplified by PCR from pJL184 (Km$^R$) or pVA838 (Em$^R$). Each PCR product was gel purified and 100 ng of each fragment were fused using PCR, as described in Palmer, et al., 2012, hereby incorporated by reference herein. PCR products were excised from an agarose gel, purified, and used to transform A12 using a modification of a method originally developed for Streptococcus australis and described in Warburton, et al., 2013, incorporated herein by reference. Briefly, a single colony was inoculated into Todd-Hewitt broth (THB) containing 10% heat-inactivated horse serum and incubated for 16-18 h. Cells were diluted 1/40 into THB supplemented with 10% horse serum and incubated until the OD$_{600}$ reached 0.05 to 0.08. PCR products to be used for gene inactivation (0.5 μg) were added to the cultures and incubation was continued for 3 h. Plasmid DNA (pDL278) was used as a positive control to ensure cells were competent for transformation. Cultures were plated onto BHI agar plates containing the desired antibiotics. Transformants were verified by PCR and DNA sequencing, including sequencing the regions used for recombination to confirm that no unwanted mutations had been introduced into flanking genes. Mutant derivatives of S. gordonii DL1 were constructed using similar methods.

To construct a strain of S. mutans with a lacZ gene fused to the promoter of the cipB bacteriocin gene (PcipB::lacZ; strain SAB249), the promoter region of cipB was amplified using primers (SEQ ID NOs: 21 and 22, in Table 8, below) that incorporated SacI and BamHI sites and cloned into a pMC340B-based lacZ reporter vector, which carries a kanamycin resistance gene (Km$^r$). The vector has sequence homology to the mt/A and phnA genes flanking the cloning sites, allowing for integration of the PcipB-lacZ construct in single copy in the S. mutans chromosome through double crossover homologous recombination. The PcipB-lacZ construct was transformed into the wild-type strain and the correct integration and sequence of the gene fusion was verified by PCR and DNA sequencing. To create a marked strain for co-culture experiments, S. mutans was transformed with pBGS, a spectinomycin-resistant (Sp$^r$) derivative of pBGK in which the kanamycin resistant (Km$^r$) marker was replaced with a Sp$^r$ marker. Transformation of S. mutans UA159 with pBGS allowed for stable integration of the Sp$^r$ marker into the gffA gene (Wen, et al., 2001, incorporated by reference herein), a non-essential gene that does not adversely affect growth or competitive fitness of S. mutans, to create strain S. mutans UA159::pBGS.

Ads Activity.

ADS activity was measured by monitoring citrulline production from arginine using protocols described in Example 1, above. ADS activity was measured in cells grown as follows: overnight cultures of each strain were diluted 1:20 into fresh TY medium containing 25 mM galactose, with or without 10 mM arginine, and incubated as above until the $OD_{600}$ reached 0.5-0.6. The cells were then permeabilized using 1/10 volume of toluene:acetone (1:9) prior to determination of their ADS activity. The concentration of protein in the permeabilized cell preparations was measured using a Pierce BCA protein assay kit (Waltham, Mass., USA) with bovine serum albumin as the standard. ADS activity levels of bacterial strains were normalized to protein content and defined as nmol of citrulline generated× [minute×(mg protein)]$^{-1}$. Alternatively, cells were cultivated in FMC medium containing arginine in concentrations ranging from 0 to 100 mM. Dilutions, incubation, cell preparation and ADS assays for cells grown in FMC were the same as those for cells grown in TY.

Measurement of $H_2O_2$.

Overnight cultures of bacterial strains were diluted 1:20 into TY-25 mM glucose, TY-25 mM galactose or TY-D-25 mM galactose and incubated statically in a 5% $CO_2$ aerobic atmosphere. When the cultures reached an $OD_{600}$ of 0.3, they were shaken at 200 RPM for 30 min and the $H_2O_2$ present in culture supernates was measured as described in Tong, et al., 2007 (incorporated herein by reference) with minor modifications: 0.65 mL of culture supernate was added to 0.6 ml of a solution containing 2.5 mM 4-aminoantipyrine (4-amino-2,3-dimethyl-1-phenyl-3-pyrazolin-5-one; Sigma) and 0.17 M phenol (Fisher). The reaction was allowed to proceed for 4 min at room temperature and then horseradish peroxidase (Pierce, Thermo Scientific) in 0.2 M potassium phosphate buffer (pH 7.2) was added to the reaction at a final concentration of 13 mU/ml. After a 20 min incubation at room temperature, the absorbance at $OD_{510}$ was measured in a Beckman DU-640 spectrophotometer. A standard curve was generated for each assay with known concentrations of $H_2O_2$ (Fisher Scientific).

Assays for $H_2O_2$-Generating Oxidase Enzymes.

Overnight cultures were centrifuged at 4,000×g for 10 min and washed twice with 2 mL of phosphate-buffered saline (PBS, pH 7.3, 137 mM NaCl, 2.7 mM KCl, 4.3 mM $Na_2HPO_4.7H_2O$, 1.4 mM $KH_2PO_4$). The pelleted cells were resuspended in 2 mL PBS. Aliquots of the cell suspension were used for determining lactate oxidase activity and the remaining cell suspensions were permeabilized for determination of pyruvate oxidase, L-arginine oxidase and NADH oxidase activities by mixing the cell suspension with 0.02 volumes of toluene-acetone (1:9, vol/vol) and vortexing for 2 min. The concentration of protein in the cell preparations was determined using a Pierce BCA protein assay kit (Waltham, Mass., USA) with bovine serum albumin as the standard.

Pyruvate oxidase activity was determined by measuring the production of acetyl phosphate. Briefly, the reaction mixture consisted of 0.45 ml of the permeabilized cell suspension and 0.45 ml of a solution containing 50 mM potassium phosphate buffer (pH 6.0), 10 µM $MgCl_2$, 0.2 µM thiamine pyrophosphate (Sigma), 50 mM potassium pyruvate, and 12 µM flavin adenine dinucleotide (FAD; Sigma). Reaction mixtures lacking permeabilized cells or pyruvate were included as negative controls. The reaction mixtures were incubated at 37° C. for 30 min with shaking at a speed of 250 RPM and then the amount of acetyl phosphate generated during the reaction was measured as follows. An aliquot of cell suspensions (0.3 ml) was pre-incubated at 37° C. for 1 min in a heat block, Model 111002 (Boekel Scientific, Feasterville, Pa., USA). Fifty µL of 2 M hydroxylamine hydrochloride solution was added, the mixture was placed into a heat block at 60° C. and incubated for 5 min. Then, 100 µL of development solution consisting of equal volumes of 0.5 M ferric chloride in 5 M HCl and 30% trichloroacetic acid was added and color was allowed to develop for at least one minute at room temperature. The samples were centrifuged and the absorbance at $OD_{540}$ was measured. A standard curve was generated with known concentrations of lithium potassium acetyl phosphate (Sigma).

Lactate oxidase, L-arginine oxidase and NADH oxidase activities were assessed by assaying $H_2O_2$ production. For the lactate oxidase assay, 0.45 ml of intact cells were added to 0.45 ml of 0.2 M sodium phosphate buffer (pH 7.0) containing 20 mM sodium L-lactate; reaction mixtures without sodium L-lactate were used as negative controls. The mixtures were incubated at 37° C. with shaking for 30 min at 250 RPM. For L-arginine oxidase assays, 0.45 ml of permeabilized cell suspensions were added to 0.45 ml of 0.2 M sodium phosphate buffer (pH 7.0) containing 20 mM L-arginine; reaction mixtures without arginine were used as negative controls. The mixtures were incubated at 37° C. with shaking for 2 h at 250 RPM. For NADH oxidase assays, 0.45 ml of permeabilized cell suspensions were added to 0.45 ml of 0.2 M sodium phosphate buffer (pH 7.0) containing 13 mM NADH (sodium salt); reaction mixtures without NADH were used as negative controls. The mixtures were incubated at 37° C. with shaking for 3 h at 250 RPM and the concentration of $H_2O_2$ in the supernates was determined.

Competition Assays on Agar Plates.

For competition assays between S. mutans UA159 and strains of A12 or S. gordonii DL1, an overnight culture of each strain was adjusted to $OD_{600}$=0.5 in BHI. An aliquot from each culture (6 µl) was inoculated adjacent to the other on agar plates as follows: (1) A12 or DL1 inoculated first, followed by inoculation of S. mutans 24 h later and an additional 24 h incubation; (2) S. mutans inoculated first, followed by inoculation with A12 or DL1 after 24 h plus an additional 24 h incubation; or (3) DL1 or A12 and S. mutans inoculated at the same time and incubation of the plates for a total of 24 h.

Bacteriocin Assays.

Overnight cultures of S. mutans UA159::pBGS, S. gordonii DL1, A12 and derivatives of these strains were centrifuged, washed twice with PBS, resuspended in PBS, and adjusted to $OD_{600}$=0.5. Then, S. mutans was mixed with other strains in a ratio of 1:1. Pure cultures or mixed cultures were spotted on BHI agar plates and grown aerobically or anaerobically. After 24 h incubation at 37° C., 3 ml of a soft agar overlay (1% BHI agar) containing $10^7$ cells of the indicator strain Streptococcus sanguinis SK150 was poured evenly onto the plate, the agar was allowed to set, and the plates were incubated for 24 h. Zones of inhibition were measured and documented with a digital imager. In some cases, the agar plug from mixed cultures was harvested, serially diluted and plated on selective agar to enumerate S. mutans, S. gordonii DL1, strain A12 or derivatives of these strains. CFUs were counted after incubation at 37° C. for 48 h.

Monitoring of comX and cipB Gene Promoter Activities.

The ability of supernates from A12 and S. gordonii to interfere with CSP or XIP signaling by S. mutans was assessed by monitoring the expression of genes that have been established to be activated by these peptides. Specifically, strains derived from S. mutans UA159 that carried lacZ reporter gene fusions to the promoter regions of cipB, encoding a bacteriocin (PcipB-lacZ), or to comX, encoding the alternative sigma factor required for development of genetic competence (PcomX-lacZ), were used to monitor the ability of S. mutans to respond to sCSP or sXIP, respectively. Supernates from overnight cultures of strains grown in BHI were obtained after removal of cells by centrifugation, the pH was adjusted to pH 7.0 and the supernates were filter-sterilized. A subset of aliquots of supernates were kept on ice while others were heat-treated to inactive putative proteases. sCSP was added to supernates to a final concentration of 2 µM and incubated for 3 h. Then, S. mutans UA159::PcipB-lacZ that had been grown to an $OD_{600}$=0.12 was suspended in the supernates. The cultures were then incubated for two hours and S. mutans cells were assayed for β-galactosidase activity. For XIP signaling, which occurs in defined medium, supernatant fluids from overnight cultures of A12 and its derivatives, S. gordonii or S. mutans UA159 that had been grown in FMC were adjusted to pH 7.0, supplemental glucose was added to increase the glucose concentration by 25 mM, and the supernates were filter-sterilized. sXIP was added to heat-treated or untreated supernates, as above, and incubated overnight at 37° C. Cultures of S. mutans UA159::PcomX-lacZ that had been grown in FMC to $OD_{600}$=0.12 were added to supernates. The cultures were incubated for two hours and LacZ assays were performed to detect XI P-dependent activation of the comX promoter. Where noted, A12 was also grown in anaerobic conditions or the supernates were treated with catalase to examine the influence of oxygen and/or hydrogen peroxide on the ability of A12 to inhibit peptide signaling.

LacZ (β-galactosidase) activity was measured using a modification of the Miller protocol (see Guo, 2014, incorporated by reference herein). Briefly, cells were harvested by centrifugation, washed once with Z buffer (Na-phosphate buffer, pH 7.0, 10 mM KCl, 1 mM $MgSO_4$, 5 mM β-mercaptoethanol), and resuspended in 1.2 ml of Z buffer. A 400 µl aliquot of the sample was vortexed with 20 µl of toluene:acetone (1:9) for 2 min and the mixture was kept at 37° C. The remainder of the cell suspension was used to measure $OD_{600}$. The reaction was initiated by the addition of 80 µl of an ONPG (o-nitrophenyl-β-D-galactopyranoside) solution (4 mg/ml) and was terminated by the addition of 400 µl of 1 M $Na_2CO_3$. Samples were centrifuged at 15,250×g for 1 min and the OD of the supernatant fluid was measured at 420 and 550 nm. β-galactosidase activity was expressed in Miller units.

Whole Genome Sequencing and Phylogenomic Analysis.

Genomic DNA was isolated using the Qiagen Genomic-tip 20/G columns and the Qiagen Genomic DNA buffer Set according to the supplier's protocol. A 10 kb library was made by the ICBR core at the University of Florida and sequenced using PacBio RSII SMRT sequencing technology. The Bioinformatics Core at the University of Florida assembled the genome using the SMRT Analysis Software. The genome was annotated using The RAST Server. A comprehensive phylogenetic analysis comparing A12 to 14 other members of the genus Streptococcus (eight species from the Mitis group, three species from the Sanguinis group, and three species from the Anginosus group) (data not shown) was performed as described by Richards et. al, 2014 (incorporated by reference herein). Briefly, an MCL cluster analysis was used to determine the core gene set. Core gene clusters were aligned and those judged to be recombinant were removed, leaving 374 putatively non-recombinant gene alignments. Two phylogenetic approaches were taken. In the first, a maximum likelihood (ML) phylogeny was generated from a concatenation of the 374 alignments. In the second, 374 separate ML phylogenies (gene trees) were constructed and a consensus phylogeny constructed.

Results

Effects of Arginine on ADS Induction in A12.

Figure 9A:
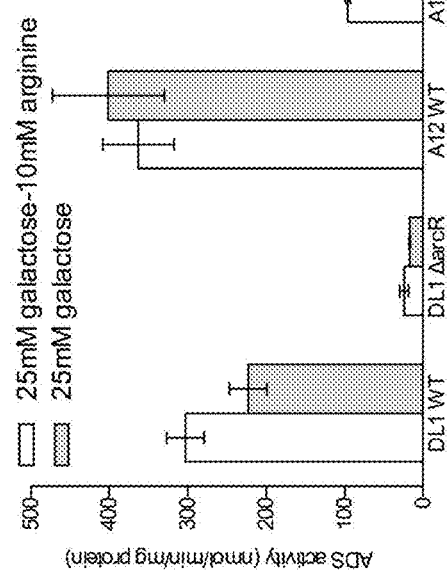
FIG. 9A is a bar graph illustrating arginine deiminase enzyme activity in S. gordonii DL1 and A12 WT and ΔarcR mutant strains grown in TY medium with or without supplemental arginine.
Figure 9B:
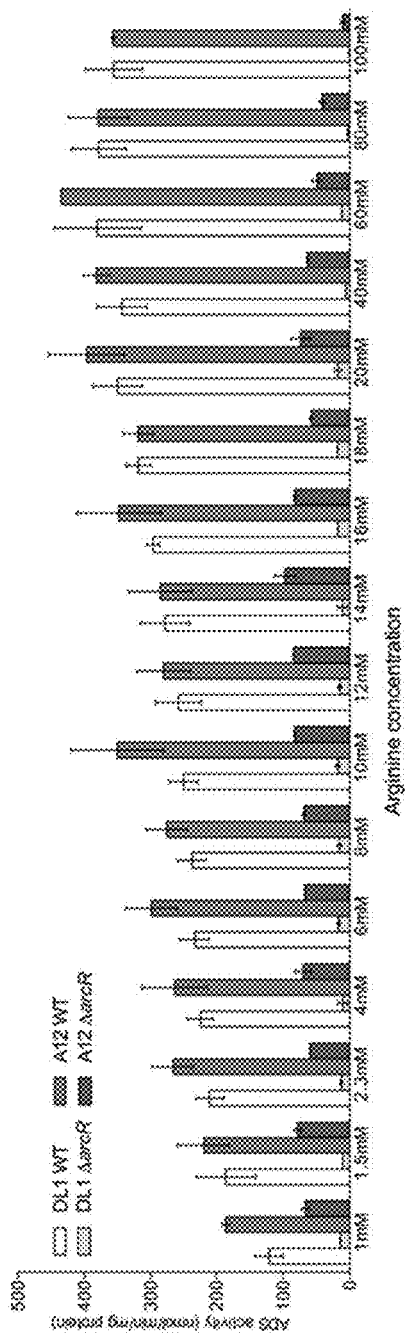
FIG. 9B illustrates arginine deiminase activity in WT and ΔarcR mutant strains of S. gordonii grown in the chemically defined medium FMC containing the indicated amount of arginine. A12 and S. gordonii DL1 were not able to grow in FMC medium unless some arginine was added. In 9A, the asterisks indicate statistical significance between the wild-type and arcR mutant strains in both growth conditions using an alpha of 0.05. In 9B, the comparisons are between the arcR mutants of A12 and S. gordonii.

Arginine deiminase (AD) enzyme activity in A12 was higher than the highly-arginolytic reference strain S. gordonii DL1 in cells growing under conditions that have been shown to be optimal for ADS expression in vitro (TY medium containing 25 mM galactose and 10 mM arginine). Full induction of AD activity in A12 did not require supplementation of TY-galactose with arginine, whereas supplementation with arginine was necessary for full expression of the ADS in DL1 (FIG. 9A) and many other $ADS^+$ bacteria. ArcR is the transcriptional activator of the ADS genes in streptococci, governing ADS gene expression in response to arginine. When arcR was inactivated in A12 and S. gordonii DL1, both strains produced much lower AD activity. S. gordonii DL1ΔarcR expressed only 8% of the AD activity of the parental strain, whereas A12 ΔarcR retained 25% of the AD activity of wild-type A12. TY medium contains 3% tryptone, so available arginine would be estimated to be in the 5-10 mM range and present primarily in peptide-form. To explore the requirement of arginine for ADS expression in more detail, cells were cultured in the chemically defined medium FMC with modified arginine content (FIG. 9B). In FMC lacking arginine, both A12 and DL1 were unable to grow (data not show). As the arginine levels in FMC were increased, both A12 and DL1 showed increased AD activity, with A12 producing higher AD levels than DL1, especially at lower concentrations of arginine. Both S. gordonii DL1 ΔarcR and A12 ΔarcR had much lower ADS levels compared to the wild-type strains, as observed with cells cultured in TY. However, S. gordonii DL1ΔarcR had almost no AD activity, whereas A12 ΔarcR retained considerable ADS activity under the same conditions. Collectively, these data reveal that A12 requires less arginine to produce substantial levels of AD activity and that ArcR-independent ADS gene expression may, at least in part, explain the higher constitutional arginolytic activity of A12.

A12 can Inhibit Growth of S. mutans by Pyruvate Oxidase-Dependent $H_2O_2$ Production.

Figure 10A:
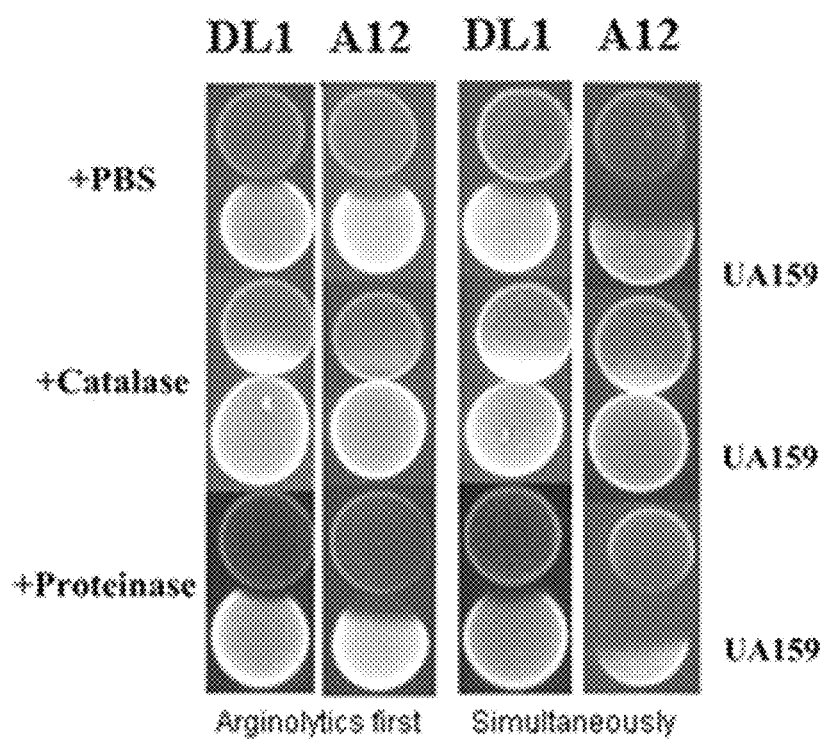
FIG. 10A is an illustration of plate-based growth inhibition assays of arginolytic strains versus S. mutans UA159. In all cases, overnight cultures were collected by centrifugation and resuspended at $OD_{600}$=0.5 in PBS. In the left two columns, the arginolytic strains S. gordonii DL1 or A12 were spotted onto plates and incubated for 24 h in a 5% CO2, aerobic atmosphere, then an equivalent amount of S. mutans UA159 was spotted adjacent to S. gordonii or A12 and the plates were incubated an additional 24 h. In the two columns on the right, A12 or S. gordonii DL1 was spotted at the same time as S. mutans UA159, and the plates were incubated for a total of 24 h. Addition of catalase to the medium effectively eliminated the inhibition of S. mutans by the commensal, but inclusion of proteinase K did not have the same effect.

Using a plate-based zone of inhibition assay, A12 could inhibit the growth of S. mutans UA159 in aerobic conditions more effectively than DL1 when inoculated prior to or simultaneously with S. mutans UA159. $H_2O_2$ was a factor in the inhibition since inclusion of catalase in the media effectively eliminated inhibition (FIG. 10A). Both A12 and DL1 produced substantial quantities of $H_2O_2$ (FIG. 10B) and displayed evidence of carbohydrate catabolite repression (CCR) of the activity responsible for $H_2O_2$ generation. More specifically, inhibition of S. mutans by A12 was less efficient on medium with glucose compared to medium containing galactose, which elicits little or no evidence of CCR. Using a less-rich version of TY medium (TY-D) also resulted in enhanced $H_2O_2$ production, further linking the inhibitory activity of A12 to nutrient source and availability. FIG. 10C shows that pyruvate oxidase (Pox) activity was the dominant source of $H_2O_2$ (FIG. 10C), with lactate oxidase, certain L-amino acid oxidases and NADH oxidase producing negligible amounts of $H_2O_2$ under the conditions tested. Notably, A12 expressed significantly higher Pox enzyme activity than S. gordonii DL1 (FIG. 10C).

Modulation of *S. mutans* Bacteriocin Production by A12.

As described in the methods section, a standard agar overlay antagonism assay was modified to examine mechanisms by which A12 may interfere with the growth of *S. mutans* and whether there were additional beneficial activities associated with A12. In particular, a dual-species cultivation system was created in which agar plates were co-inoculated with A12 and *S. mutans*, and the plates were subsequently overlaid with the indicator strain *S. sanguinis* SK150 that is sensitive to the mutacins produced by *S. mutans* UA159. This allowed us a) to examine whether A12 could modulate the capacity of *S. mutans* to kill sensitive streptococci and b) to enumerate, by removing and dispersing the bacteria at the inoculation site, the proportions of A12 and *S. mutans* remaining on the plates. First, virtually no *S. mutans* could be recovered after co-inoculation/co-cultivation with A12 in aerobic conditions (FIGS. 11A, 11C), whereas *S. mutans* accounted for nearly 60% of the recovered organisms in anaerobic conditions (FIGS. 11B, 11C); the difference being apparently attributable to $H_2O_2$-mediated killing of *S. mutans* in aerobic co-cultures. In fact, when the predicted homolog of the spxB gene of A12 encoding pyruvate oxidase was deleted, the mutant lost the ability to produce $H_2O_2$ during aerobic growth (data not shown) and to inhibit the growth of *S. mutans* in the dual species competition assay (data not shown).

Figure 11A:
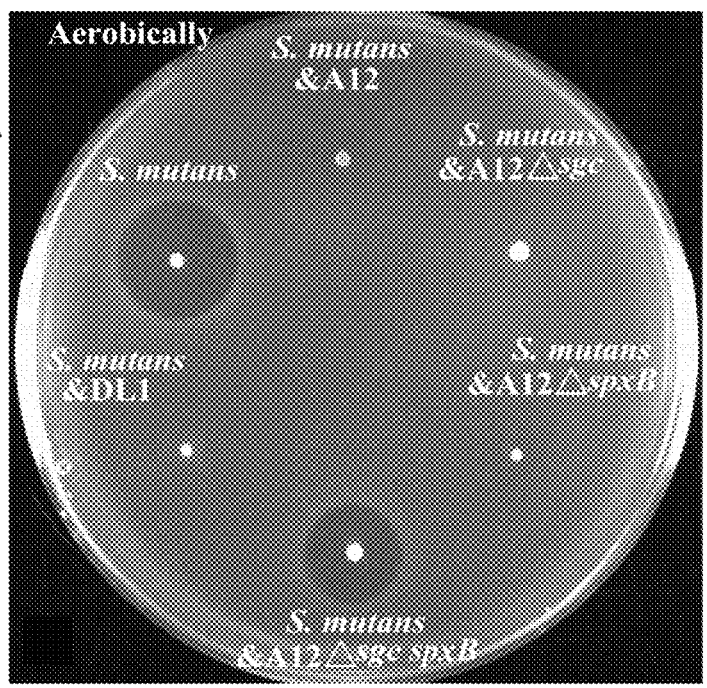
FIGS. 11A-11B are digital images illustrating plate-based mutacin assays using S. sanguinis SK150 as the indicator strain. The indicated strains were mixed in equal proportions, spotted onto BHI agar plates and the plates were incubated overnight in aerobic (FIG. 11A) or anaerobic (FIG. 11B) conditions. Subsequently, 3 ml of a soft BHI agar overlay containing $10^7$ S. sanguinis SK150 was gently and evenly overlaid onto the plate and incubation was continued for 24 h prior to measuring zones of inhibition. Mutants of A12 or S. gordonii lacking the Sgc protease were unable to block mutacin production to protect the indicator strain. An agar plug was obtained from the inoculation spot after the experiment, cells were dispersed, and the proportions of S. mutans UA159 and the indicated S. gordonii or A12 strain were enumerated by dilution and plating and graphed as illustrated in FIG. 11O.
Figure 11B:
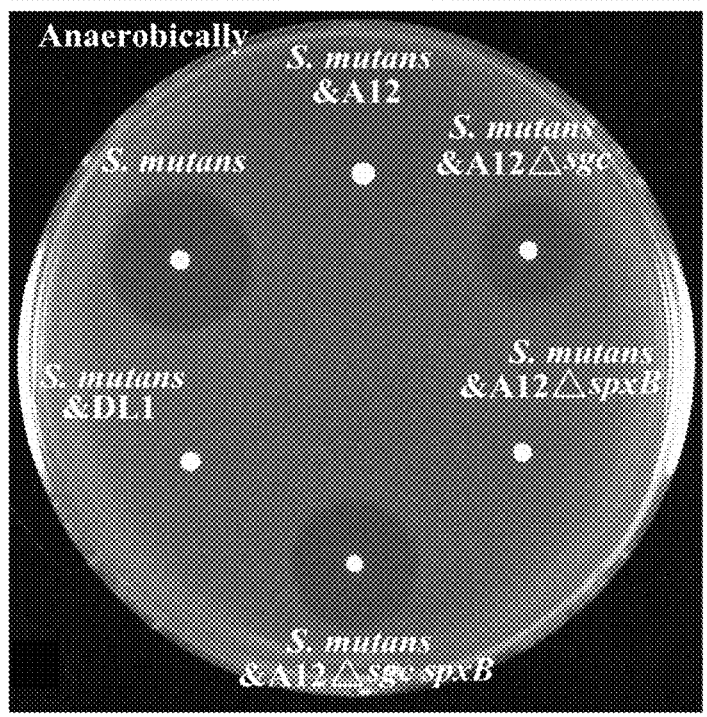
Figure 11C:
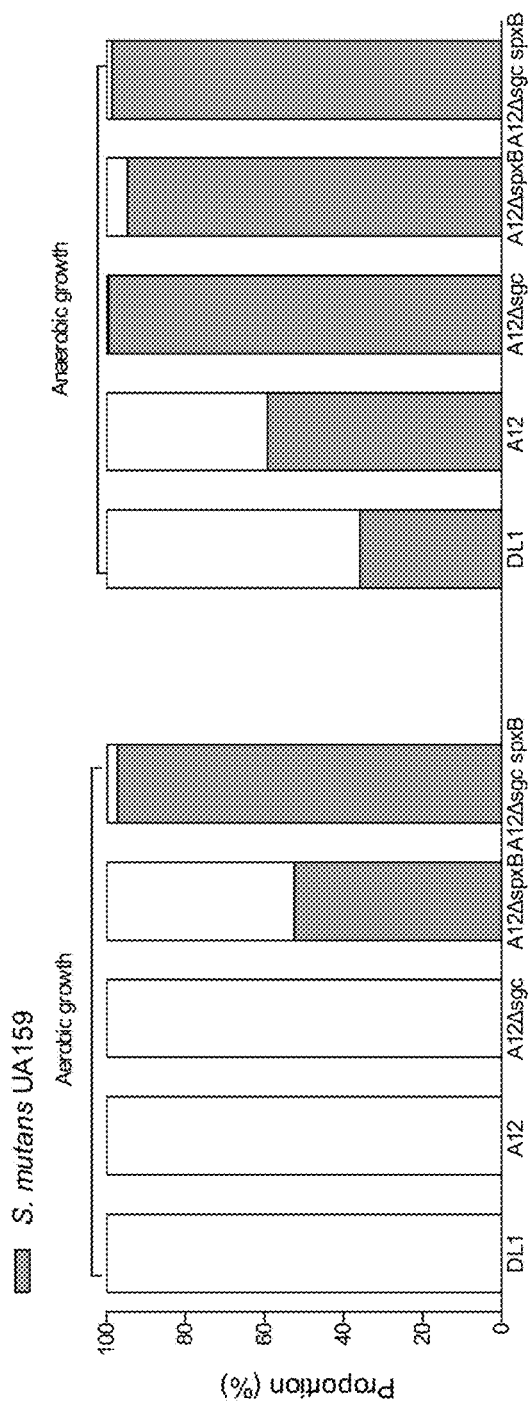

The same plate-based assay also revealed that the ability of *S. mutans* to produce bacteriocins that kill or inhibit the growth of *S. sanguinis* SK150 could be modulated by A12 and DL1. In particular, when UA159 and A12 were co-inoculated there was no evidence of inhibition of the indicator strain (FIGS. 11A and 11B). While the lack of inhibition of SK150 in aerobic conditions was easily explained by a failure of *S. mutans* to grow in the presence of A12 or DL1, the lack of inhibition of SK150 was equally as evident in anaerobic conditions. It has been reported that production by *S. gordonii* of a protease, termed Challisin and encoded by the sgc gene, is responsible for degrading CSP (see Wang, et al., 2005), the signal peptide that induces bacteriocin gene expression through the ComDE (see Hossain, et al., 2012) two-component signal transduction system of *S. mutans*. In this example it was possible to identify a gene for a putative Challisin-like protease in the genome of A12 that had 60.4% amino acid sequence identity to *S. gordonii* Challisin. Mutant strains of A12 and DL1 were created that lacked the predicted sgc homologs as detailed in the methods section. When *S. mutans* and A12Δsgc were co-cultured in aerobic conditions, there was no killing of the indicator strain and no *S. mutans* were recovered, so loss of Sgc did not impede the ability of A12 to inhibit *S. mutans* via $H_2O_2$ production. Interestingly, in anaerobic conditions, the proportions of the colony represented by the A12Δsgc mutant were substantially lower than for the A12 wild-type strain. Similarly, when *S. mutans* and the A12ΔspxB strain were grown together aerobically, A12 accounted for almost 50% of the colony, but only 5% in anaerobic conditions (FIG. 11C). Notwithstanding, even when A12 represented as little as 5% of the recovered organisms, there was still no killing of the indicator strain (FIG. 11B). Importantly, the A12Δsgc spxB double mutant strain lost both the ability to inhibit *S. mutans* through $H_2O_2$ production (data not shown) and to protect the indicator strain from inhibition. However, again it was noted that the proportions of *S. mutans* were greater when co-cultivated with the spxB single mutant than with the spxB sgc double mutant. Therefore, it must be considered that the poorer competition of A12 strains carrying the sgc mutation may indicate that Sgc provides some protection to A12 against antagonistic factors of *S. mutans*.

Figure 12:
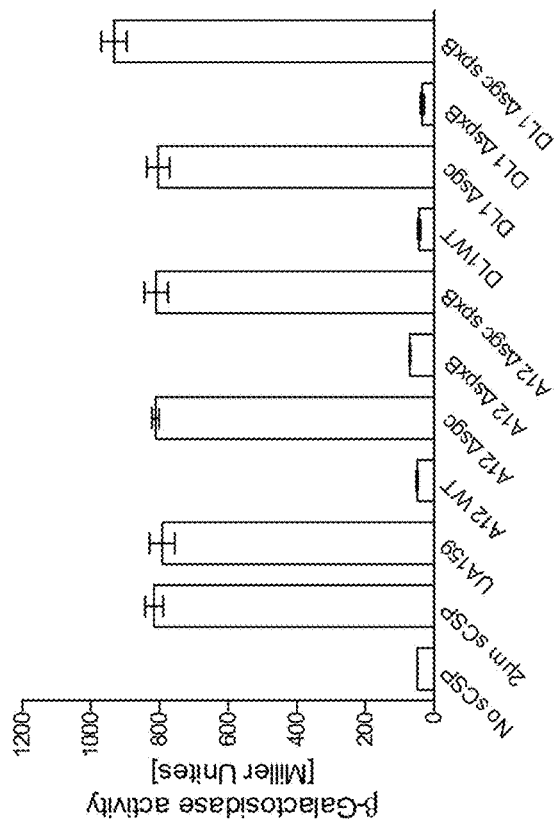
FIG. 12 is a bar graph illustrating the effects of treatment of sCSP with supernates from overnight cultures of the indicated strains. A strain of S. mutans containing a lacZ fusion to the cipB promoter was grown to $OD_{600}$=0.12 in BHI (optimal responsiveness to sCSP). Supernates from overnight cultures of the indicated strains were obtained after centrifugation, adjustment to pH 7.0 (also optimal for sCSP signaling) and filter sterilized. sCSP was added to the supernates and the mixtures were incubated for 2 h. Then, the S. mutans cipB-lacZ reporter strain was resuspended in the indicated supernate for 2 h prior to measurement of β-galactosidase (LacZ) activity. The Sgc protease was necessary for inhibition of sCSP signaling. The results shown are from a minimum of three biological replicates, each performed in triplicate. Values are averages and error bars indicate standard deviations.

To address in more detail the mechanisms by which A12 might impact the capacity of *S. mutans* to produce bacteriocins, the ability of supernates from the wild-type and sgc mutant strains derived from A12 and DL1 to degrade CSP was assessed by monitoring CSP-dependent signaling through ComDE using a cipB-lacZ promoter-reporter fusion. When 2 μm sCSP was incubated for 3 h with supernates of A12 or *S. gordonii* DL1, there was almost no induction of LacZ activity (FIG. 12). If the supernates were boiled for 20 min prior to incubation with sCSP (data not shown), LacZ activity expressed from the cipB promoter was similar to the sCSP control or to treatment of sCSP with supernates from *S. mutans* (FIG. 12). Importantly, supernates from the Δsgc mutants of A12 and DL1 lost the ability to degrade sCSP (FIG. 12). We also examined the ability of supernates from spxB mutants of A12 and DL1 to degrade sCSP (FIG. 12) and saw no differences compared to the wild-type strains. However, the A12Δsgc spxB and DL1Δsgc spxB double mutants were unable to degrade sCSP.

A12, but not *S. gordonii* DL1, Inhibits XIP-Dependent Signaling.

Figure 13:
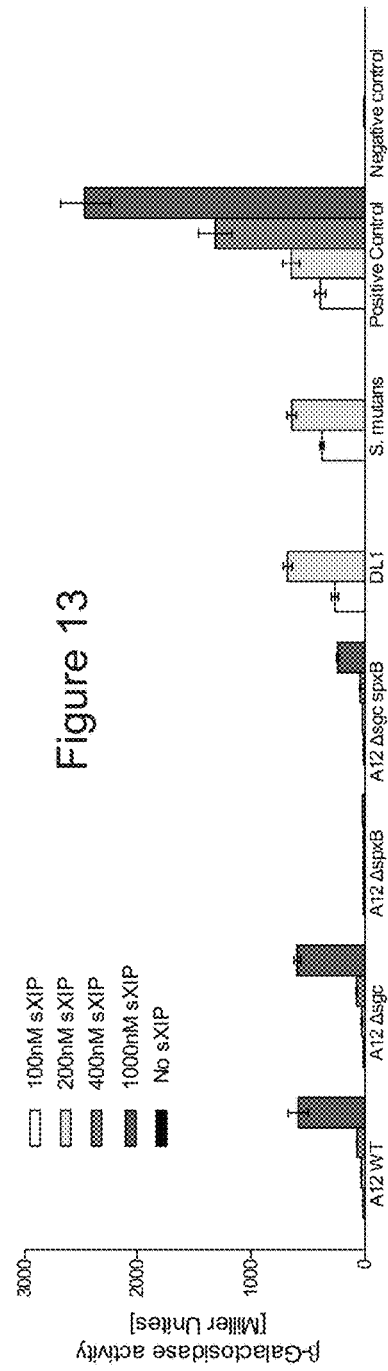
FIG. 13 is a bar graph illustrating effects of treatment of XIP with supernates from overnight cultures of the indicated strains. Supernatant fluids from overnight cultures of A12 and its derivatives, S. gordonii or S. mutans UA159 that had been grown in FMC were adjusted to pH 7.0, supplemental glucose was added to increase the glucose concentration by 25 mM, and the supernates were filter-sterilized. sXIP was added to the supernates, and the mixtures were incubated overnight at 37° C. Cultures of S. mutans UA159::PcomX-lacZ that had been grown in FMC to $OD_{600}$=0.12 were pelleted by centrifugation and resuspended in the supernates. The cultures were incubated for two hours, and LacZ assays were performed to detect XIP-dependent activation of the comX promoter. The results shown are from a minimum of three biological replicates, each performed in triplicate. Values are averages and error bars indicate standard deviations. The 400 or 1000 nM sXIP for DL1 and S. mutans are not shown because neither supernates influenced sXIP signaling any differently to the positive control. The asterisks indicate statistical significance in comparisons between A12 wild-type/200 nM XIP and DL1/200 nM XIP, and between A12 wild-type/1000 XIP and the Spx-deficient A12/1000 nM XIP.
Figure 14:
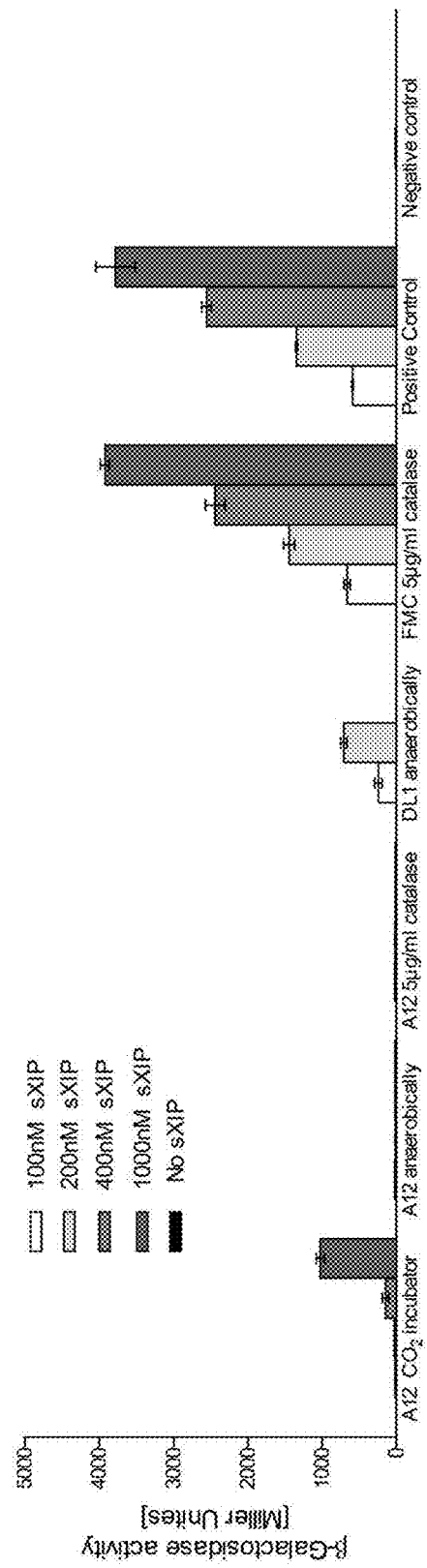
FIG. 14 is a bar graph illustrating the effects of growth conditions on the interference of XIP signaling by supernates from overnight cultures of the indicated strains. All experiments were performed as detailed for FIG. 13 except cells were grown in different atmospheres or supernates were treated with catalase. Supernates from A12 grown anaerobically had an apparently enhanced capacity to interfere with sXIP signaling and the effects were not impacted by inclusion of catalase. S. gordonii again was unable to interfere with sXIP signaling and the 400 or 1000 nM sXIP for DL1 are not shown because there was no difference from the positive control. Catalase itself also had no effect on signaling (FMC 5 µg/ml catalase bars). The results shown are from a minimum of three biological replicates, each performed in triplicate. Values are averages and error bars indicate standard deviations. Asterisks indicate statistical significance between A12 grown in $CO_2$ versus anaerobically and A12 grown in $CO_2$ versus catalase treatment.

CSP is able to substantially enhance the ability of *S. mutans* to be transformed with exogenous DNA, but activation of competence by CSP is indirect. The proximal regulator of the comX gene encoding the alternative sigma factor that activates late competence gene expression is ComR, and ComR binding is regulated by the XIP signal peptide. The ability of supernates from A12 and DL1 to degrade XIP were compared using the same methods as those used for CSP, with the exception that the experiments were performed in chemically defined FMC medium and a derivative of *S. mutans* UA159 carrying a fusion of the comX promoter to lacZ was used as the reporter for XIP-dependent activation of gene expression. After overnight treatment of XIP with supernates from *S. gordonii* DL1, XIP signaling was as robust as in the untreated controls, i.e. untreated sXIP in media alone or sXIP added to supernates from *S. mutans* UA159 (FIG. 13). In contrast, exposure of sXIP to supernates from wild-type A12 eliminated the ability of sXIP to activate comX. If the supernates of A12 were boiled, XIP activation of comX was similar to the sXIP controls (data not shown), indicating that the activity responsible for degradation or interference with sXIP was heat sensitive. Interestingly, deletion of the sgc gene of A12 did not eliminate the ability of supernates from A12 to inhibit sXIP signaling, and deletion of spxB resulted in an enhanced ability of supernates from A12 to inhibit sXIP signaling. The primary difference in the A12 wild-type strain and the A12 ΔspxB is that the former can produce substantial quantities of $H_2O_2$ and the latter almost no $H_2O_2$ under the conditions used for these particular experiments. When A12 was grown in either BHI or FMC broth in static conditions in a 5% $CO_2$ aerobic atmosphere, no $H_2O_2$ was detected in supernates of overnight cultures (data not shown). To be certain that the effects on XIP were not associated with $H_2O_2$, supernates were pretreated with catalase prior to addition of XIP (FIG. 14). As was noted with the spxB mutant, elimination of $H_2O_2$ resulted in an enhancement of the capacity of the supernates from A12 to block sXIP-dependent activation of comX. Thus, the production or stability of the activity that interferes with XIP signaling may be enhanced in anaerobic conditions, perhaps reflecting an adaptation that could enhance protection of A12 against *S. mutans* when A12 is unable to produce $H_2O_2$.

Whole Genome Sequencing and Phylogenomic Analysis of A12.

Figure 15:
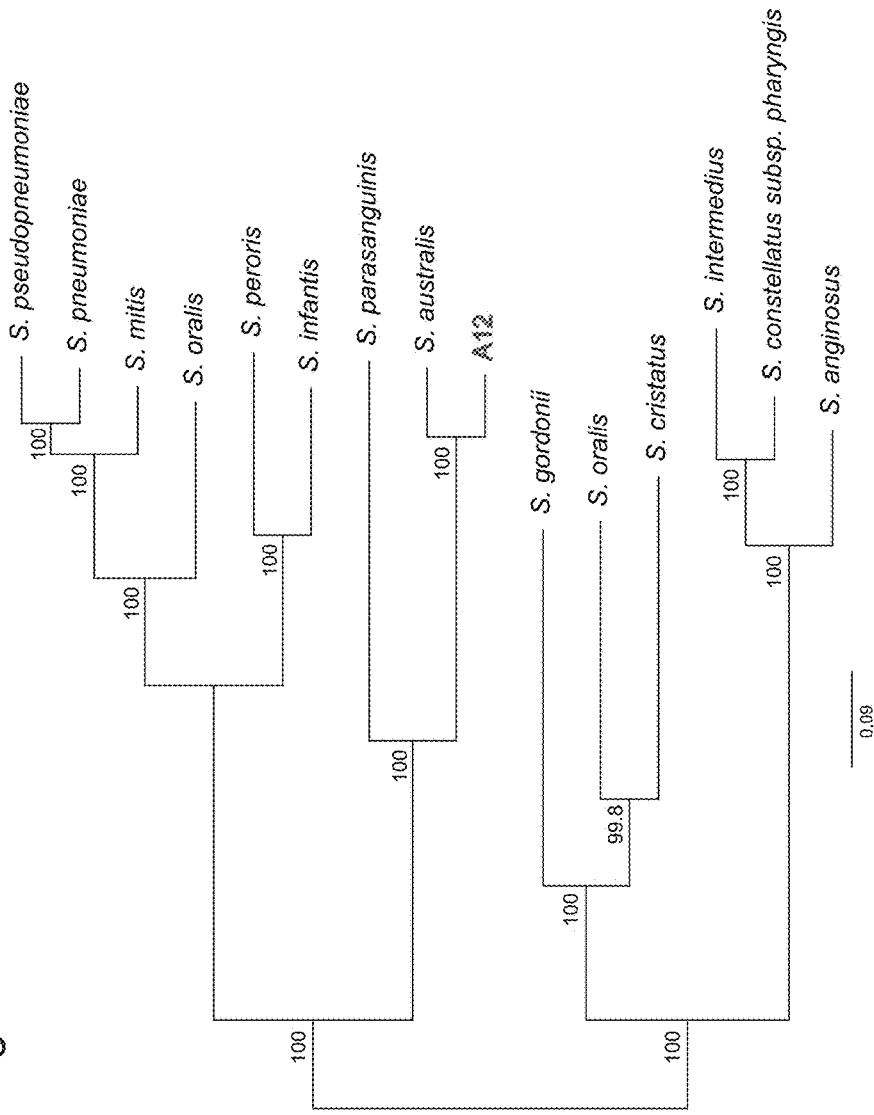
FIG. 15 illustrates the maximum likelihood phylogeny showing relationship among 14 Streptococcus species and A12. Numbers on branches show the proportion of gene phylogenies that support the grouping.

Comparison of the entire 16S sequence of A12 by Blast revealed that the 16S rDNA was most highly conserved with that of the reference strain for *Streptococcus australis* (NCBI Reference Sequence: NZ_AFUD01000002.1: http://www.ncbi.nlm.nih.gov/nuccore/NZ_AFUD01000002.1). To more carefully evaluate the relatedness of A12 to other streptococci, the entire genome sequence of A12 was determined using PacBio to attain 60X coverage. A single 1.8 Mb contig was obtained and annotated (Biosample accession number is SAMN04287214), and a comprehensive phylogenomic analysis was conducted by methodologies described in Richards, et al., 2014. Using these approaches, it was determined (FIG. 15) that the patristic distance (i.e. divergence between lineages) between A12 and its closest relative *S. australis* was 0.058 (5.8% divergence), whereas the patristic distance between *Streptococcus pneumoniae* and *Streptococcus pseudopneumoniae*, two distinct species, was 0.049 (4.9%). It may be possible that A12 represents a new species of *Streptococcus*, since the phylogenomic analysis suggests that A12 may not be definitively classified as *S. australis* or *S. parasanguinis*. Of note, A12 has a distinctive colony morphology from other commonly isolated oral streptococcal species and comparison of the translated sequence of certain genes from A12 with apparent homologs from *S. australis* or *S. parasanguinis* revealed substantial degeneracies, which has proven useful in distinguishing A12-like organisms from close relatives in plaque samples. With this knowledge, it has been possible to isolate a small number of putative A12-like organisms from clinical samples. All of the isolates showed the expected sequence conservation in a gene of interest, with significant differences notable with *S. australis* and *S. parasanguinis* (data not shown), along with constitutively high ADS activity and potent antagonistic capacity against *S. mutans* (data not shown).

Discussion

In light of the strong correlation between the absence of dental caries and high dental plaque ADS activity, oral bacteria with constitutionally high ADS expression have significant potential for applications in probiotic therapies to prevent and control dental caries. Since such strains would be even more desirable if they could antagonize the growth of known caries pathogens, the present example characterized a novel *Streptococcus*, designated A12, with the ability to express high ADS activity under conditions that commonly occur in human dental biofilms and to also have a particularly potent inhibitory effect on the growth of *S. mutans*, mainly through pyruvate oxidase-dependent $H_2O_2$ production. Moreover, A12 is able to interfere with the two dominant intercellular peptide-based communication pathways of *S. mutans*, which has the impact of disabling a primary antagonistic strategy (bacteriocins) of *S. mutans* while rendering *S. mutans* unable to induce genetic competence; competence being associated with nutritional benefits, genome diversification, acid tolerance and biofilm formation. The identification of an oral isolate with this combination of characteristics, couples with the findings on the tremendous heterogeneity of commensal streptococci in example 2, above, as a demonstration of the phenotypic capacity and plasticity of the oral microbiome as these factors relate to the behaviors of particular taxa and populations. The data also reinforce the importance of complementing current metagenomic approaches that utilize 16S rRNA sequence with more in-depth approaches to characterize the oral microbiota if reliable correlations of the composition and activities of the microbiome and oral health are to be established.

The ADS is widely distributed among prokaryotes, and the primary structures of the enzymes in the pathway have been conserved throughout evolution. Most microorganisms studied so far have their ADS genes organized into one cluster. In *S. gordonii*, which has the most extensively characterized ADS of any oral bacterium, the genes for the three enzymes of the pathway, arginine deiminase (AD; arcA), ornithine carbamyltransferase (arcB) and carbamate kinase (arcC), are co-transcribed in an operon with arcD (arginine: ornithine antiporter) and arcT (arginine aminopeptidase). Induction of the ADS genes (arcABCDT) by arginine is mediated by a transcriptional activator encoded by the divergently transcribed arcR gene located immediately downstream of the arcABCDT operon. Notably, arcR of *S. gordonii* is the second gene in a two-gene operon that includes the queA gene, which has been shown in other organisms to catalyze the final step in queosine modification of tRNAs. QueA-deficient *S. gordonii* mutants show altered ADS expression. An Fnr-like protein (flp) is encoded immediately upstream of arcA and is important for activation of expression of the arcA promoter in anaerobic conditions. Catabolite repression of the operon by preferred carbohydrate sources (CCR), such as glucose, is exerted primarily through CcpA binding to two cis-acting catabolite responses elements near the arcA promoter.

There are some similarities of the ADS operon of A12 with those of its closest relatives *S. australis* and *S. parasanguinis*, and with the well-characterized operon of *S. gordonii* DL1 (not shown). Most notably, arcABCDT of A12 appear to be co-transcribed, as is the case for arcABCDT of *S. gordonii* DL1. Also present in A12 are arcR and queA, which are immediately downstream of arcT and transcribed in the opposite direction, as is the case for *S. gordonii*. There is also an apparent homologue of the flp gene upstream of arcA; with Flp of A12 sharing 63% sequence identity (82% similarity) with Flp of *S. gordonii*. The promoter for the *S. gordonii* arcA gene has been mapped and is located the proper distance from a fairly well conserved −10 sequence, but a weaker −35 sequence. A near-consensus −10 sequence was identified in A12 that is located one nt closer to the arcA start codon than the −10 element of *S. gordonii*. However, the predicted −35 sequence of A12, which is also one nt closer to the initiation codon than that of *S. gordonii*, was more similar to the consensus than the *S. gordonii*-35 element. Also, similar to *S. gordonii* and consistent with the fact that both genes appear to require a transcriptional activator (ArcR) for optimal expression, an ArcR binding site was identified upstream of arcA.

The arc operons of *S. gordonii* and A12 are sensitive to CCR, although A12 is less so. In particular, in cells grown in the presence of 25 mM glucose, AD activity in *S. gordonii* DL1 was only about 15% of that expressed in cells growing on 25 mM galactose, whereas A12 growing on glucose retained more than 50% of the AD activity in cells growing on 25 mM galactose. Catabolite repression of the ADS operon of *S. gordonii* is predominantly regulated by CcpA, which is predicted to bind to two conserved catabolite response elements (CRE) located in the arcA promoter region. Two sequences in the A12 arcA promoter region with conservation to the derived consensus sequence (see, Zeng, et al., 2006) for binding of the catabolite control protein CcpA could be identified at positions −116 to −104 and −34 to −21 in the A12 operon; essentially in the same positions as the CREs in *S. gordonii*, with respect to the arcA start codon. The upstream CcpA binding site in A12 at −116 to −104 has four nucleotides that differ from the consensus sequence, whereas the binding site at −21 to −34 had one nucleotide that differed from the consensus. Overall, then, adherence of the CREs to the consensus sequence was not as high in A12 as for the CREs in the arcA promoter region of S. gordonii. While functional analysis of promoter strength and the effectiveness of the putative cis- and trans-acting factors in induction and repression of the ADS of A12 remain to be determined, the constitutionally higher levels of A12 ADS activity may be associated with an inherently stronger promoter and diminished CcpA-dependent CCR.

As shown in Example 2, above, the level of ADS activity expressed by multiple commensal streptococci under ideal conditions can be highly variable across and within species, as can the ability of the system to be repressed by carbohydrate or oxygen, or induced by arginine. Thus, it is believed that there may be an evolutionary basis for this inter- and intraspecies variation that leads to certain isolates, like A12, having higher constitutive ADS gene expression and a diminished sensitivity to CCR and other factors. A12 and similar isolates may have evolved to rely more heavily on the ADS for protection from the detrimental effects of low pH, whereas low ADS producers or strains that are more sensitive to repression by environmental inputs, such as high levels of carbohydrate, evolved other acid tolerance strategies; for example higher proton-extruding ATPase activity, $H^+$-ATPases with lower optimal pH values, diminished membrane proton permeability, or other traits associated with resistance to low pH. Should this hypothesis be proven correct, it can then be extrapolated that this latter group of commensals, with lower ADS expression and higher inherent acid tolerance might tend to be associated with caries activity, whereas the former group would tend to be associated with health.

A variety of oral streptococci that are predominant members of early and mature biofilms are able to generate $H_2O_2$, which is thought to have a profound impact on the composition and biochemical activities of the microbiota. NADH oxidase enzymes were believed to be a primary source of $H_2O_2$ in the oral cavity, but more recent studies support that other enzymatic pathways may contribute substantially to endogenously generated $H_2O_2$ in oral biofilms. In particular, pyruvate oxidase (Pox), which is encoded by spxB, is a major source of $H_2O_2$ produced by A12, S. sanguinis, S. gordonii and some other arginolytic streptococci. Utilization of pyruvate via Pox in aerobic conditions may have several benefits for those organisms that produce the enzyme, as well as having a beneficial impact on biofilm ecology. In particular, Pox directly converts pyruvate and inorganic phosphate to the high energy intermediate acetyl phosphate (AcP), which can be used for ATP synthesis by acetate kinase. AcP also serves as a signal molecule and as a substrate for certain two-component systems. Thus, Pox provides bioenergetic benefits while potentially contributing to optimization of gene expression and physiology through modulation of AcP levels. Pox also liberates $CO_2$, which can be converted to bicarbonate by carbonic anhydrases to buffer biofilms against acidification. It is also notable that, in aerobic conditions, Pox shunts pyruvate away from lactate and toward production of the weaker organic acid acetate, which may further diminish the extent of dental plaque acidification. S. oligofermentans and some isolates of S. gordonii and S. cristatus (data not shown) can also produce $H_2O_2$ from lactic acid via the lactate oxidase (Lox) enzyme. L-amino acid oxidases in these (LAAO) species may also contribute, to a lesser degree, to $H_2O_2$ by these organisms. However, Lox, LAAO(s) or NADH oxidase do not appear to be major contributors to $H_2O_2$ generation by A12 or S. gordonii DL1 compared to Pox, under the conditions tested.

The production of Pox by A12 also appears sensitive to CCR, which is consistent with what has been reported for certain other commensal streptococci (Zheng, et al., 2011) and with the presence of a CRE in the promoter region for the spxB gene in A12 with only one mismatch from the consensus CRE. Clearly, then, there may be conditions in dental biofilms that are not favorable for $H_2O_2$-dependent inhibition of S. mutans; such as when oral biofilms become more anaerobic and/or when there is sufficient dietary carbohydrate ingested by the host to repress the expression of gene products needed for $H_2O_2$ production. In this regard, the demonstration that A12 has evolved strategies to subvert the bacteriocin- and competence-activating signal pathways of S. mutans, and that these systems remain active in anaerobic conditions and when glucose is abundant (FIGS. 11, 4) may be highly significant to the role of A12 in antagonism of S. mutans and protection of beneficial organisms.

Mutacin production has been postulated, although not directly demonstrated, to be an essential ecological determinant that enhances the establishment, persistence and emergence of S. mutans in cariogenic biofilms. Two factors have been shown to dominantly control bacteriocin expression in S. mutans, CSP and exposure to oxygen. CSP, at levels as low as 30 nM, are sufficient to rapidly and robustly induce the lantiobiotic and non-lantibiotic bacteriocins of S. mutans, as well as an endogenous bacteriocin (CipB) that has been proposed to play a role in altruistic cell death. Growth in air also dramatically induces bacteriocin production by S. mutans, with the gene for the non-lantiobiotic mutacin (n/mD) being induced over 40-fold in cells exposed to oxygen compared to cells cultured anaerobically. Thus, S. mutans, when in early or immature dental biofilms where oxygen and redox may be fairly high (66), may activate mutacin expression as a deterrent to competition with those commensals that are better adapted to tolerate growth in the presence of air. Conversely, when biofilms mature and oxygen levels and redox drop significantly, S. mutans can still activate mutacin gene expression through accumulation of the CSP signal. While commensals that are competing with S. mutans may gain an advantage in aerated conditions through $H_2O_2$ production, the possession by A12, S. gordonii, and possibly other health-associated oral streptococci of an activity that can degrade CSP may offer protection from mutacins in mature biofilms. There is also a role for CSP in competence and cell lysis, the latter providing eDNA that can stabilize biofilms by serving as part of the extracellular matrix. While much remains to be learned about CSP signaling, competence and programmed cell death, as well as how these factors influence plaque ecology, interference with the CSP signaling pathway would be predicted to diminish the ability of S. mutans to persist and emerge as a dominant member of the oral flora.

Phylogenomic studies clearly show that S. mutans is a remarkably diverse species and that this genomic diversity is, in large part, attributable to its highly efficient capacity to acquire genes through lateral gene transfer; mainly due to its ability to become genetically competent (transformable). Conjugation and bacteriophage, on the other, do not appear to be major contributors to genetic diversity in this caries pathogen. While CSP can clearly enhance transformability of S. mutans, the primary control point for activation of competence genes is through the ComRS-XIP system described earlier. Interestingly, while isolates of S. mutans show considerable heterogeneity in terms of the CSP-ComDE system, with some strains completely lacking the genes and others having divergent sequences or pseudogenes, the ComRS systems shows remarkably high conservation and is part of the core genome. A full appreciation of the contribution of XIP and ComRS to *S. mutans* colonization, growth in vivo, persistence or virulence has not yet been realized, but the high degree of evolutionary conservation and the essential role of ComRS in competence development provide significant support for an essential role(s) for this system and for strong evolutionary pressure to maintain a fully functional ComRS-XIP pathway. In this regard, the unusual capacity of A12 to interfere with XIP-dependent signaling may be a particularly beneficial attribute, if for no other reason than DNA may be an important nutrient source in vivo. Clearly, though, our data show that the A12 activity that interferes with XIP signaling is not produced by *S. gordonii*, under the conditions tested, and that it is distinct from the Sgc enzyme. Recently, the *PepO* protease in group A streptococci has been shown to degrade small hydrophobic signal peptides, including XIP. A12 contains a gene with 71% identity and 82% similarity to the PepO protease of *Streptococcus pyogenes*. Potential candidates for XI P degrading activity in A12 are currently being explored.

Finally, there is the question of whether A12-like bacteria represent a new species of *Streptococcus* that occupies a niche in oral biofilms that distinguishes them from their closest relatives, *S. australis* and *S. parasanguinis*. The phylogenomic analyses utilized in this study revealed that the relatedness of A12 to *S. australis* is less than that of two established streptococcal species, *Streptococcus pneumoniae* and pseudopneumoniae. While it would be premature to propose A12 as a new species, the distinct colony morphology and ability to find highly conserved genes in what appear to be A12-like organisms that have diverged substantially in sequence from apparent homologs in *S. australis* or *S. parasanguinis* should allow us to gather sufficient data to establish whether designation as a new species is warranted. Regardless of the outcome, A12 is an isolate that is both highly arginolytic and is able to inhibit the growth and intercellular signaling in *S. mutans* in a way that may promote the stability of health-associated biofilm communities. By contrasting the genome sequences of A12-like organisms and isolates with similar beneficial properties with poorly arginolytic and poorly antagonistic members of the same taxa, it is possible to develop the molecular probes and other tools that can be utilized to ascertain the extent to which the biofilms of human subjects are populated with beneficial organisms. Such knowledge could aid the practice of clinical dentistry by augmenting caries risk assessment and improving the ability to evaluate the impact of therapeutic approaches on oral microbiomes.

REFERENCES

Aas J A, Griffen A L, Dardis S R, Lee A M, Olsen I, Dewhirst F E, Leys E J, Paster B J: Bacteria of dental caries in primary and permanent teeth in children and young adults. J Clin Microbiol 2008; 46:1407-1417.

Aas J A, Paster B J, Stokes L N, Olsen I, Dewhirst F E: Defining the normal bacterial flora of the oral cavity. J Clin Microbiol 2005; 43:5721-5732.

Becker M R, Paster B J, Leys E J, Moeschberger M L, Kenyon S G, Galvin J L, Boches S K, Dewhirst F E, Griffen A L: Molecular analysis of bacterial species associated with childhood caries. J Clin Microbiol 2002; 40:1001-1009.

Burne R, Liu, Y, Zeng, L: Acid tolerance strategies of commensal and pathogenic oral streptococci.; in: Society for General Microbiology Autumn 2010 Meeting. Nottingham, U K, 2010.

Burne R A, Marquis R E: Alkali production by oral bacteria and protection against dental caries. FEMS Microbiol Lett 2000a; 193:1-6.

Burne R A, Marquis R E: Alkali production by oral bacteria and protection against dental caries. FEMS Microbiol Lett 2000b; 193:1-6.

Burne R A, Parsons, D. T. and Marquis, R. E.: Environmental variables affecting arginine deiminase expression in oral streptococci. Washington, D C, 1991.

Casiano-Colon A, Marquis R E: Role of the arginine deiminase system in protecting oral bacteria and an enzymatic basis for acid tolerance. Appl Environ Microbiol 1988; 54:1318-1324.

Caufield P W, Dasanayake A P, Li Y, Pan Y, Hsu J, Hardin J M: Natural history of *Streptococcus sanguinis* in the oral cavity of infants: evidence for a discrete window of infectivity. Infect Immun 2000; 68:4018-4023

Clancy K A, Pearson S, Bowen W H, Burne R A: Characterization of recombinant, ureolytic *streptococcus mutans* demonstrates an inverse relationship between dental plaque ureolytic capacity and cariogenicity. Infection and immunity 2000; 68:2621-2629.

Corby P M, Lyons-Weiler J, Bretz W A, Hart T C, Aas J A, Boumenna T, Goss J, Corby A L, Junior H M, Weyant R J, Paster B J: Microbial risk indicators of early childhood caries. J Clin Microbiol 2005; 43:5753-5759.

Crielaard W, Zaura E, Schuller A A, Huse S M, Montijn R C, Keijser B J: Exploring the oral microbiota of children at various developmental stages of their dentition in the relation to their oral health. BMC Med Genomics 2011; 4:22.

Dawes C, Dibdin G H: Salivary concentrations of urea released from a chewing gum containing urea and how these affect the urea content of gel-stabilized plaques and their ph after exposure to sucrose. Caries Res 2001; 35:344-353.

De Jong M H, Van Der Hoeven J S, Van Os J H: Growth of micro-organisms from supragingival dental plaque on saliva agar. J Dent Res 1986; 65:85-88.

Dewhirst F E, Chen T, Izard J, Paster B J, Tanner A C, Yu W H, Lakshmanan A, Wade W G: The human oral microbiome. J Bacteriol 2010; 192:5002-5017.

Dong Y, Chen Y Y, Burne R A: Control of expression of the arginine deiminase operon of *streptococcus gordonii* by ccpa and flp. J Bacteriol 2004; 186:2511-2514.

Fowler M L, Ingram-Smith C J, Smith K S: Direct detection of the acetate-forming activity of the enzyme acetate kinase. J Vis Exp 2011; 58: e3474

Gross E L, Leys E J, Gasparovich S R, Firestone N D, Schwartzbaum J A, Janies D A, Asnani K, Griffen A L: Bacterial 16s sequence analysis of severe caries in young permanent teeth. J Clin Microbiol 2010; 48:4121-4128.

Guo Q, Ahn S J, Kaspar J, Zhou X, Burne R A. 2014. Growth phase and pH influence peptide signaling for competence development in *Streptococcus mutans*. J Bacteriol 196:227-236.

He J, Hwang G, Liu Y, Gao L, Kilpatrick-Liverman L, Santarpia P, Zhou X, Koo H: L-arginine modifies the exopolysaccharides matrix and thwarts *Streptococcus*

*mutans* outgrowth within mixed-species oral biofilms. J Bacteriol 2016; 198(19):2651-2661.

Huang X, Schulte R M, Burne R A, Nascimento M M. 2015. Characterization of the arginolytic microflora provides insights into pH homeostasis in human oral biofilms. Caries Res 49:165-176.

Huang X, Palmer S R, Ahn S-J, Richards V P, Williams M L, Nascimento M M, Burne R A: A highly arginolytic *Streptococcus* species that potently antagonizes *Streptococcus mutans*. Appl Environ Microbiol 2016; 82:2187-2201.

Hossain M S, Biswas I. 2012. An extracelluar protease, SepM, generates functional competence-stimulating peptide in *Streptococcus mutans* UA159. J Bacteriol 194: 5886-5896.

Kleinberg I: Biochemistry of the dental plaque. Advances in oral biology 1970; 4:43-90.

Kleinberg I, Jenkins G N: The ph of dental plaques in the different areas of the mouth before and after meals and their relationship to the ph and rate of flow of resting saliva. Arch Oral Biol 1964; 72:493-516.

Kohler B, Andreen I: *Mutans* streptococci and caries prevalence in children after early maternal caries prevention: a follow-up at 19 years of age. Caries Res 2012; 46:474-480.

Kohler B, Andreen I, Jonsson B: The earlier the colonization by *mutans* streptococci, the higher the caries prevalence at 4 years of age. Oral Microbiol Immunol 1988; 3:14-17.

Kreth J, Merritt J, Shi W, Qi F: Competition and coexistence between *Streptococcus mutans* and *Streptococcus sanguinis* in the dental biofilm. J Bacteriol 2005; 187:7193-7203.

Kreth J, Zhang Y, Herzberg M C: Streptococcal antagonism in oral biofilms: *Streptococcus sanguinis* and *Streptococcus gordonii* interference with *Streptococcus mutans*. J Bacteriol 2008; 190:4632-4640.

Liu L, Tong H, Dong X: Function of the pyruvate oxidase-lactate oxidase cascade in interspecies competition between *Streptococcus oligofermentans* and *Streptococcus mutans*. Appl Environ Microbiol 2012; 78:2120-2127.

Liu Y, Burne R A: Multiple two-component systems modulate alkali generation in *streptococcus gordonii* in response to environmental stresses. J Bacteriol 2009; 191:7353-7362.

Liu Y, Burne R A: The major autolysin of *streptococcus gordonii* is subject to complex regulation and modulates stress tolerance, biofilm formation, and extracellular-DNA release. J Bacteriol 2011; 193:2826-2837.

Liu Y, Dong Y, Chen Y Y, Burne R A: Environmental and growth phase regulation of the *streptococcus gordonii* arginine deiminase genes. Appl Environ Microbiol 2008; 74:5023-5030.

Mager D L, Ximenez-Fyvie L A, Haffajee A D, Socransky S S: Distribution of selected bacterial species on intraoral surfaces. J Clin Periodontol 2003; 30:644-654.

Margolis H C, Duckworth J H, Moreno E C: Composition and buffer capacity of pooled starved plaque fluid from caries-free and caries-susceptible individuals. J Dent Res 1988a; 67:1476-1482.

Margolis H C, Duckworth J H, Moreno E C: Composition and buffer capacity of pooled starved plaque fluid from caries-free and caries-susceptible individuals. J Dent Res 1988b; 67:1476-1482.

Marquis R E: Oxygen metabolism, oxidative stress and acid-base physiology of dental plaque biofilms. Journal of industrial microbiology 1995; 15:198-207.

Marquis R E, Bender G R, Murray D R, Wong A: Arginine deiminase system and bacterial adaptation to acid environments. Appl Environ Microbiol 1987a; 53:198-200.

Marquis R E, Bender G R, Murray D R, Wong A: Arginine deiminase system and bacterial adaptation to acid environments. Appl Environ Microbiol 1987b; 53:198-200.

Nascimento M M, Gordan V V, Garvan C W, Browngardt C M, Burne R A: Correlations of oral bacterial arginine and urea catabolism with caries experience. Oral Microbiol Immunol 2009a; 24:89-95.

Nascimento M M, Gordan V V, Garvan C W, Browngardt C M, Burne R A: Correlations of oral bacterial arginine and urea catabolism with caries experience. Oral Microbiol Immunol 2009b; 24:89-95.

Nascimento M M, Liu Y, Kalra R, Perez S, Adewumi A, Xu X, Burne R A: Arginine metabolism may confer caries resistance in children. J Dent Res 2012; 91:691.

Palmer S R, Crowley P J, Oli M W, Ruelf M A, Michalek S M, Brady L J. 2012. YidC1 and YidC2 are functionally distinct proteins involved in protein secretion, biofilm formation and cariogenicity of *Streptococcus mutans*. Microbiology 158:1702-1712.

Paster B J, Boches S K, Galvin J L, Ericson R E, Lau C N, Levanos V A, Sahasrabudhe A, Dewhirst F E: Bacterial diversity in human subgingival plaque. J Bacteriol 2001; 183:3770-3783.

Peterson P: Research for oral health in developing countires; in: WHO Global Forum for Health Research. Mexico city, Mexico, 2004.

Peterson S, Woodhead J, Crall J: Caries resistance in children with chronic renal failure: Plaque ph, salivary ph, and salivary composition. Pediatr Res 1985; 19:796-799.

Richards V P, Palmer S R, Pavinski Bitar P D, Qin X, Weinstock G M, Highlander S K, Town C D, Burne R A, Stanhope M J. 2014. Phylogenomics and the dynamic genome evolution of the genus *Streptococcus*. Genome Biol Evol 6:741-753.

Rogers A H: Utilization of nitrogenous compounds by oral bacteria. Aust Dent J 1990; 35:468-471.

Russell R R: How has genomics altered our view of caries microbiology? Caries Res 2008; 42:319-327.

Schulte R, Burne R A, Gordan V V, Nascimento M M: Alkali generation capacity of oral bacteria J Dent Res 2009; 88:1183.

Shu M, Morou-Bermudez E, Suarez-Perez E, Rivera-Miranda C, Browngardt C M, Chen Y Y, Magnusson I, Burne R A: The relationship between dental caries status and dental plaque urease activity. Oral Microbiol Immunol 2007a; 22:61-66.

Shu M, Morou-Bermudez E, Suarez-Perez E, Rivera-Miranda C, Browngardt C M, Chen Y Y, Magnusson I, Burne R A: The relationship between dental caries status and dental plaque urease activity. Oral Microbiol Immunol 2007b; 22:61-66.

Sissons C H, Hancock E M, Cutress T W: The source of variation in ureolysis in artificial plaques cultured from human salivary bacteria. Arch Oral Biol 1988a; 33:721-726.

Sissons C H, Hancock E M, Perinpanayagam H E, Cutress T W: The bacteria responsible for ureolysis in artificial dental plaque. Arch Oral Biol 1988b; 33:727-733.

Sissons C H, Wong L, Hancock E M, Cutress T W: The ph response to urea and the effect of liquid flow in 'artificial mouth' microcosm plaques. Arch Oral Biol 1994; 39:497-505.

Stephan R M: Changes in hydrogen-ion concentration on tooth surfaces and in carious lesions. J Am Dent Assoc 1940; 27:718-723.

Tong H, Chen W, Merritt J, Qi F, Shi W, Dong X: Streptococcus oligofermentans inhibits Streptococcus mutans through conversion of lactic acid into inhibitory $H_2O_2$: a possible counteroffensive strategy for interspecies competition. Mol Microbiol 2007; 63:872-880.

Van Wuyckhuyse B C, Perinpanayagam H E, Bevacqua D, Raubertas R F, Billings R J, Bowen W H, Tabak L A: Association of free arginine and lysine concentrations in human parotid saliva with caries experience. J Dent Res 1995; 74:686-690.

Vander Wauven C, Pierard A, Kley-Raymann M, Haas D: Pseudomonas aeruginosa mutants affected in anaerobic growth on arginine: Evidence for a four-gene cluster encoding the arginine deiminase pathway. J Bacteriol 1984; 160:928-934.

Wang B-Y, Kuramitsu H K. 2005. Interactions between oral bacteria: inhibition of Streptococcus mutans bacteriocin production by Streptococcus gordonii. Appl Environ Microbiol 71:354-362.

Warburton P J, Ciric L, Lerner A, Seville L A, Roberts A P, Mullany P, Allan E. 2013. TetAB(46), a predicted heterodimeric ABC transporter conferring tetracycline resistance in Streptococcus australis isolated from the oral cavity. J Antimicrob Chemother 68:17-22.

Wen Z T, Burne R A. 2001. Construction of a new integration vector for use in Streptococcus mutans. Plasmid 45:31-36.

Wijeyeweera R L, Kleinberg I: Arginolytic and ureolytic activities of pure cultures of human oral bacteria and their effects on the ph response of salivary sediment and dental plaque in vitro. Arch Oral Biol 1989a; 34:43-53.

Wijeyeweera R L, Kleinberg I: Arginolytic and ureolytic activities of pure cultures of human oral bacteria and their effects on the ph response of salivary sediment and dental plaque in vitro. Arch Oral Biol 1989b; 34:43-53.

Zeng L, Dong Y, Burne R A. 2006. Characterization of cis-acting sites controlling arginine deiminase gene expression in Streptococcus gordonii. J Bacteriol 188:941-949.

Zeng L, Martino N C, Burne R A: Two gene clusters coordinate galactose and lactose metabolism in Streptococcus gordonii. Appl Environ Microbiol 2012; 78:5597-5605.

Zheng L, Chen Z, Itzek A, Ashby M, Kreth J: Catabolite control protein A controls hydrogen peroxide production and cell death in Streptococcus sanguinis. J Bacteriol 2011; 193:516-526.

Zhu L, Kreth J: The role of hydrogen peroxide in environmental adaptation of oral microbial communities. Oxid Med Cell Longev 2012; 2012:717843.

TABLE 8

Listing of sequences and SEQ ID NOs

| SEQ ID NO: | Sequence | Description of synthetic sequence |
|---|---|---|
| 1 | AGAGTTTGAT CCTGGCTCAG | forward 16S rRNA primer sequence |
| 2 | TACGGGTACC TTGTTACGAC T | reverse 16S rRNA primer sequence |
| 3 | TTTCACACCCGAGCTCTTAC | primer for A12-arcR-5'-F |
| 4 | ACTCCTTCTGGTGGCGACTTTCAATCTTATTC | primer for A12-arcR-5'-R-SOE |
| 5 | GTCGCCACCAGAAGGAGTGATTACATGAACAAA | primer for A12-arcR-Erm-F-SOE |
| 6 | GAGGCAGACCCCTTTAGTAACGTGTAACTTT | primer for A12-arcR-Erm-R-SOE |
| 7 | ACTAAAGGGGTCTGCCTCATCATCTGTGAA | primer for A12-arcR-3'-F-SOE |
| 8 | CTCTCCATTGATGAACAGCAA | primer for A12-arcR-3'-R |
| 9 | GAATTGGCGCAAGGGATGATAA | primer for A12-spx8-5'-F |
| 10 | TTTCTACAGGATAGTGTCTACGCCCCATGTT | primer for A12-spx8-5'-R-SOE |
| 11 | GACACTATCCTGTAGAAAAGAGGAAGGAA | primer for A12-spxB-Kan-F-SOE |
| 12 | TGGTACAAGGAGTATGGACAGTTGCGGATGTA | primer for A12-spxB-Kan-R-SOE |
| 13 | TCCATACTCCTTGTACCATTCCGTCTCTTC TT | primer for A12-spx8-3'-F-SOE |
| 14 | CCACTTACTAGCAGGGATTCGGTT | primer for A12-spx8-3'-R |
| 15 | CCATTTGGCCAAGGAGAGTTGTT | primer for A12-sgc-5'-F |
| 16 | CACTCCTTCGAACAGATCCTAATAGCACCGA | primer for A12-sgc-5'-R-SOE |
| 17 | GATCTGTTCGAAGGAGTGATTACATGAACAA | primer for A12-sgc-Erm-F-SOE |
| 18 | CAGGATTAGCCCTTTAGTAACGTGTAACTTT | primer for A12-sgc-Erm-R-SOE |
| 19 | ACTAAAGGGCTAATCCTGGTGCTAGTCAA | primer for A12-sgc-3'-F-SOE |
| 20 | CCTGGAGAAGAACTATACGTAA | primer for A12-sgc-3'-R |

TABLE 8-continued

Listing of sequences and SEQ ID NOs

| SEQ ID NO: | Sequence | Description of synthetic sequence |
|---|---|---|
| 21 | TCATGGATTGAGCTCAAAAAGTAAT | primer for cipB5' promoter region |
| 22 | TGTATTCATGGATCCAATACCCCTT | primer for cipB3' promoter region |

The invention claimed is:

1. A method of increasing the amount of ammonia-producing bacteria in the oral cavity of a host, the method comprising:
   administering to a host a probiotic oral composition comprising:
      a mixture of isolated bacterial strains, the mixture comprising at least two different isolated arginolytic bacterial strains, each strain capable of producing ammonia via the arginine deiminase system (ADS) and each strain meeting at least one of the following criteria: expressing ADS activity in the absence of supplemental arginine, expressing ADS activity in the presence of glucose, expressing ADS activity in a non-acidic pH, expressing ADS activity under aerobic conditions, inhibiting the growth of at least one bacterial strain associated with dental caries, and resisting inhibition of growth by at least one bacterial strain associated with dental caries, wherein the ability of the isolated arginolytic bacterial strain to express ADS activity under any of said criteria is determined with respect to an ADS activity level of S. gordonii DL1 under the same conditions, wherein an ADS activity level about the same or higher than the ADS activity of S. gordonii DL1 under the same conditions indicates the strain meets the criteria; and
      a pharmaceutically acceptable oral carrier,
   wherein at least two of the criteria are met by the mixture of bacterial strains at an ADS activity level greater than the ADS activity level of S. gordonii DL1 under the same conditions, wherein the composition does not include *Streptococcus mutans* and does not include strains of bacteria from any other bacterial species associated with dental caries, and wherein administration of the probiotic oral composition increases the amount of ammonia-producing bacteria in the oral cavity of the host over the amount of ammonia-producing bacterial in the oral cavity of the host prior to administration of the probiotic oral composition.

2. The method of claim 1, wherein the bacterial strain associated with dental caries is *Streptococcus mutans*.

3. The method of claim 1, wherein the probiotic oral composition further comprises one or more compounds capable of increasing the ADS activity of the bacterial strains with respect to the ADS activity of the strains in the absence of the compounds.

4. The method of claim 3, wherein the compound to increase the ADS activity of the bacterial strains is arginine.

5. The method of claim 1, wherein the mixture comprises: at least one arginolytic bacterial strain capable of expressing ADS activity in the absence of supplemental arginine, at least one arginolytic bacterial strain capable of expressing ADS activity in the presence of glucose, at least one arginolytic bacterial strain capable of expressing ADS activity in a non-acidic pH, at least one arginolytic bacterial strain capable of expressing ADS activity under aerobic conditions, and at least one arginolytic bacterial strain capable of inhibiting the growth of at least one bacterial strain associated with dental caries or capable of resisting inhibition of growth by at least one bacterial strain associated with dental caries.

6. The method of claim 1, wherein at least one of the isolated arginolytic bacterial strains comprises *Streptococcus* A12.

7. A method of increasing the amount of ammonia-producing bacteria in the oral cavity of a host, the method comprising:

administering to a host a probiotic oral composition comprising:
a mixture of isolated bacterial strains, the mixture comprising: an isolated arginolytic bacterial strain *Streptococcus* A12 and at least one other isolated arginolytic bacterial strain capable of producing ammonia via the arginine deiminase system (ADS) and meeting at least one of the following criteria: expressing ADS activity in the absence of environmental arginine, expressing ADS activity in the presence of glucose, expressing ADS activity in a non-acidic pH, expressing ADS activity under aerobic conditions, inhibiting the growth of at least one bacterial strain associated with dental caries, and resisting inhibition of growth by at least one bacterial strain associated with dental caries; and
a pharmaceutically acceptable oral carrier.

8. The method of claim 7, wherein the probiotic oral composition further comprises one or more compounds capable of increasing the ADS activity of the bacterial strains with respect to the ADS activity of the strains in the absence of the compounds.

9. The method of claim 8, wherein the compound to increase the ADS activity of the bacterial strains is arginine.

10. A method of treatment comprising:
administering to a host a probiotic oral composition comprising an isolated arginolytic bacterial strain *Streptococcus* A12.

11. The method of claim 10, wherein the probiotic oral composition further comprises one or more compounds capable of increasing the ADS activity of *Streptococcus* A12 with respect to the ADS activity of *Streptococcus* A12 in the absence of the compounds.

12. The method of claim 11, wherein the compound to increase the ADS activity of the bacterial strains is arginine.

13. A method of preventing the incidence of dental caries, reducing the incidence of dental caries, slowing or arresting the progression of dental caries lesions, or a combination of these in a host, the method comprising:

administering to a host a probiotic oral composition comprising:
a mixture of isolated bacterial strains, the mixture comprising at least two different isolated arginolytic bacterial strains, each strain capable of producing ammonia via the arginine deiminase system (ADS) and each strain meeting at least one of the following criteria: expressing ADS activity in the absence of environmental arginine, expressing ADS activity in the presence of glucose, expressing ADS activity in a non-acidic pH, expressing ADS activity under aerobic conditions, inhibiting the growth of at least one bacterial strain associated with dental caries, and resisting inhibition of growth by at least one bacterial strain associated with dental caries, wherein the ability of the isolated arginolytic bacterial strain to express ADS activity under any of said criteria is determined with respect to an ADS activity level of *S. gordonii* DL1 under the same conditions, wherein an ADS activity level about the same or higher than the ADS activity of *S. gordonii* DL1 under the same conditions indicates the strain meets the criteria; and
a pharmaceutically acceptable oral carrier,
wherein at least two of the criteria are met by the mixture of bacterial strains at an ADS activity level greater than the ADS activity level of *S. gordonii* DL1 under the same conditions, wherein the composition does not include *Streptococcus mutans* and does not include strains of bacteria from any other bacterial species associated with dental caries.

14. The method of claim 13, wherein the probiotic oral composition further comprises arginine.

15. The method of claim 13, wherein the bacterial strain associated with dental caries is *Streptococcus mutans*.

* * * * *

UNITED STATES PATENT AND TRADEMARK OFFICE
CERTIFICATE OF CORRECTION

PATENT NO. : 10,206,959 B2  
APPLICATION NO. : 15/417669  
DATED : February 19, 2019  
INVENTOR(S) : Marcelle Matos Nascimento and Robert A. Burne Page 1 of 1

It is certified that error appears in the above-identified patent and that said Letters Patent is hereby corrected as shown below:

In the Specification

Column 1, Lines 22-28, replace the paragraph entitled STATEMENT REGARDING FEDERALLY SPONSORED RESEARCH OR DEVELOPMENT with the following paragraph:

--STATEMENT REGARDING FEDERALLY SPONSORED RESEARCH OR DEVELOPMENT
This invention was made with government support under DE025832, DE010362, and DE023579 awarded by The National Institutes of Health. The government has certain rights in the invention.--

Signed and Sealed this  
Fourth Day of February, 2020

Andrei Iancu  
*Director of the United States Patent and Trademark Office*